(12) United States Patent
O'Connor et al.

(10) Patent No.: US 12,264,349 B2
(45) Date of Patent: Apr. 1, 2025

(54) METHOD FOR PRODUCING MONOTERPENOID COMPOUNDS

(71) Applicant: John Innes Centre, Norwich (GB)

(72) Inventors: Sarah O'Connor, Norwich (GB);
Benjamin Robert Lichman, Heslington (GB)

(73) Assignee: John Innes Centre, Norwich (GB)

( * ) Notice: Subject to any disclaimer, the term of this patent is extended or adjusted under 35 U.S.C. 154(b) by 805 days.

(21) Appl. No.: 17/058,825

(22) PCT Filed: May 22, 2019

(86) PCT No.: PCT/GB2019/051409
§ 371 (c)(1),
(2) Date: Nov. 25, 2020

(87) PCT Pub. No.: WO2019/224536
PCT Pub. Date: Nov. 28, 2019

(65) Prior Publication Data
US 2021/0207183 A1 Jul. 8, 2021

(30) Foreign Application Priority Data
May 25, 2018 (GB) ..................................... 1808663

(51) Int. Cl.
*C12P 17/06* (2006.01)
*C12N 9/00* (2006.01)
*C12N 9/02* (2006.01)
*C12N 9/04* (2006.01)
*C12N 9/90* (2006.01)
*C12N 15/82* (2006.01)

(52) U.S. Cl.
CPC ............ *C12P 17/06* (2013.01); *C12N 9/0006* (2013.01); *C12N 9/001* (2013.01); *C12N 9/90* (2013.01); *C12N 15/8243* (2013.01); *C12Y 101/01* (2013.01); *C12Y 103/01* (2013.01); *C12Y 505/01* (2013.01)

(58) Field of Classification Search
CPC ....................................................... C12P 17/06
See application file for complete search history.

(56) References Cited

U.S. PATENT DOCUMENTS 10,696,991 B2 * 6/2020 Wawrzyn ................. C12N 1/20

FOREIGN PATENT DOCUMENTS

| CN | 1732264 A | 2/2006 |
| CN | 107002109 A | 8/2017 |
| WO | 2004/058976 A2 | 7/2004 |
| WO | 2009/102965 A2 | 8/2009 |
| WO | 2011/060027 A2 | 11/2010 |
| WO | 2011/060027 A3 | 5/2011 |
| WO | 2016/029153 A1 | 2/2016 |
| WO | 2016/107920 A1 | 7/2016 |

OTHER PUBLICATIONS

Sherden et al Phytochemistry 145:48-56 (Year: 2018).*
Sherden et al Phytochemstry preprint 2017 (Year: 2017).*
McElvain, S.M., et al., "The Constituents of the Volatile Oil of Catnip. I. Nepetalic Acid, Nepetalactone and Related Compounds", J. Am. Chem. Soc., Jun. 1941, pp. 1558-1563, vol. 63.
Formisano, C., et al., "Chemical Constituents and Biological Activities of Nepeta Species", Chemistry & Biodiversity (2011), pp. 1783-1818, vol. 8.
Todd, N.B., et al., "Inheritance of the Catnip Response in Domestic Cats", J. Hered., 1962, pp. 54-56, 53.
Bates, R. B., et al., "Terpenoids. cis-trans- and trans-cis-nepetalactones", Experientia 1963, pp. 564-565, 19.
Waller, G. R., et al., "Feline attractant, cis, trans-nepetalactone: metabolism in the domestic cat", Science 164, Jun. 13, 1969, pp. 1281-1282.
Dawson, G.W., et al., "Identification of an aphid sex pheromone", Nature 325, Feb. 12, 1987, pp. 614-616.
Clark, L.J., et al., "Analysis of monoterpenoids in glandular trichomes of the catmint Nepeta racemosa", The Plant Journal, 11(6), 1997, pp. 1387-1393.
Eisner, T., "Catnip: its raison d'etre", Science 146, 1964, pp. 1318-1320.
Birkett, M. A., et al., "Repellent activity of catmint, Nepeta cataria, and iridoid nepetalactone isomers against Afro-tropical mosquitoes, ixodid ticks and red poultry mites", Phytochemistry 72 (2011), Accepted Sep. 26, 2010, Available online Nov. 4, 2010, pp. 109-114.
Rajaonarivony, J. I. M., et al., "Characterization and mechanism of (4 S)-limonene synthase, a monoterpene cyclase from the glandular trichomes of peppermint (Mentha x piperita)", Archives of Biochemistry and Biophysics 296, Jul. 1992, pp. 49-57.
Poulter, C. D., et al., "Prenyltransferase. New evidence for an ionization-condensation-elimination mechanism with 2-fluorogeranyl pyrophosphate", J. Am. Chem. Soc. 99, Feb. 2, 1977, pp. 957-959.
Baunach, M., et al., "Terpenoid biosynthesis off the beaten track: unconventional cyclases and their impact on biomimetic synthesis", Angew. Chem. Int. Ed. Engl. 54, 2015, Published online Dec. 8, 2014, pp. 2604-2626.
Tantillo, D. J., "Importance of inherent substrate reactivity in enzyme-promoted carbocation cyclization/rearrangements", Angew. Chem. Int. Ed. Engl. 56, 2017, Accepted manuscript online Mar. 27, 2017, Version of record online Jun. 12, 2017, pp. 10040-10045.
Miettinen, K. et al., "The seco-iridoid pathway from Catharanthus roseus", Nature Communications 5:3606, 2014, Accepted Mar. 10, 2014, Published Apr. 7, 2014, pp. 1-11.
Geu-Flores, F., et al., "An alternative route to cyclic terpenes by reductive cyclization in iridoid biosynthesis", Nature 492, Dec. 6, 2012, pp. 138-142.

(Continued)

*Primary Examiner* — Brent T Page
(74) *Attorney, Agent, or Firm* — Scully, Scott, Murphy & Presser, P.C.

(57) ABSTRACT

The invention relates to enzymes and methods for producing a monoterpenoid compound. In one aspect, the invention is a method for producing a monoterpenoid compound, comprising the steps of (1) providing a monoterpenoid precursor; (2) providing a NEPS enzyme; and (3) contacting the monoterpenoid precursor with the enzyme under catalytic conditions to produce an monoterpenoid compound.

28 Claims, 57 Drawing Sheets

Specification includes a Sequence Listing.

(56) References Cited

OTHER PUBLICATIONS

O'Connor, S. E., et al., "Chemistry and biology of monoterpene indole alkaloid biosynthesis", Nat. Prod. Rep. 23, First published as an Advance Article on the web May 26, 2006, pp. 532-547.
Algana, F., et al., "Identification and characterization of the iridoid synthase involved in oleuropein biosynthesis in olive (Olea europaea) fruits", J. Biol. Chem. 291, Mar. 11, 2016, pp. 5542-5554.
Kries, H., et al., "Inverted stereocontrol of iridoid synthase in snapdragon", J. Biol. Chem. (2017) 292(35), Papers in Press, Jul. 12, 2017, pp. 14659-14667.
Hu, Y., et al., "Structures of iridoid synthase from Cantharanthus roseus with bound NAD+, NADPH, or NAD+/10-oxogeranial: reaction mechanisms", Angew. Chem. Int. Ed. Engl. 54, 2015, Revised Oct. 8, 2015, Published online Nov. 13, 2015, pp. 15478-15482.
Qin, L., et al., "Structure of iridoid synthase in complex with NADP+/8-oxogeranial reveals the structural basis of its substrate specificity", J. Struct. Biol. 194 (2016), Received in revised form Feb. 6, 2016, Accepted Feb. 8, 2016, Available online Feb. 8, 2016, pp. 224-230.
Dawson, G. W., et al., "The aphid sex pheromone cyclopentanoids: synthesis in the elucidation of structure and biosynthetic pathways", Bioorganic & Medicinal Chemistry, Apr. 1996, accepted Oct. 19, 1995, pp. 351-361.
Liblikas, I., et al., "Simplified isolation procedure and interconversion of the diastereomers of nepetalactone and nepetalactol", J. Nat. Prod. 68, 2005, pp. 886-890.
Cucinotta, C. S., et al., "Ab initio molecular dynamics study of the keto-enol tautomerism of acetone in solution", Chemphyschem, Jul. 2006, Published online on May 9, 2006, pp. 1229-1234.
Alagona, G., et al., "The catalytic effect of water on the keto-enol tautomerism", Pyruvate and acetylacetone: a computational challenge, Phys. Chem. Chem. Phys., Dec. 3, 2010, Accepted Jun. 22, 2010, pp. 10173-10188.
Schreiber, S. L., et al., "Stereochemistry of the intramolecular enamine/enal (enone) cycloaddition reaction and subsequent Transformations", J. Am. Chem. Soc. 108, 1986, pp. 8274-8277.
Moummou, H., et al., "The plant short-chain dehydrogenase (SDR) superfamily: genome-wide inventory and diversification patterns", BMC Plant Biol. 12:219 (2012), Accepted Nov. 16, 2012, Published Nov. 20, 2012, pp. 1-17.
Weng, J. K., et al., "The remarkable pliability and promiscuity of specialized metabolism", Cold Spring Harb. Symp. Quant. Biol., 2012, pp. 309-320, vol. LXXVII.
Tatsis, E. C., et al., "A three enzyme system to generate the Strychnos alkaloid scaffold from a central biosynthetic intermediate", Nat. Commun. 8:316 (2017), Accepted Jun. 6, 2017, pp. 1-10.
Davin, L. B., et al., "Stereoselective bimolecular phenoxy radical coupling by an auxiliary (dirigent) protein without an active center", Science 275, Jan. 17, 1997, pp. 362-366.
Pickel, B., et al., "An enantiocomplementary dirigent protein for the enantioselective laccase-catalyzed oxidative coupling of phenols", Angew. Chem. Int. Ed. Engl. 49, 2010, Published online Nov. 27, 2009, pp. 202-204.
Brown, S., et al., "De novo production of the plant-derived alkaloid strictosidine in yeast", PNAS, Mar. 17, 2015, pp. 3205-3210, vol. 112, No. 11.

Billingsley, J. M., et al., "Engineering the biocatalytic selectivity of iridoid production in Saccharomyces cerevisiae", Metabolic Engineering 44 (2017), Accepted Sep. 13, 2017, Available online Sep. 20, 2017, pp. 117-125.
Youn, B., et al., "Crystal structures of apo-form and binary/ternary complexes of Podophyllum secoisolariciresinol dehydrogenase, an enzyme involved in formation of health-protecting and plant defense lignans", J. Biol. Chem. 280, Apr. 1, 2005, and in revised form Jan. 7, 2005, Published, JBC Papers in Press, Jan. 13, 2005, pp. 12917-12926.
Mint Evolutionary Genomics Consortium, "Phylogenomic mining of the mints reveals multiple mechanisms contributing to the evolution of chemical diversity in Lamiaceae", Mol. Plant, Aug. 11, 2018, pp. 1084-1096.
Ringer, K. L., et al., "Monoterpene metabolism. Cloning, expression, and characterization of (−)-isopiperitenol/(−)-carveol dehydrogenase of peppermint and spearmint", Plant Physiology, Mar. 2005, pp. 863-872, vol. 137.
Munker, J., et al., "Iridoid synthase activity is common among the plant progesterone 5β-reductase family", Molecular Plant, Jan. 8, 2015, Accepted Sep. 15, 2014, Published Sep. 19, 2014, pp. 136-152.
Vizcaino, J.A., et al. "2016 update of the PRIDE database and its related tools", Nucleic Acids Research 2016, Published online Nov. 2, 2015, Revised Oct. 14, 2015; Accepted Oct. 16, 2015, pp. D447-D456, vol. 44.
Birkett M.A. et al., "Prospects of Genetic Engineering for Robust Insect Resistance", Current Opinion in Plant Biology 19:59-67 (2014).
Campbell A. et al., "Engineering of a Nepetalactol-Producing Platform Strain of Saccharomyces cerevisiae for the Production of Plant Seco-Iridoids", ACS Synth. Biol. 5:405-414 (2016).
Hallahan D.L. et al., "Nepetalactol Oxidoreductase in Trichomes of the Catmint Nepeta Racemosa", Phytochemistry 48(3):421-427 (1998).
Kries H. et al., "Structural Determinants of Reductive Terpene Cyclization in Iridoid Biosynthesis", Nature Chemical Biology 12:6-11 (Jan. 2016).
Kries H. et al., "Structural Determinants of Reductive Terpene Cyclization in Iridoid Biosynthesis", Nature Chemical Biology 12:6-11 (Jan. 2016), Supplementary Information.
Lichman B.R. et al., "Uncoupled Activation and Cyclization in Catmint Reductive Terpenoid Biosynthesis", Nature Chemical Biology 15:71-79 (Jan. 2019).
Lichman B.R. et al., "Uncoupled Activation and Cyclization in Catmint Reductive Terpenoid Biosynthesis", Nature Chemical Biology 15:71-79 (Jan. 2019), Supplementary Information.
Sherden N.H. et al., "Identification of Iridoid Synthases from Nepeta Species: Iridoid Cyclization Does Not Determine Nepetalactone Stereochemistry", Phytochemistry 145:48-56 (2018).
NCBI Reference Sequence No. XM_011073454.2 (3 pages) (Apr. 6, 2017).
EBI Accession No. GSP:BDC01565 (1 page) (Aug. 25, 2016).
British Search Report dated Jan. 30, 2019 received in British Application No. GB 1808663.7.
International Search Report and Written Opinion dated Jul. 10, 2019 received in International Application No. PCT/GB2019/051409.

* cited by examiner

Fig. 2C
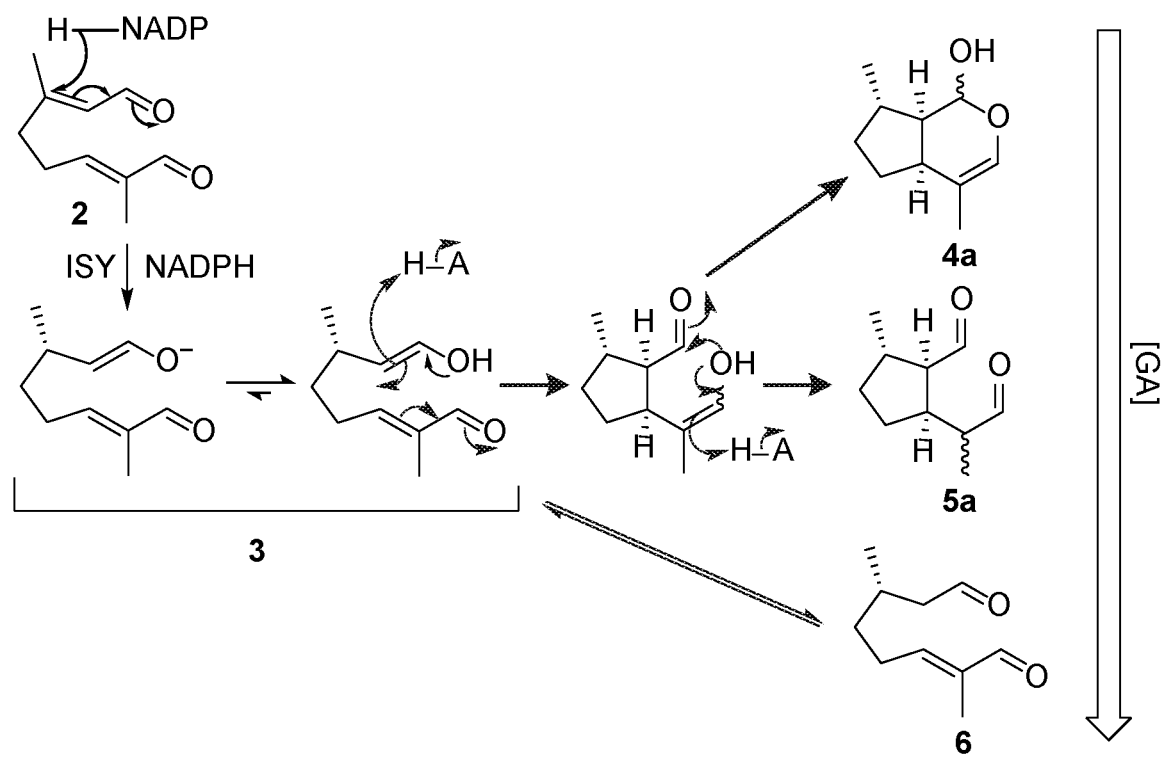
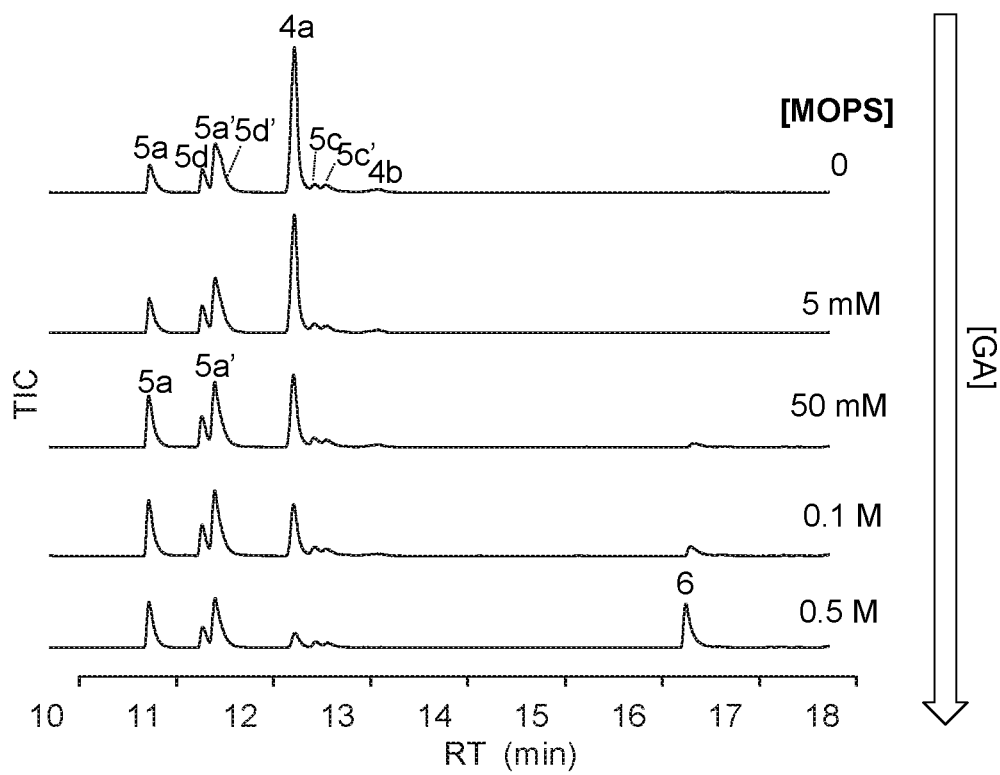

Fig. 3B
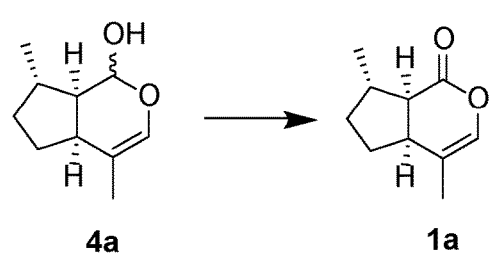 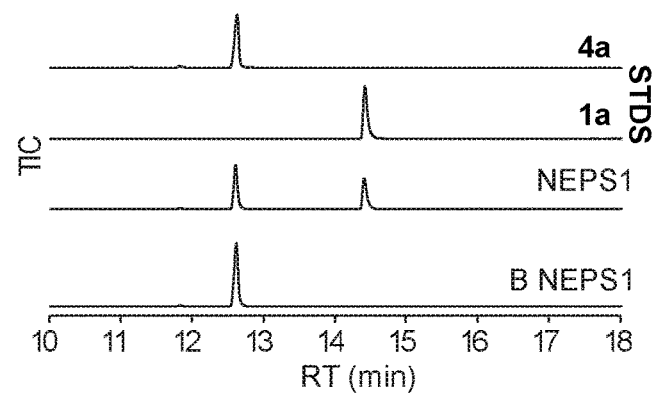
Fig. 3C
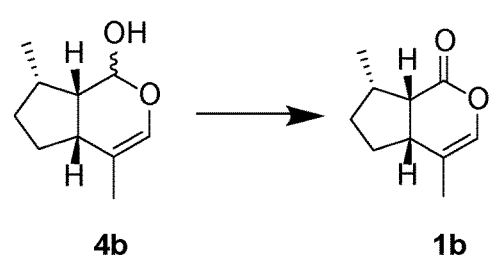 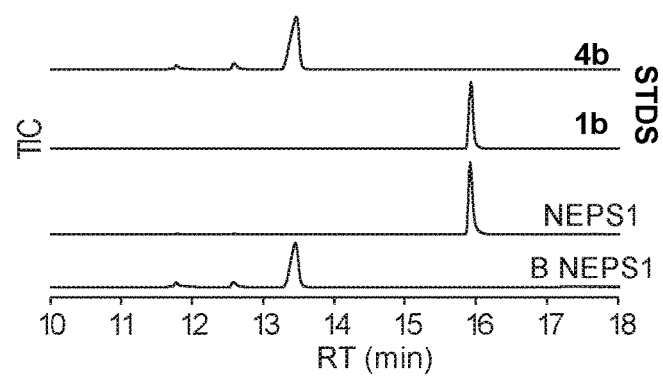

Fig. 5
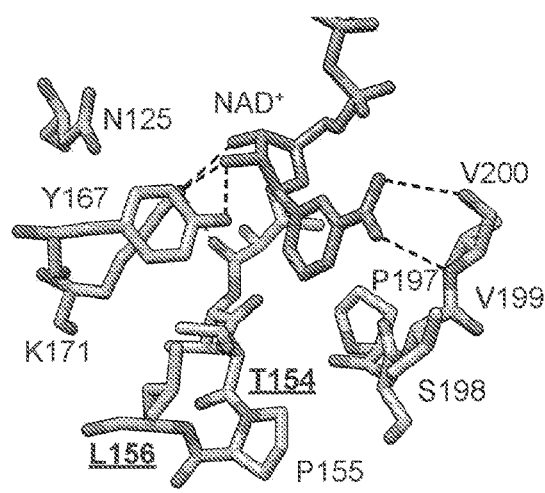
NEPS1
HM
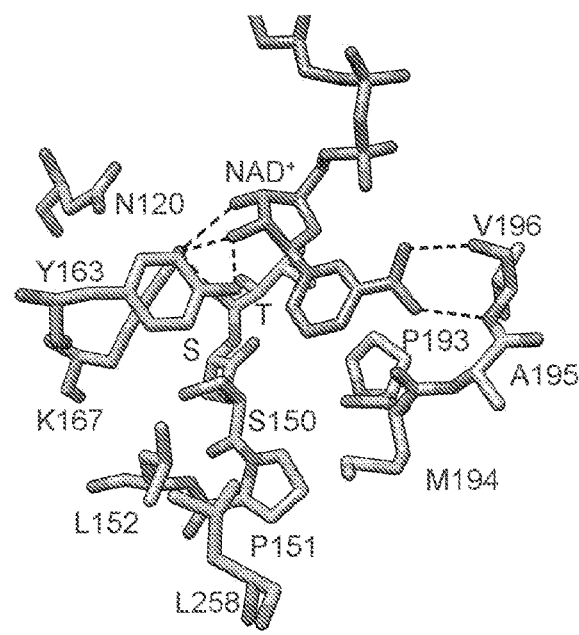
NEPS2
HM
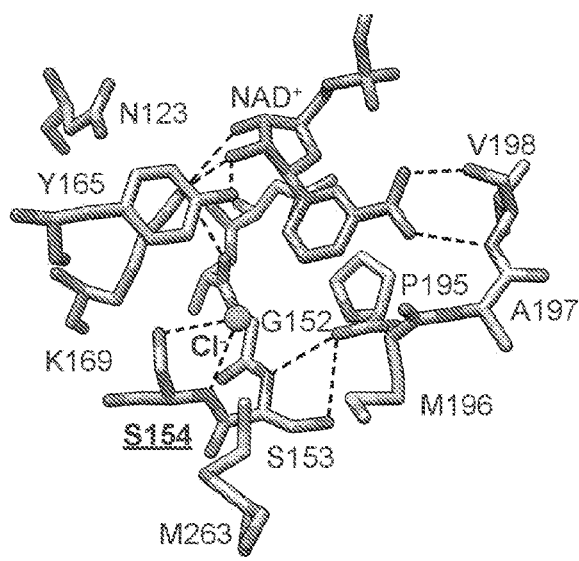
NEPS3
6F9Q

Fig. 7A
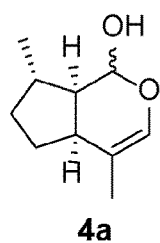
4a
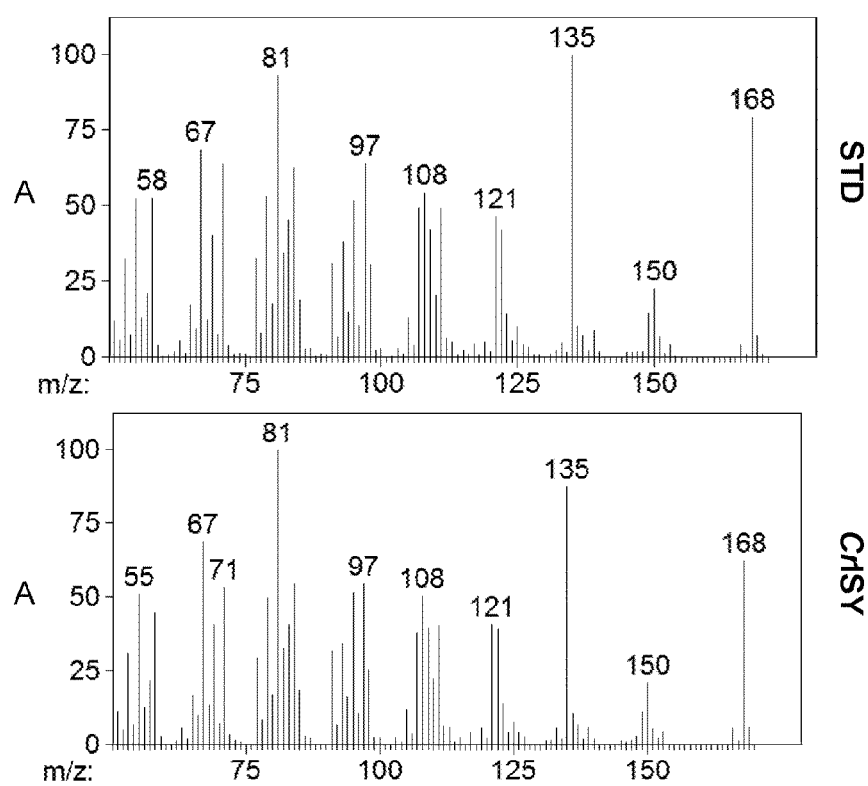
Fig. 7B
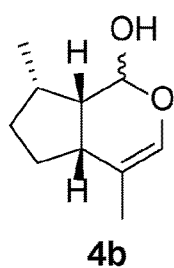
4b
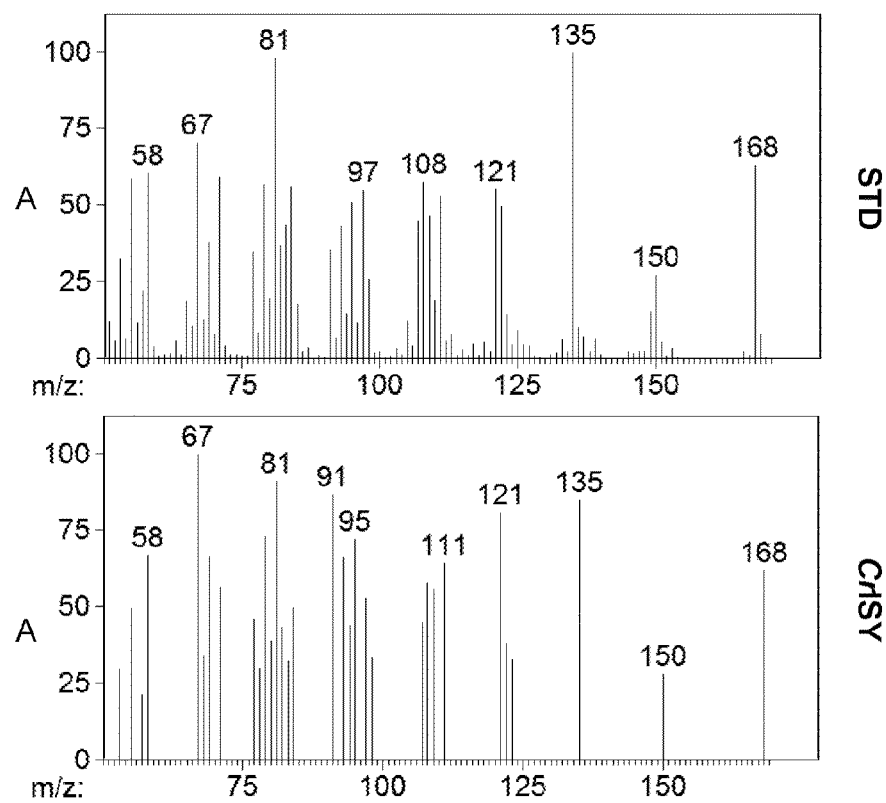

Fig. 7C
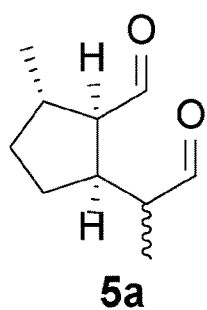
5a
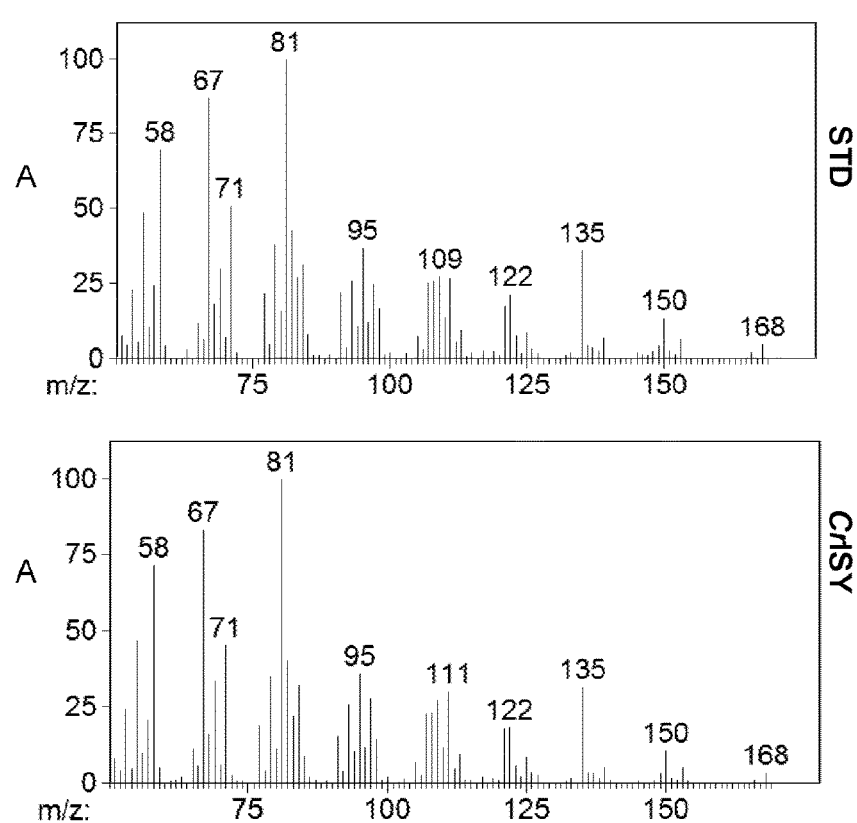
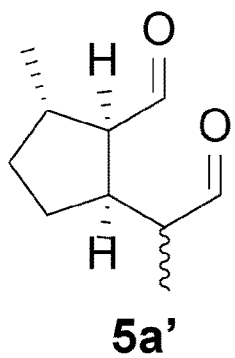
5a'
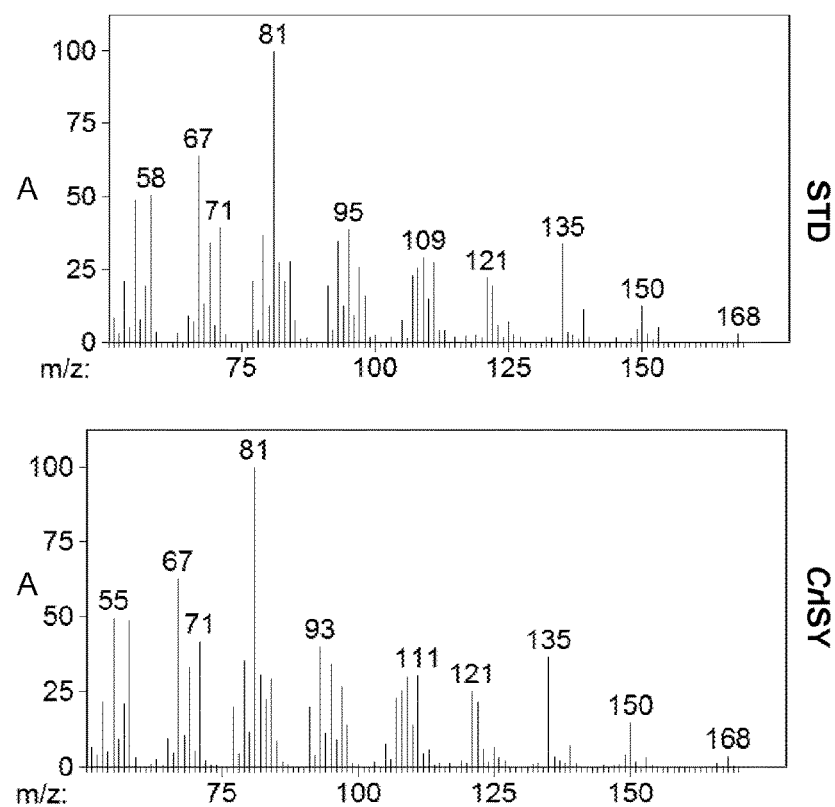

Fig. 7D
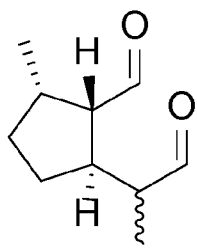
5c
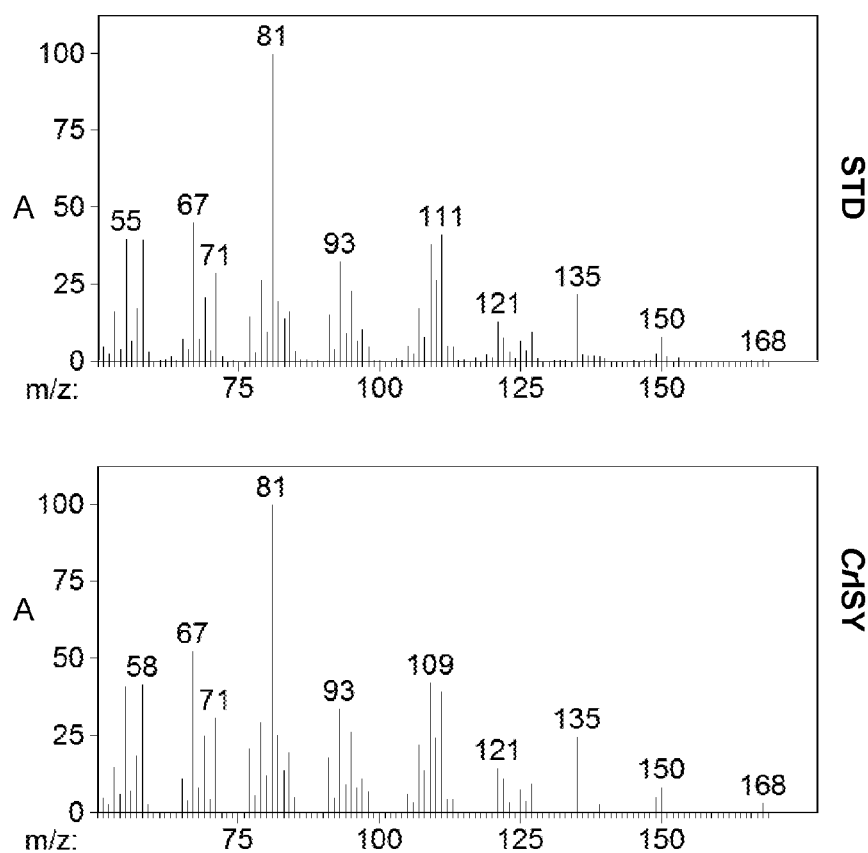
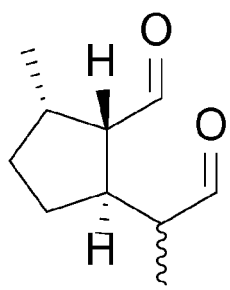
5c'
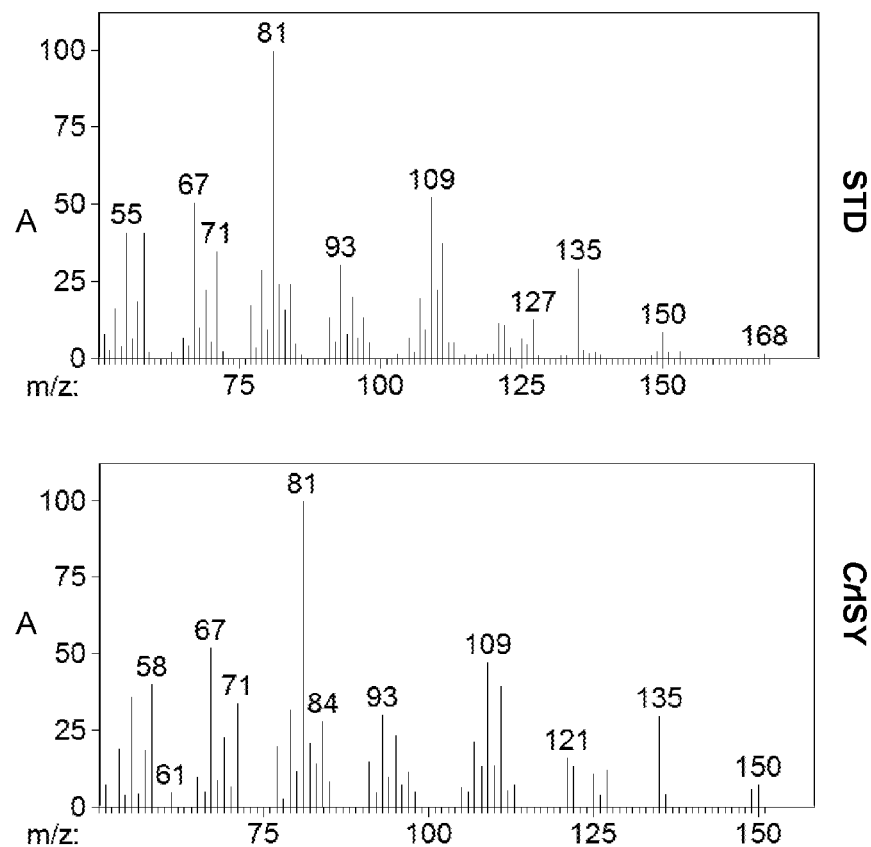

Fig. 7E
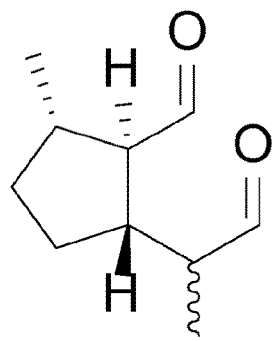
5d
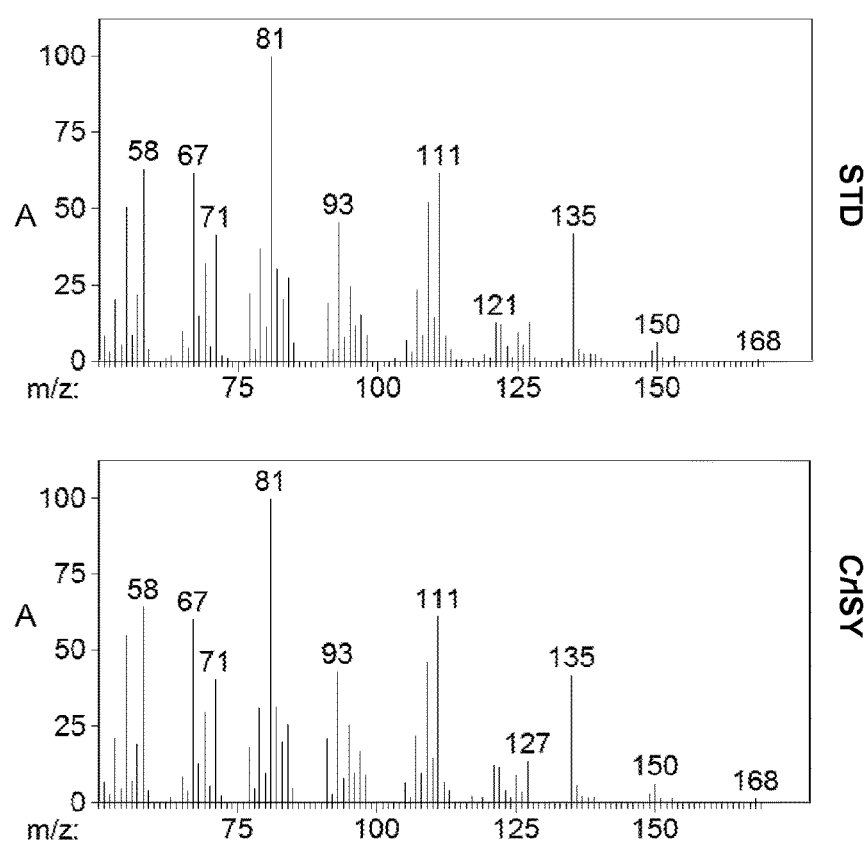
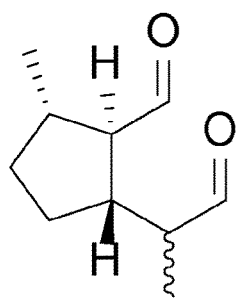
5d'
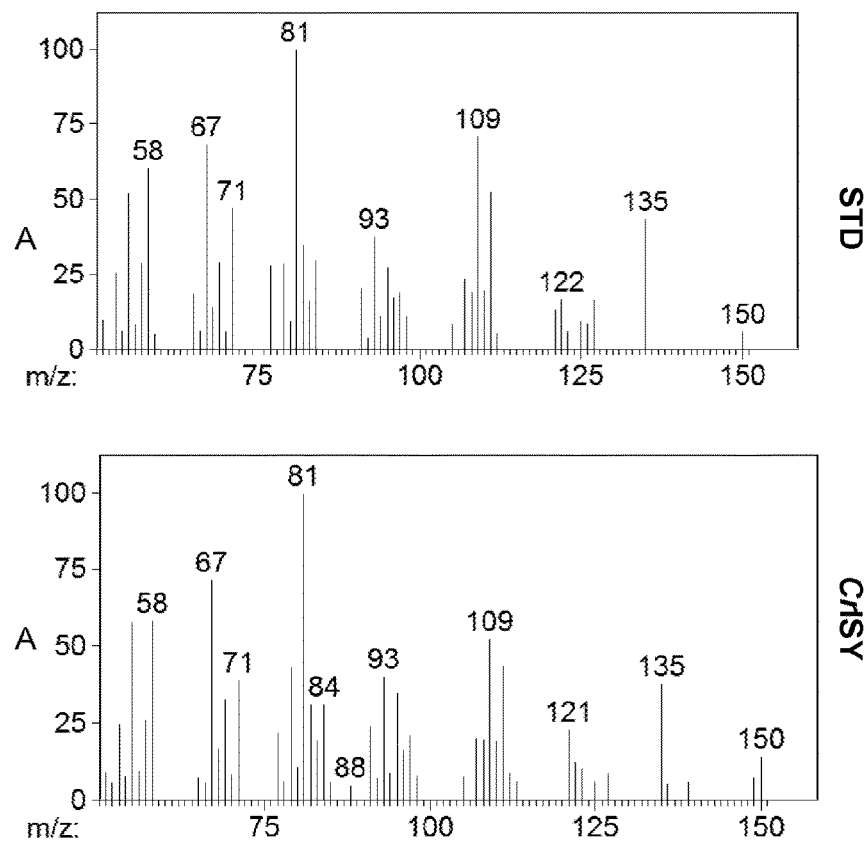

Fig. 9A
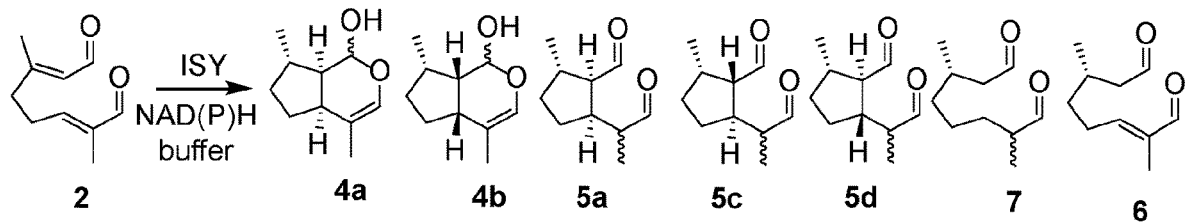
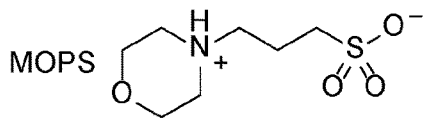
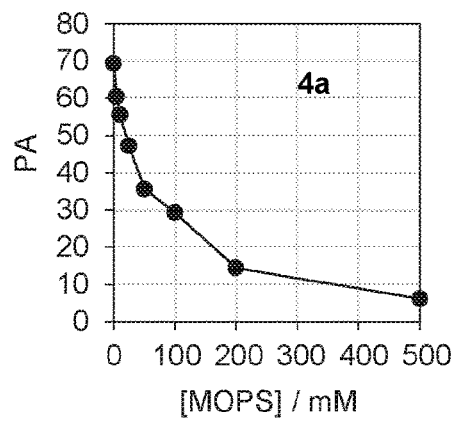
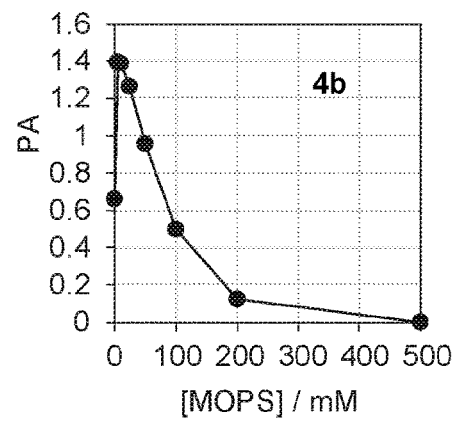
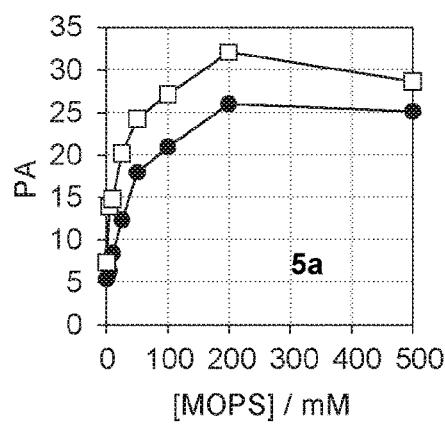
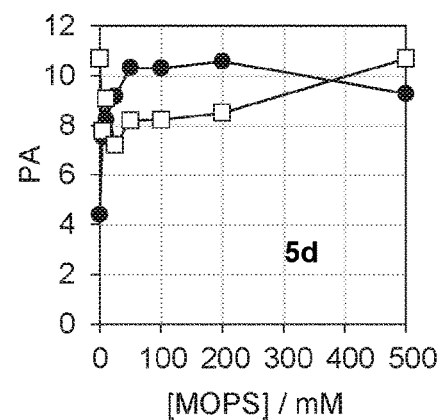
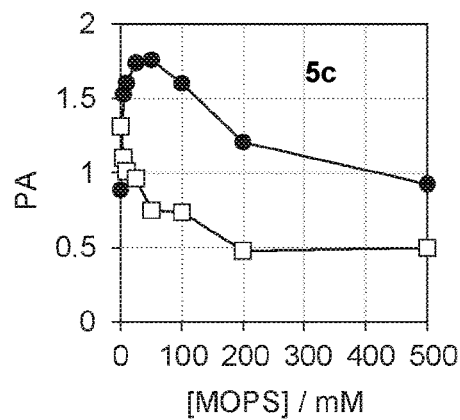
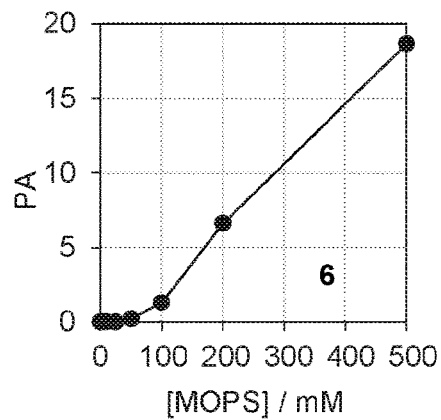

Fig. 9D
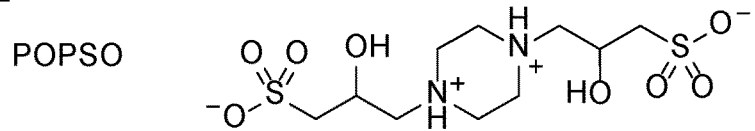
POPSO
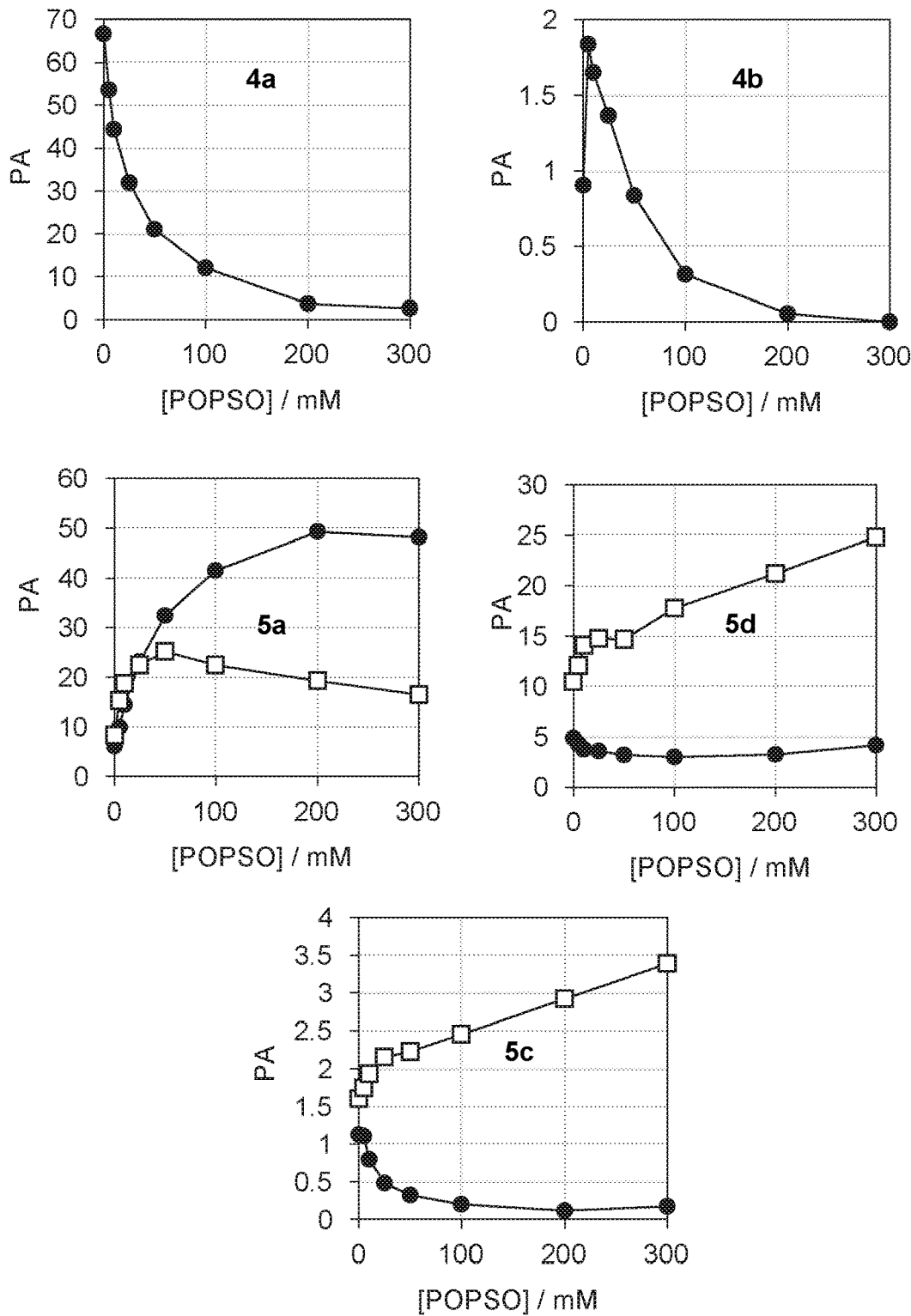

Fig. 12A
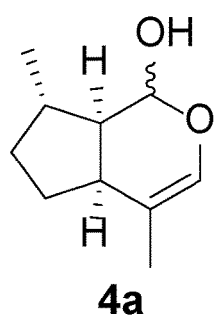
4a
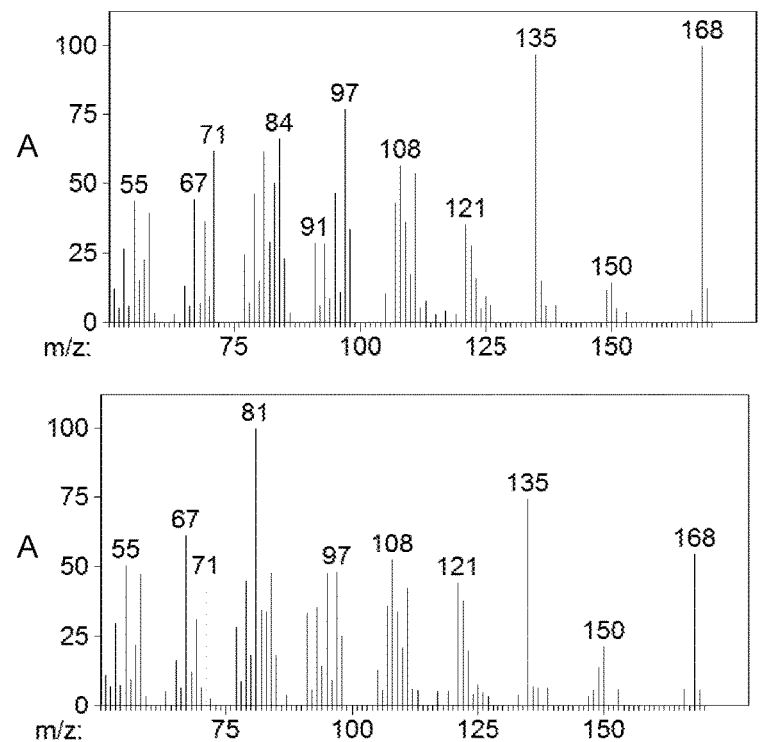
Fig. 12B
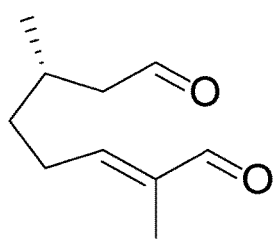
6
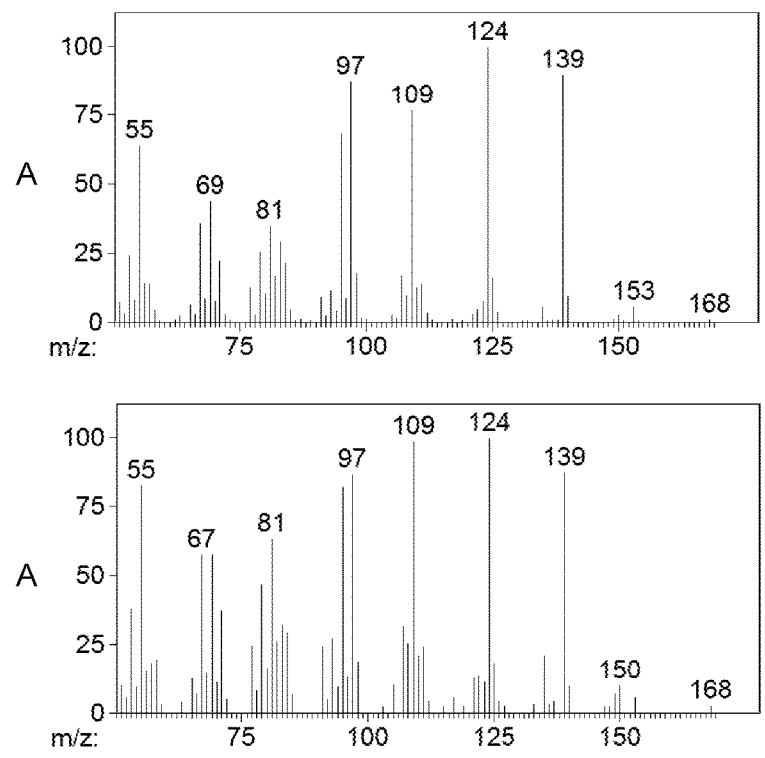

Fig. 12C
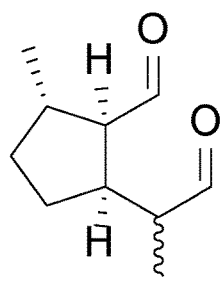
5a
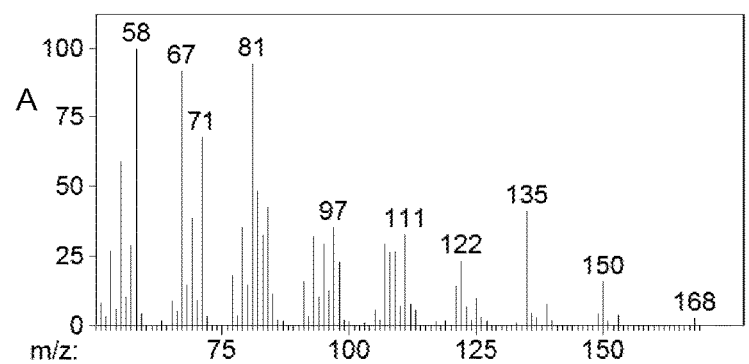
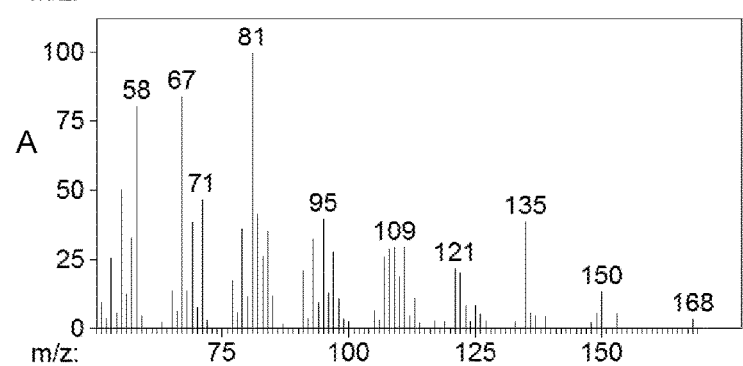
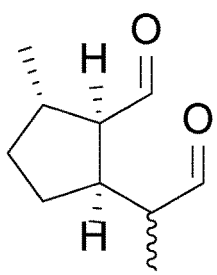
5a'
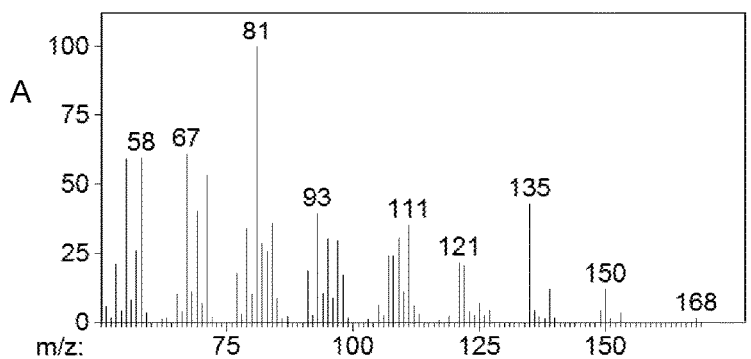
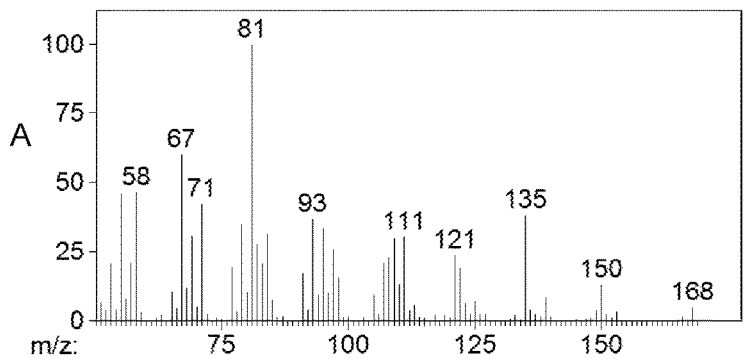

Fig. 12D
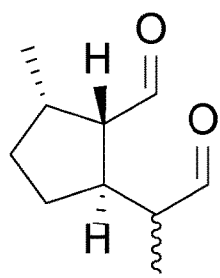
5c
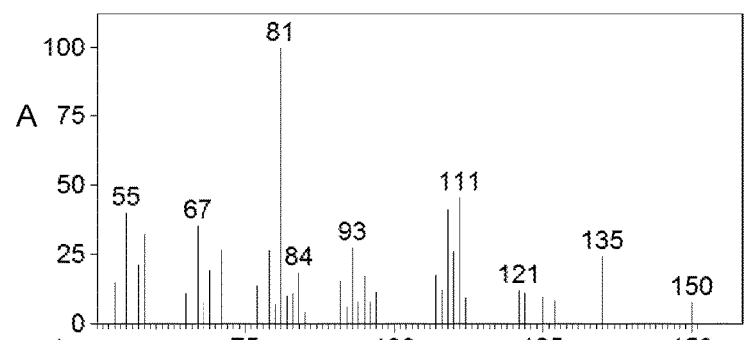
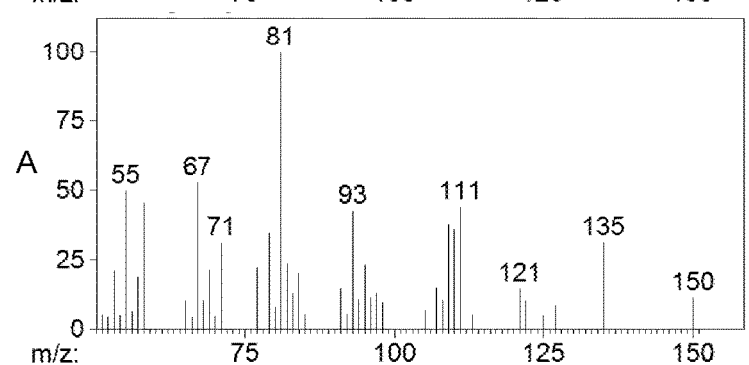
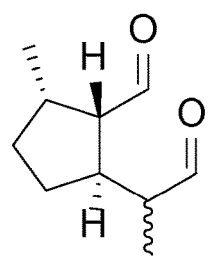
5c'
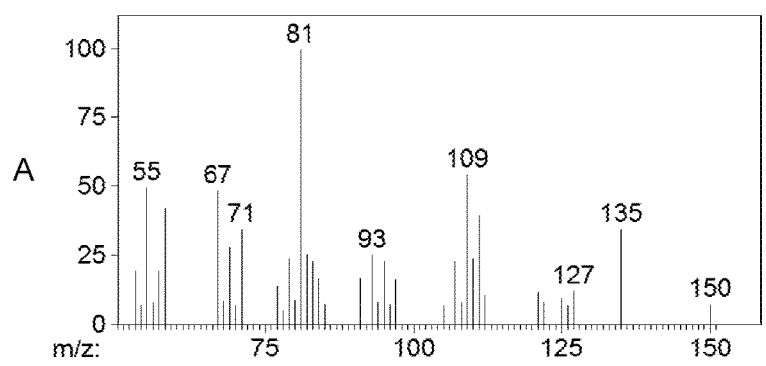
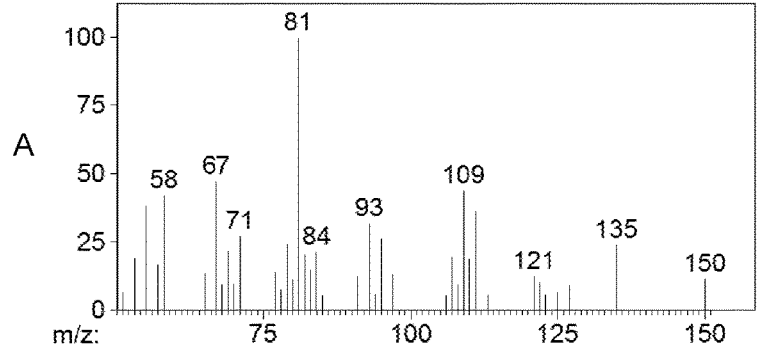

Fig. 12E
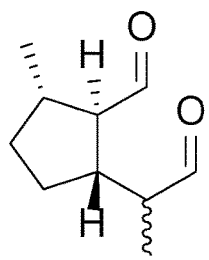
5d
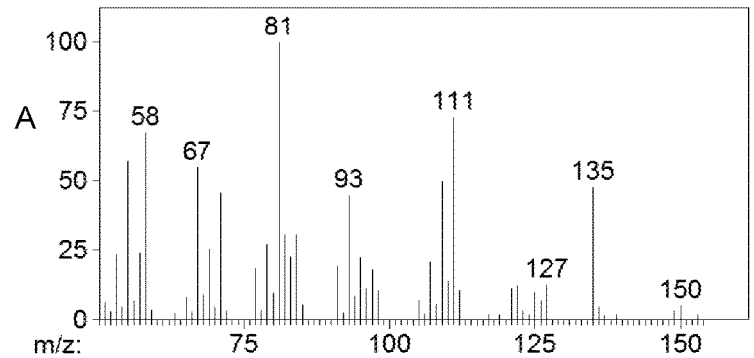
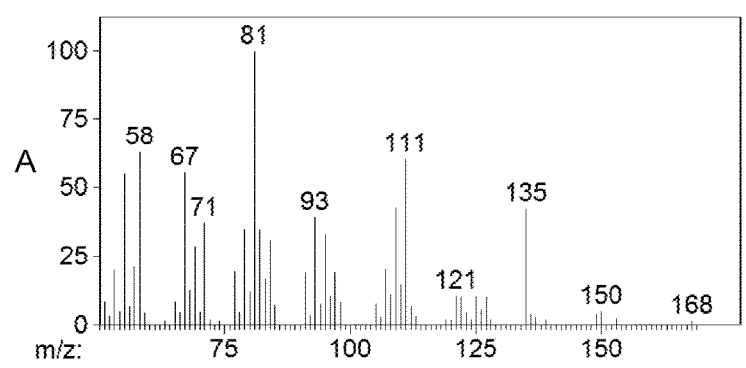
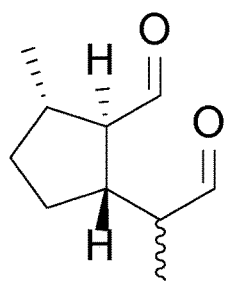
5d'
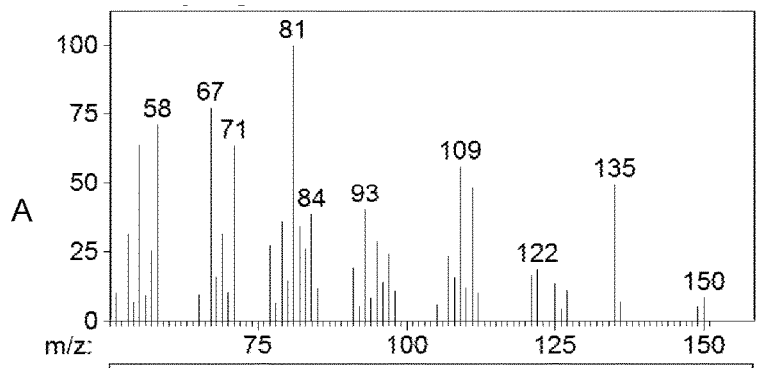
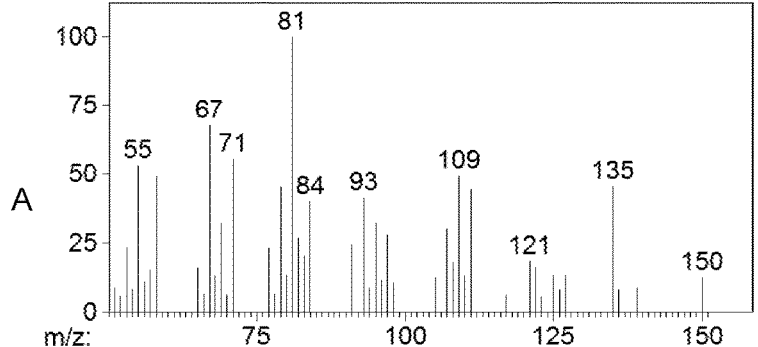

Fig. 12E
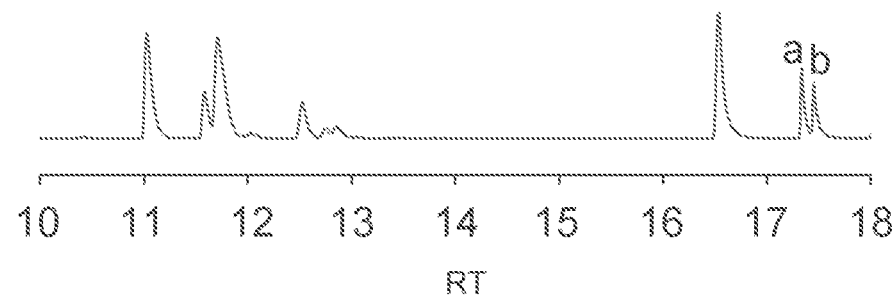
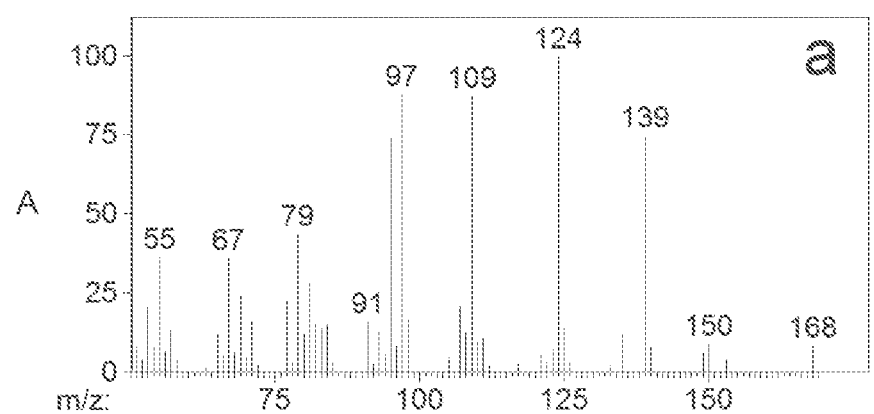
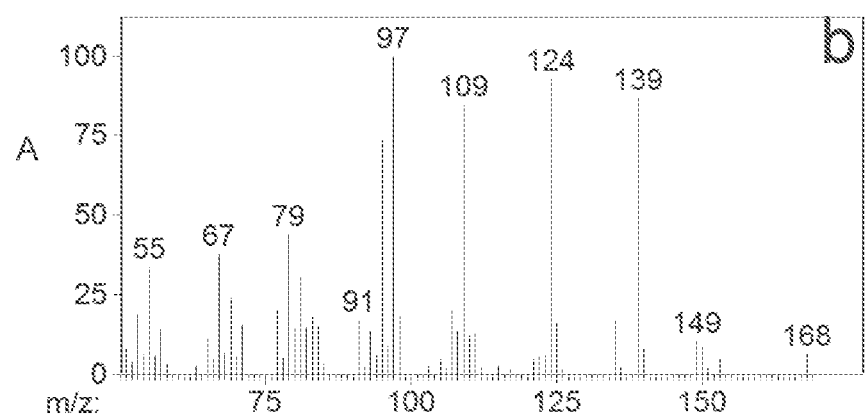

Fig. 14A
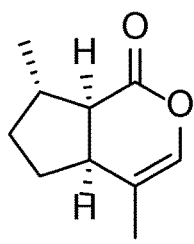
1a
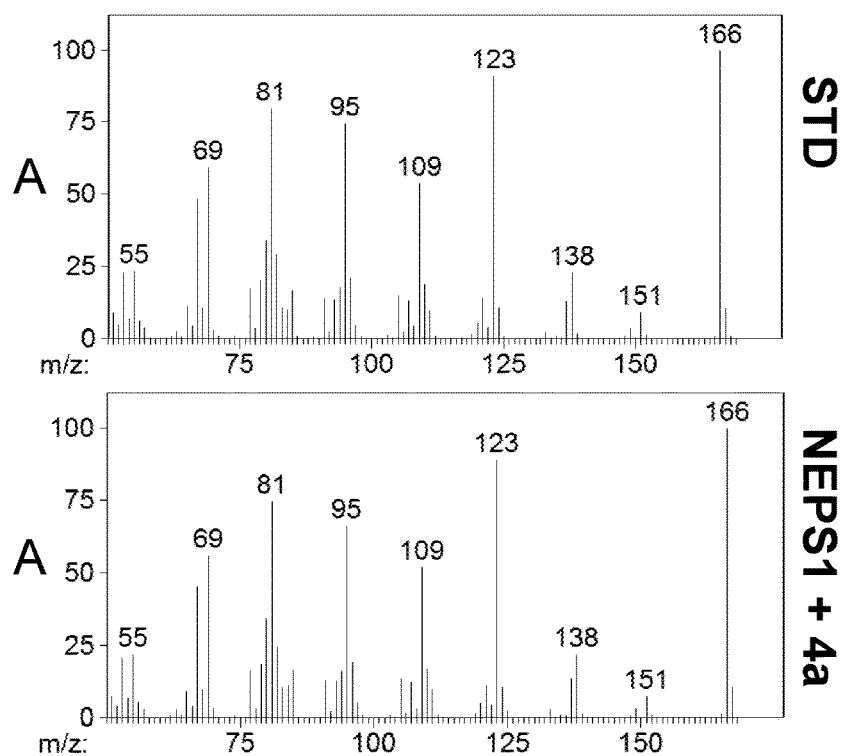
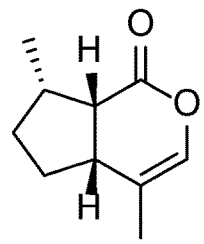
1b
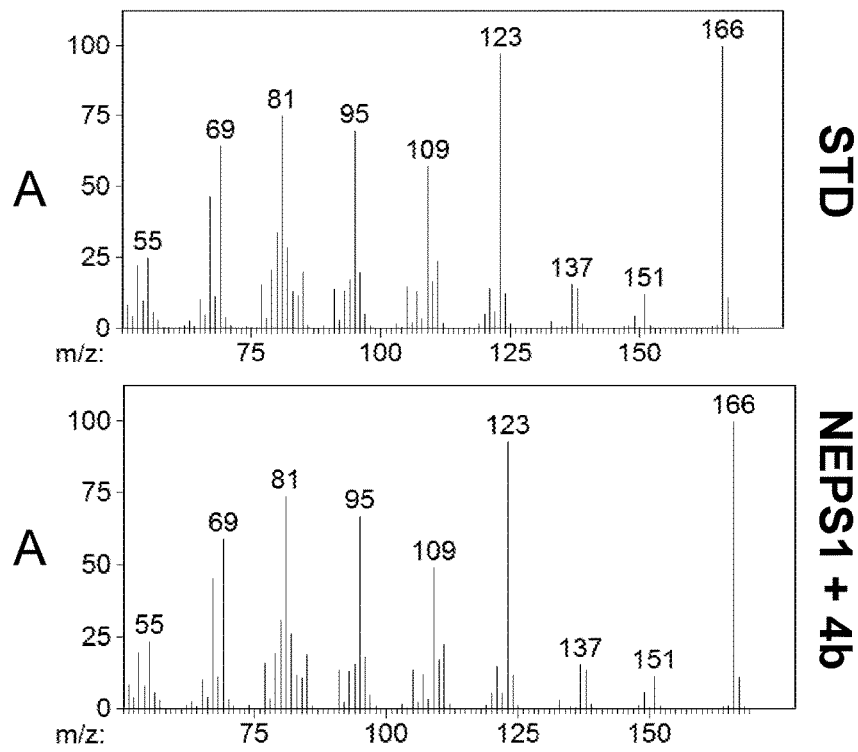

Fig. 14B
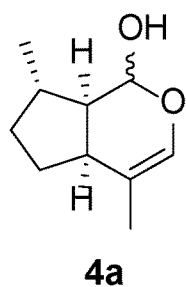
4a
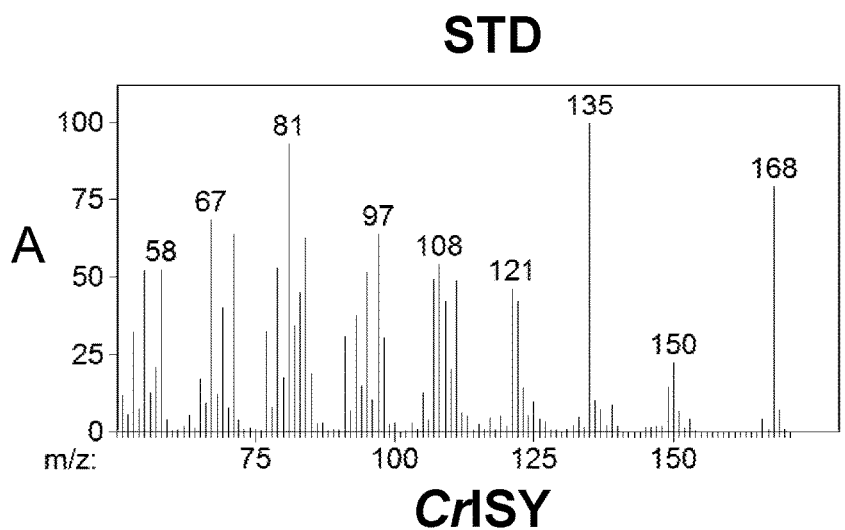
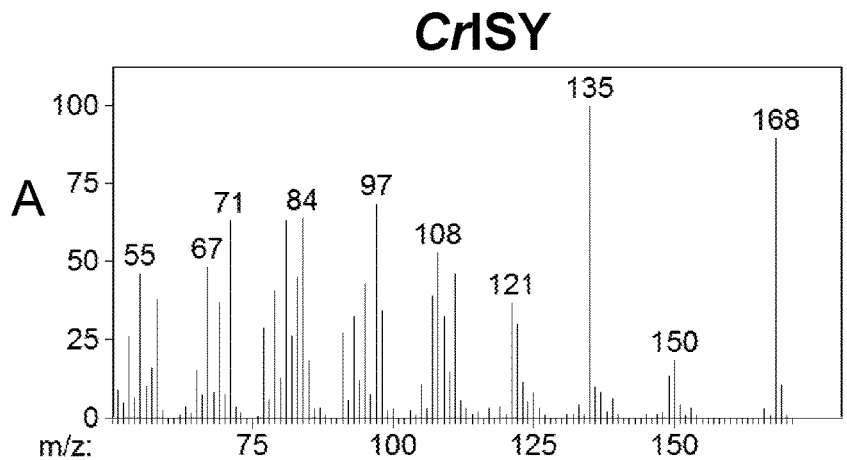
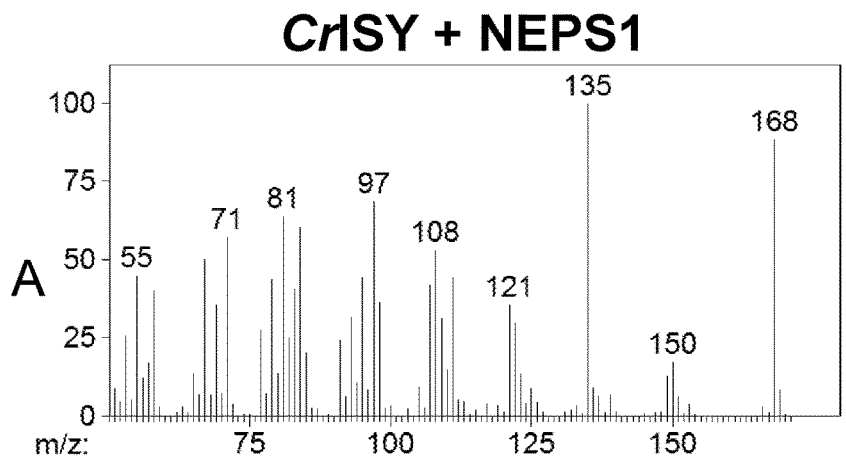

Fig. 14C
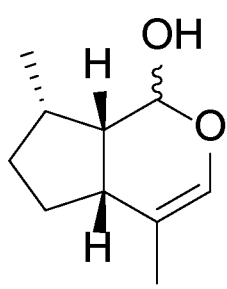
4b
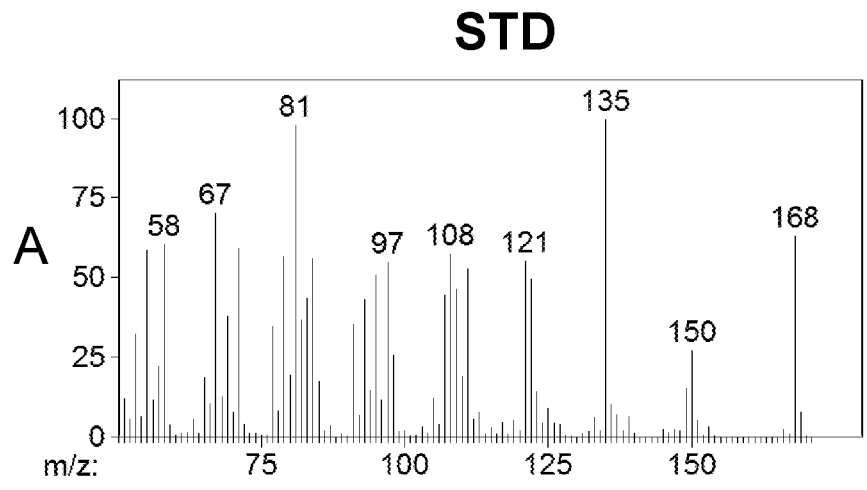
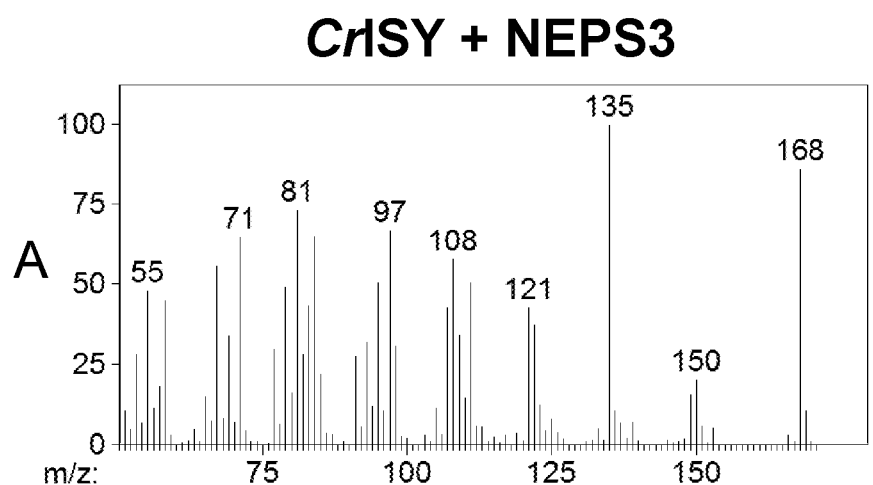
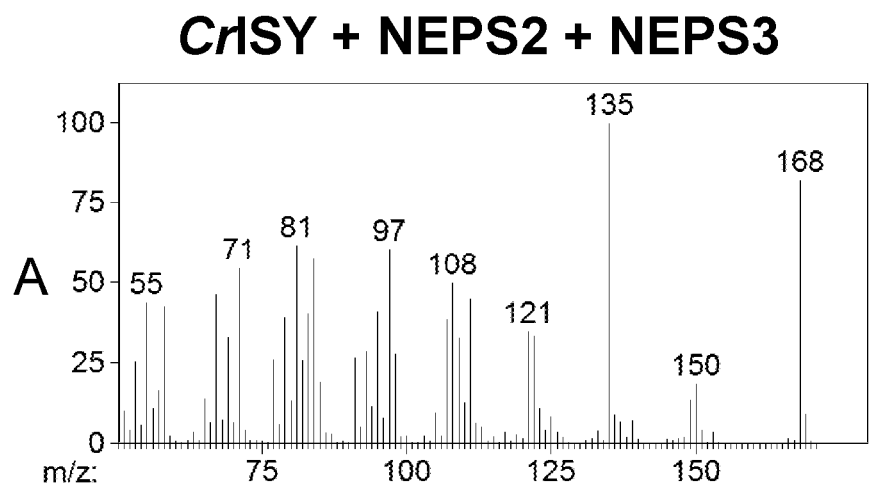

Fig. 15A

```
          1         10        20        30        40
A  MASTANPMQVMKKLEGKVVIVTGGASGIGQTAARVAQHGARAV
B  ........MGNKTIEGKVAIVTGGASGIGETAARVANLGARAV
C  ...MANNSVMMKKLEGKVAIVTGGASGIGEATPLVKYGARAV
D  ........MASVRKLAGKVAIVTGGASGIGEVTARLAERGARAV 50        60        70        80        90
A  VIADIQSVCKSVAKSIGDP.GCYQCDVSDEEVKMIERTSAVG
B  VIADIQSELREVAESIGAKRGSYQCDIGDEQVKMVELTATTG
C  VIADIQSLCRSVAESICKERGSFQCDVADEQVKMIELTATTG
D  VIADMQPKCGTVAESIGRRGSYHCDITDEQVRSVVDLTAATG 100       110       120       130
A  GLDMTSNVCIMS..KSADTVMDEDLLEEDKVMVNARCMAACLHA
B  ALVVTCNACIMSKAESQTVLEEDMSKDEVMRVNTRCTSAVVQA
C  GLDVTSNACVLN..SADTVKDEDLPLEDKVMVNTRCAAVGVQA
D  GVDVTCNACTAS..ATADTVLDEDLAQERVMRVNARCTAACVQA
                                         *

140       150       160       170       180
A  ARKMVELGTRG.TTITTTPLSSRGGQSMDYAMSHAVMGLVRS
B  ARKMVELGTKGAVTSSPLASRGGYIDDDVMSHAVMGLVRS
C  ARKMVELGRGG.SIINAGSSAVRGAHGVDVMSHAVIGLVRS
D  ARKMVELGRGG.AITASATVHAGPNLDYIMSKCGVLGLVRS
                *  o                  *    *

190       200       210       220       230
A  ASIQCAGTRVNCVTPSVVLPAQRMALAPDDFHTHFGNFTSKGVY
B  AMGEAGTRVNSVSPMAVLPTRRMALAPAVENAFGRFTSKGVA
C  AMGEASTRVNSVSPMAVAPTRNQISPDDVQKFLMPFISLKGP
D  ALGEVGTRVNSVSPTALAPTATIGLRAAVESFYGQVTSKGVA 240       250       260       270
A  LTPEQVAEAVVYLASDDAAFITGHDLVLDGGLLCLFFAPS.
B  LTAEHVAEAAFLASEEAAFITGHDMVDGGLLCLFFAPTS
C  PTAEQVAEAAFLGSDEAAFVLGHDLPVDGGVLCMPFLGSA
D  ITAEHVAEAVAFLASDEAARVLGHDLAVDGGLQCLPFVAVAK
```

A = NEPS1
B = NEPS2
C = NEPS3
D = MpIPDH

| % ID | NEPS1 | NEPS2 | NEPS3 | *Mp*IPDH |
|---|---|---|---|---|
| NEPS1 |  | 72 | 65 | 61 |
| NEPS2 | 72 |  | 71 | 70 |
| NEPS3 | 65 | 71 |  | 66 |
| *Mp*IPDH | 61 | 70 | 66 |  |

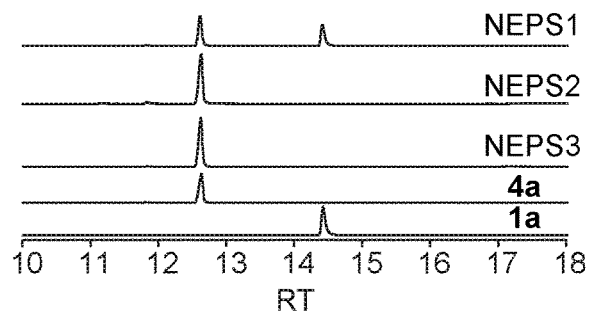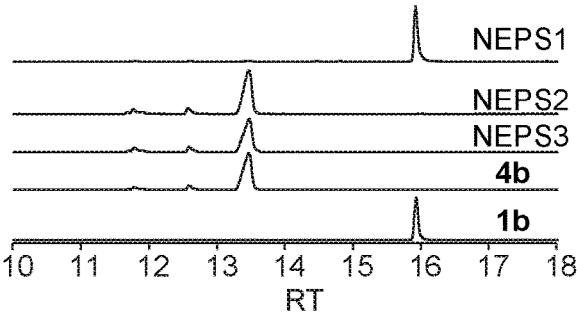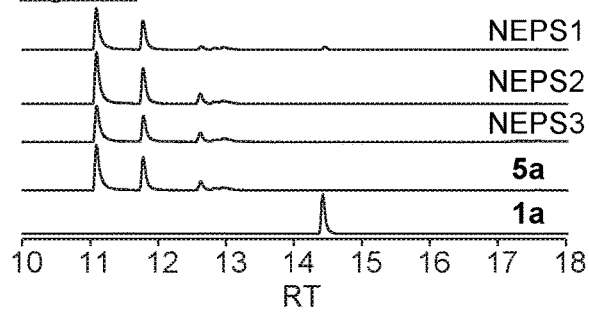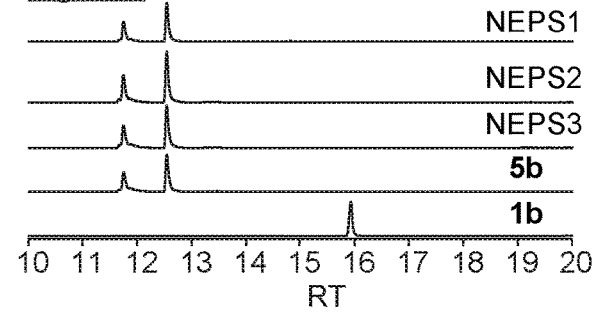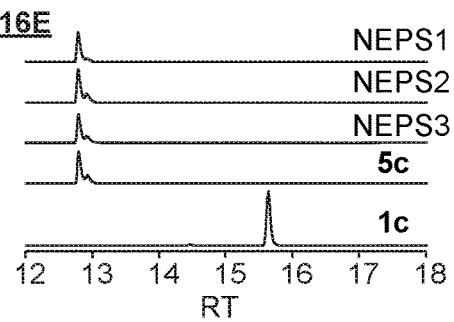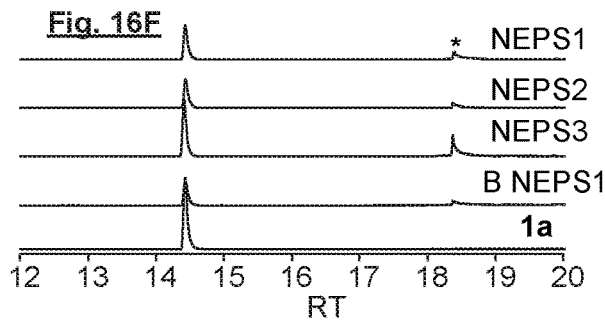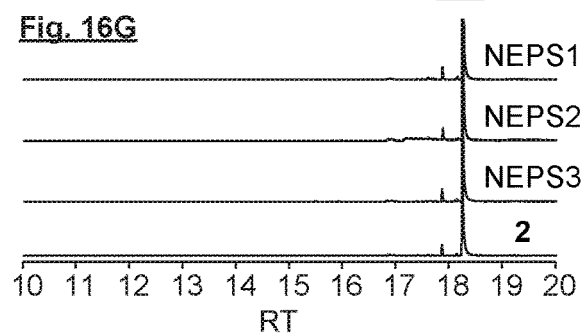

Fig. 17
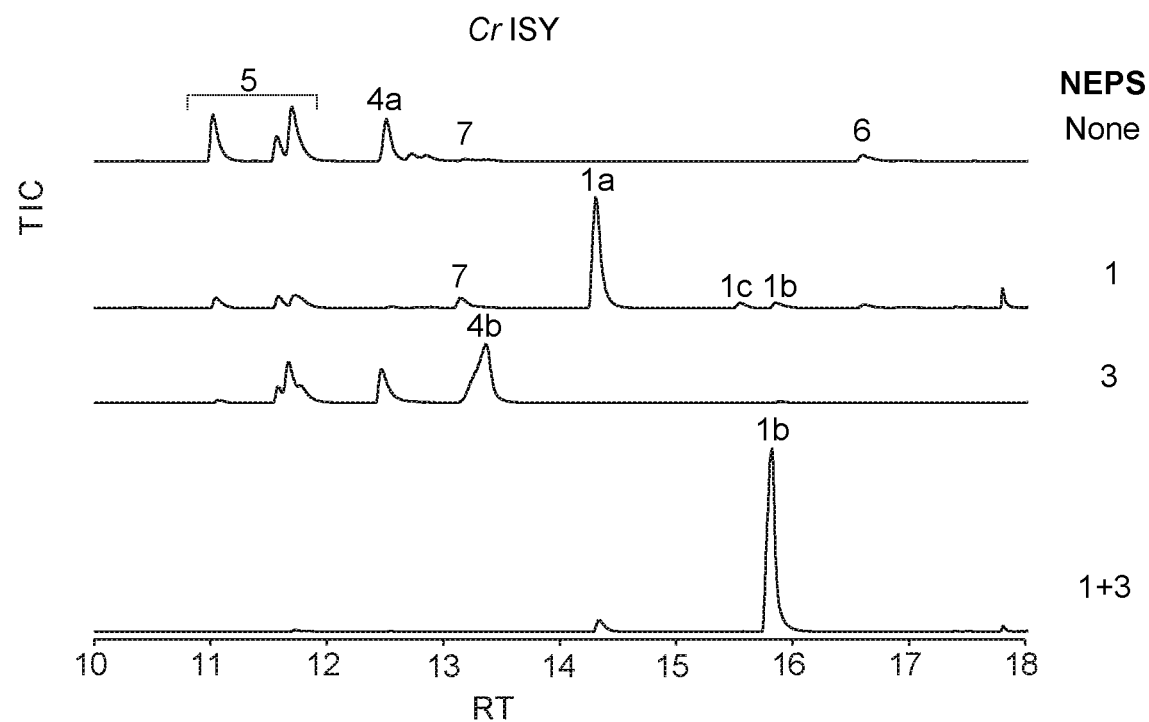
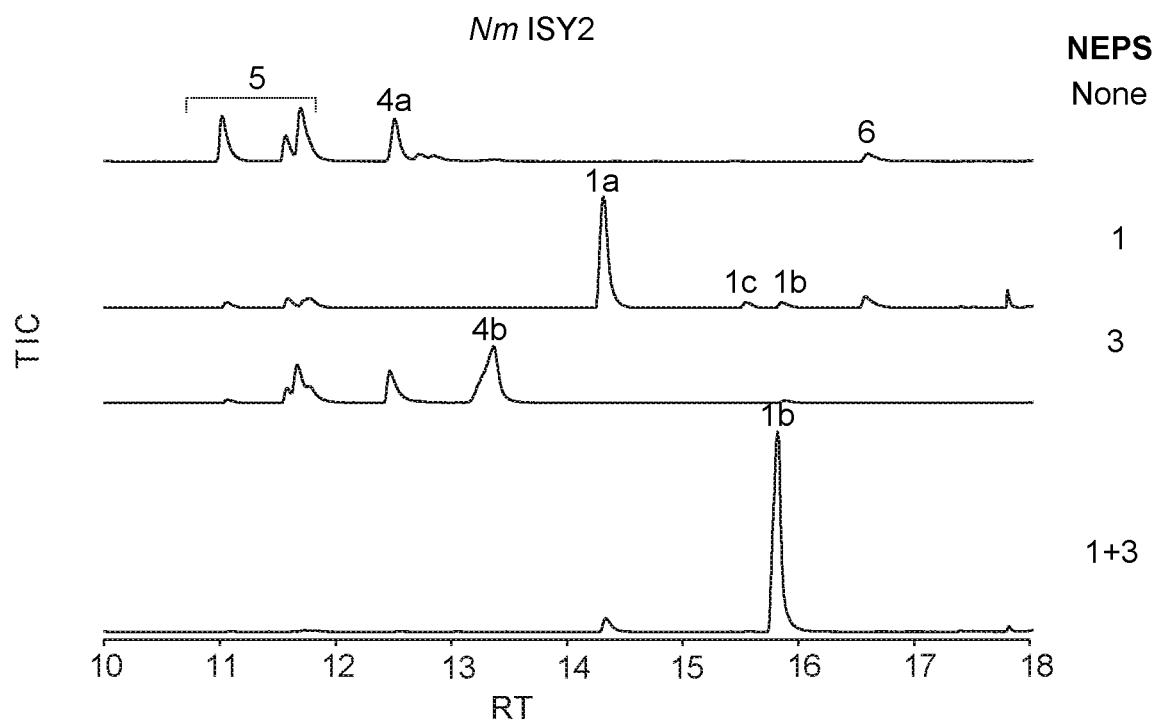

Fig. 18A
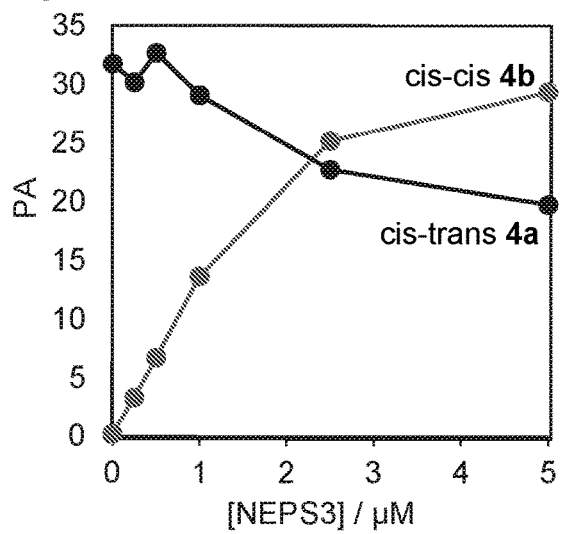
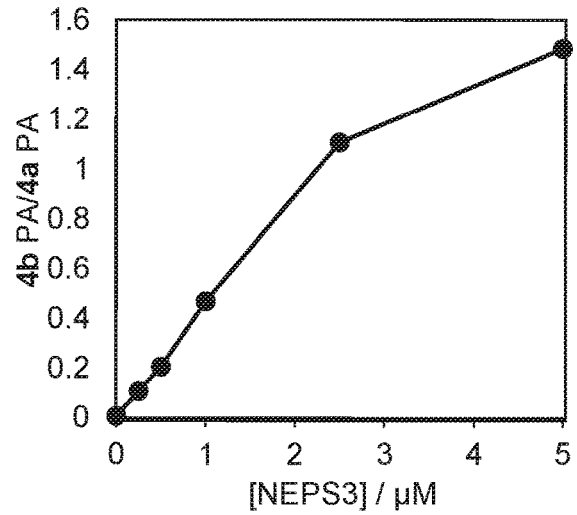
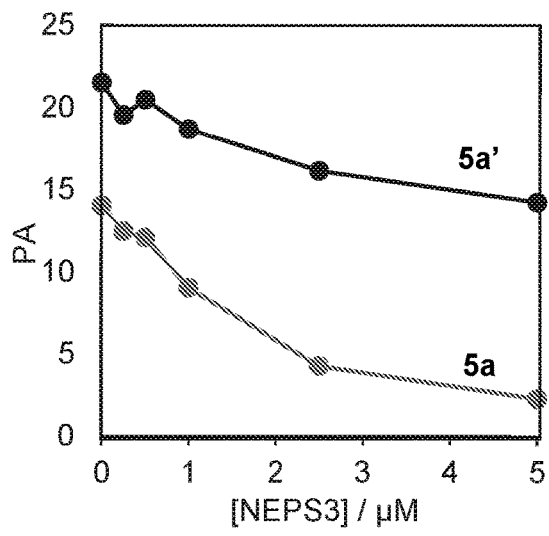
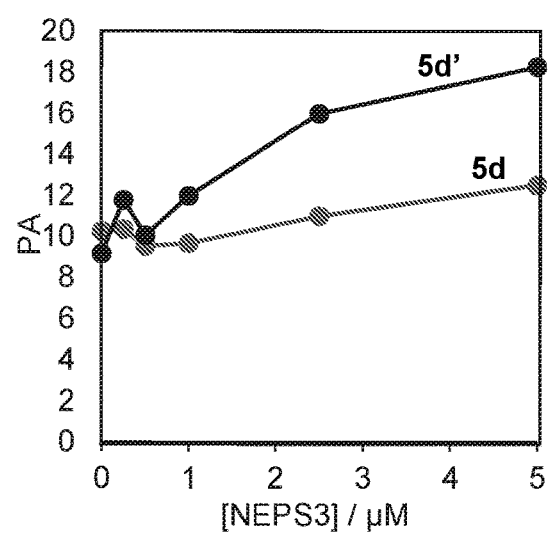
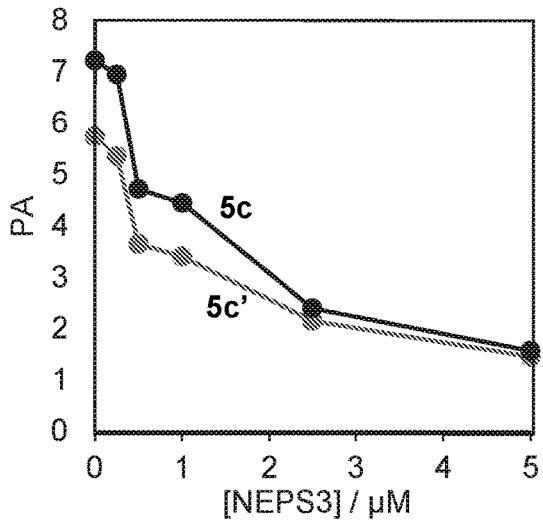
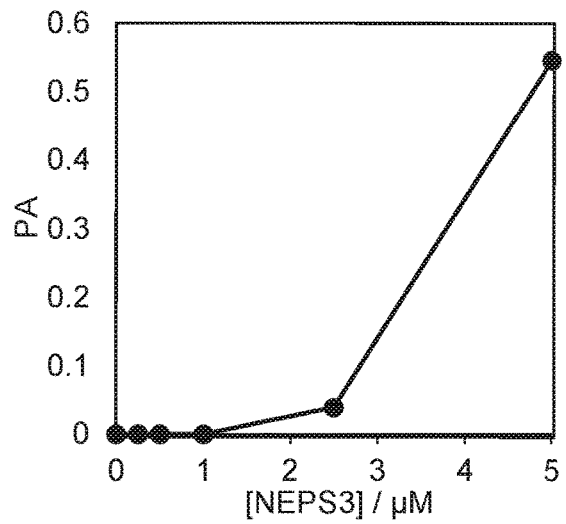

Fig. 18B
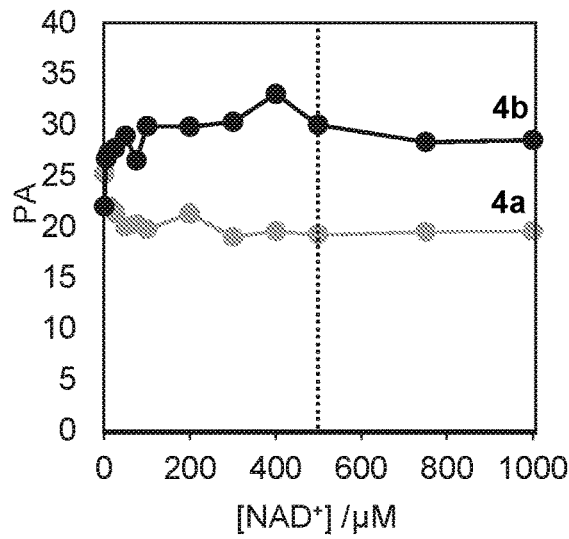
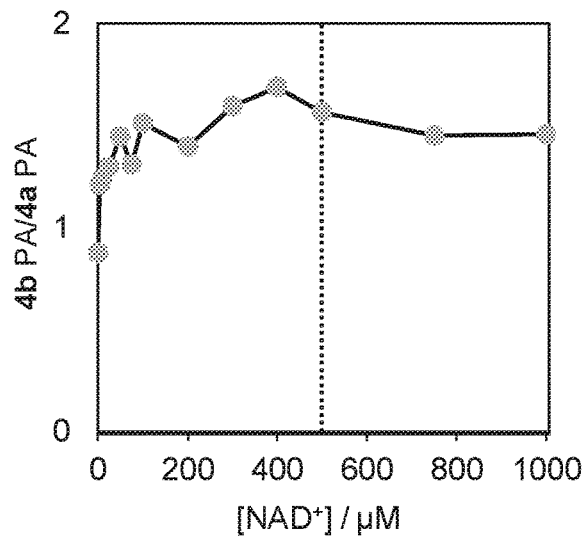
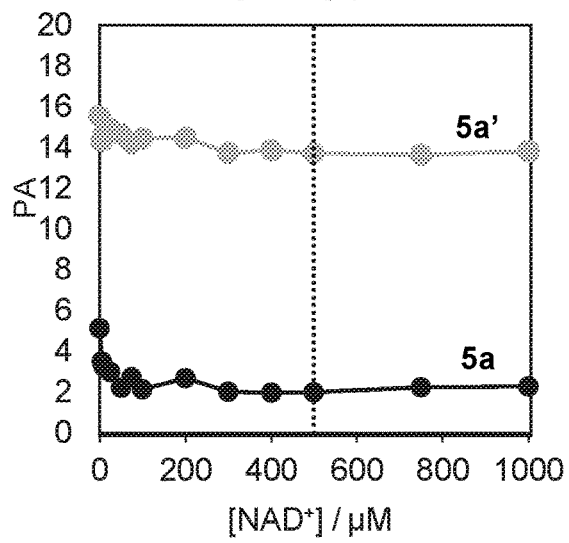
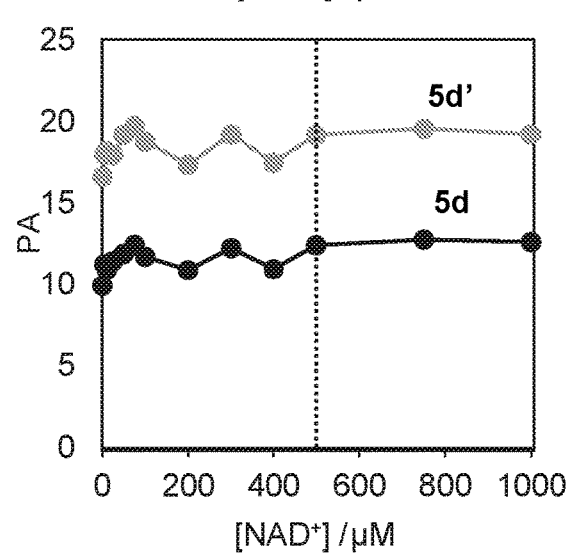
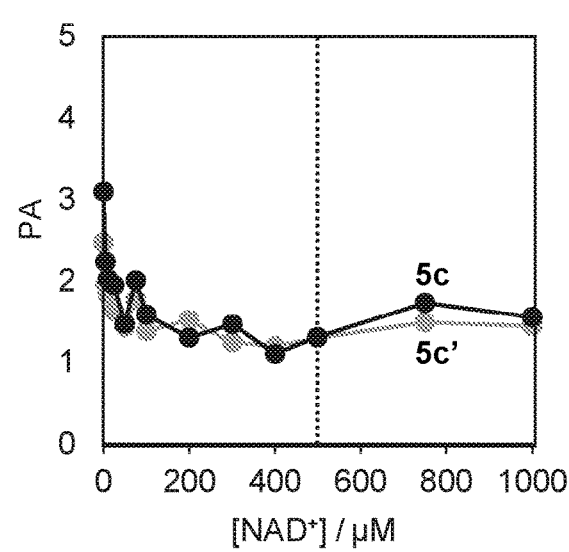
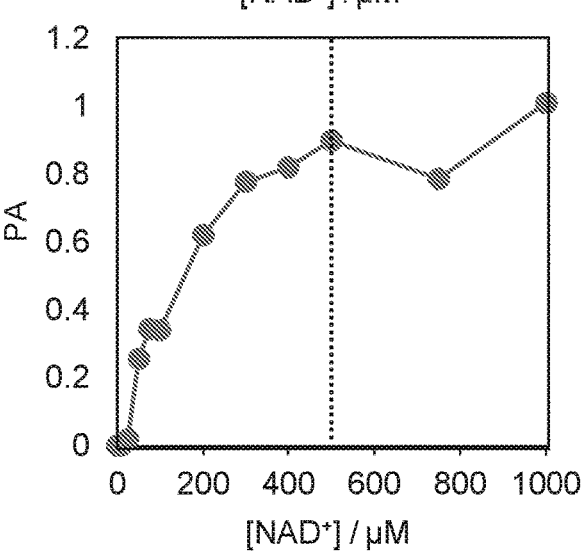

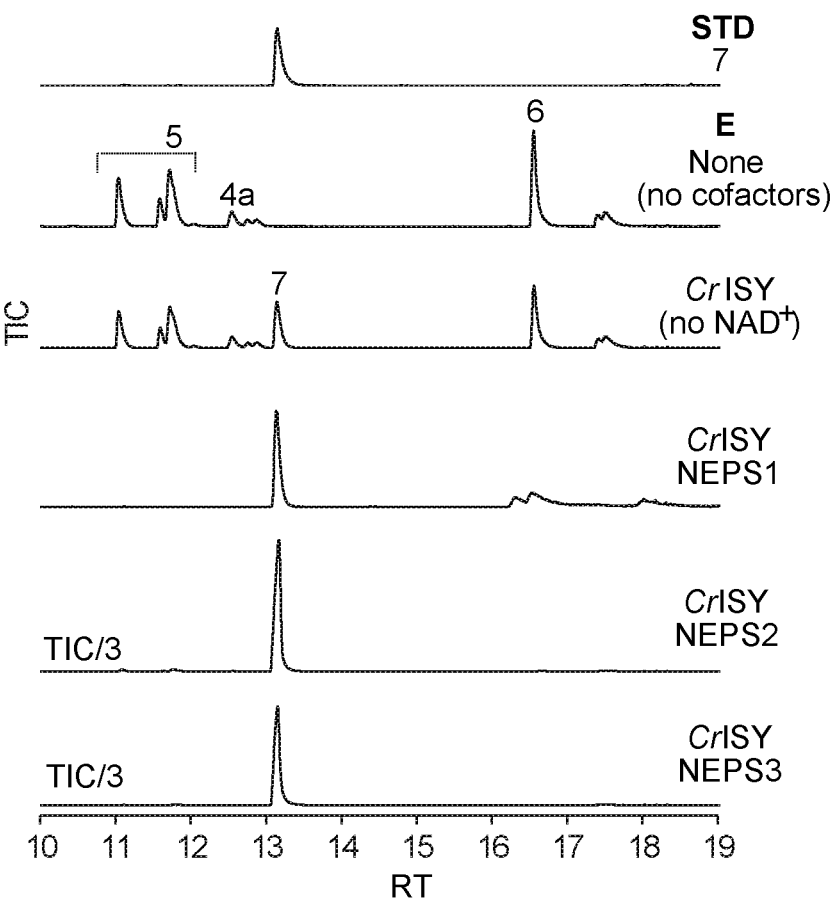

Fig. 20A
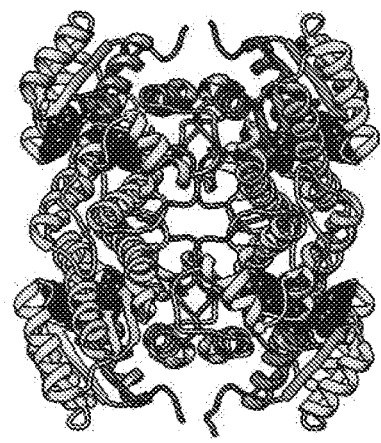
Fig. 20B
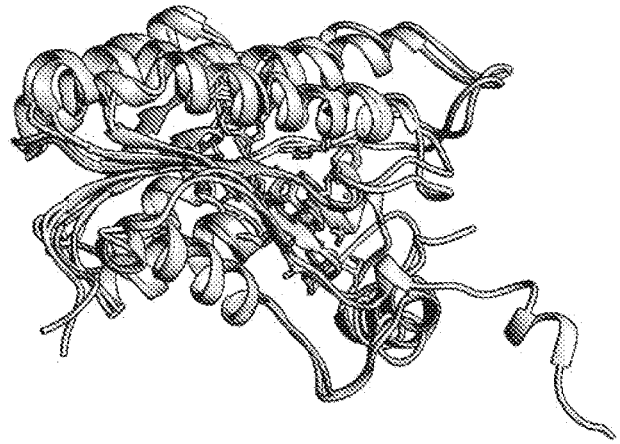
Fig. 20C
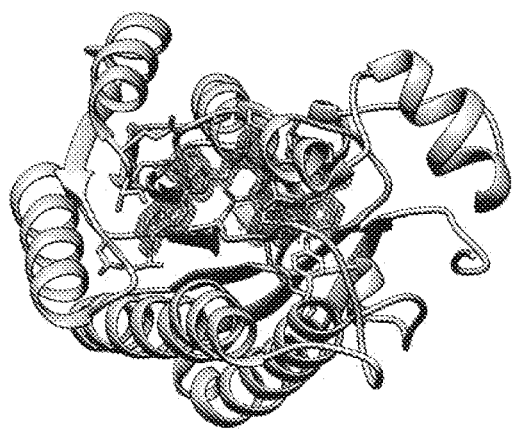
Fig. 20D
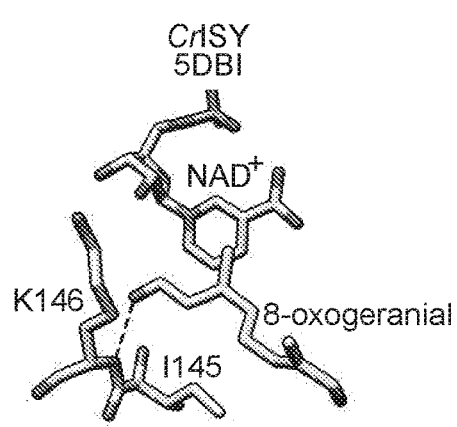
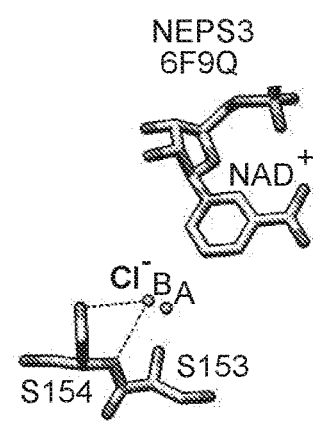

METHOD FOR PRODUCING MONOTERPENOID COMPOUNDS

FIELD OF THE INVENTION

The invention relates to enzymes and methods for producing a monoterpenoid compound.

INCORPORATION BY REFERENCE OF SEQUENCE LISTING

The Sequence Listing in an ASCII text file, named as 39033_Sequence_Listing.txt of 36 KB, created on Nov. 24, 2020, and submitted to the United States Patent and Trademark Office via EFS-Web, is incorporated herein by reference.

BACKGROUND OF THE INVENTION

Nepetalactones 1 are volatile natural products produced by plants of the genus *Nepeta*, notably catmint (*Nepeta mussinii* syn *racemosa*) and catnip (*N. cataria*) (FIG. 1A). These compounds are responsible for the stimulatory effects these plants have on cats. Moreover, certain insects use nepetalactones as sex pheromones, so production of these compounds by the plant also impacts interactions with insects. Notably, the bridgehead stereocentres (carbons 4a and 7a) vary between and within *Nepeta* species. *N. mussinii* individuals, for example, produce different ratios of cis-trans 1a, cis-cis 1b and trans-cis-nepetalactone 1c. Variation in stereoisomer ratio may influence the repellence of insect herbivores. While the ratio of stereoisomers may be responsible for important biological effects, the mechanism of stereocontrol in nepetalactone biosynthesis is not known.

Nepetalactones are iridoids, non-canonical monoterpenoids containing a cyclopentanopyran ring. Canonical cyclic terpenoids (e.g. (−)-limonene) are biosynthesised from linear precursors by terpene synthases (FIG. 1B). These enzymes activate linear precursors either by loss of pyrophosphate or protonation. The resulting carbocations generated cyclise rapidly to form an array of cyclic products. Therefore, in canonical terpenoid biosynthesis, activation and cyclisation of precursors are coupled and occur in the same enzyme active site.

In plant iridoid biosynthesis, geranyl pyrophosphate is hydrolysed and oxidised into 8-oxogeranial 2. This precursor then undergoes a two-step activation-cyclisation process, analogous to canonical terpene synthesis (FIG. 1C). Unlike canonical terpene synthesis, however, activation is achieved by reduction, and the intermediate is not a carbocation, but the enol or enolate species 3. Cyclisation of this intermediate yields cis-trans-nepetalactol 4a along with iridodial side products 5 (FIG. 1C).

The conversion of 2 to 4a and 5 is catalysed by iridoid synthase (ISY). ISY was first discovered in *Catharanthus roseus* (CrISY) where it forms part of the biosynthetic route to the anti-cancer monoterpene indole alkaloids vincristine and vinblastine. Subsequent studies revealed ISYs from Olive (*Olea europaea*, OeISY) and Snapdragon (*Antirrhinum majus*, AmISY), as well as paralogous proteins in *C. roseus* with promiscuous ISY activity.

The enzymatic control of the initial reductive activation step has been structurally characterised in CrISY: crystal structures with cofactor and inhibitor or substrate show binding modes conducive to reduction and formation of an enolate intermediate. Furthermore, this reduction is stereoselective, as exemplified by the comparison of CrISY, which produces 7S-4a, with AmISY, which produces the enantiomer.

In contrast, it is unknown how the cyclisation that determines the stereochemistry of the bridgehead 4a-7a-carbons of the iridoid scaffold to generate the stereochemical variation observed in *Nepeta*.

SUMMARY OF THE INVENTION

In a first aspect the invention relates to a method for producing a monoterpenoid compound, comprising:
(1) providing a monoterpenoid precursor;
(1) providing an enzyme; and
(1) contacting the monoterpenoid precursor with the enzyme under catalytic conditions to produce an monoterpenoid compound;
wherein the enzyme comprises an amino acid sequence comprising SEQ ID NO: 1 [NEPS1], and/or SEQ ID NO: 2 [NEPS2], and/or SEQ ID NO: 3 [NEPS3], or a functional variant or homologue of any of the enzymes.

Further aspects and features of the invention are set out in the appended claims and described further below.

The present invention is based on the discovery of the biosynthetic route to two nepetalactone stereoisomers in *N. mussinii*, cis-trans 1a and cis-cis 1b. The discovery of these genes reveals that the reduction and cyclisation steps of iridoid biosynthesis in *Nepeta* are uncoupled and catalysed by distinct enzymes (FIG. 1D). This process involves the diffusion of the activated intermediate 8-oxocitronellyl enol 3 between enzyme active sites, in contrast to canonical terpene biosynthesis, where generation of the activated intermediate and cyclisation occur in the same enzyme active site. We have discovered and characterised three cyclases (also referred to herein as NEPS1-3) from *N. mussinii* that are responsible for the stereoselective cyclisation and subsequent oxidation of activated intermediate 3 into distinct nepetalactone diastereomers. We have also determined the crystal structure NEPS3, providing insight into its mechanism and evolution from a reductase into a redox-neutral cyclase.

Figure 1A:
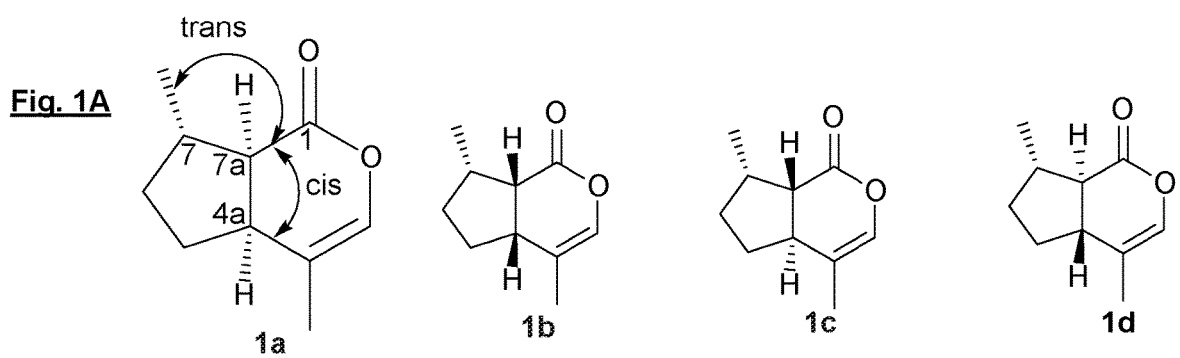
FIG. 1. Nepetalactones and terpenoid biosynthesis.

A, Nepetalactone 1 stereoisomers observed in *Nepeta* species (1a=cis-trans-nepetalactone, 1b=cis-cis-nepetalactone, 1c=trans-cis-nepetalactone), 1d=trans-trans-nepetalactone.

B, Representative canonical (mono)terpene biosynthesis mechanism. Typical terpene synthases (TS) activate linear precursors by removal of diphosphate or protonation (A=activation). The activated carbocation intermediates undergo selective cyclisation inside the same terpene (C=cyclisation) synthase active site. Limonene synthase is depicted as an example.

C, Iridoid biosynthesis mechanism. Iridoid synthase (ISY) activates (A) its linear precursor (8-oxogeranial 2) by reduction to form the 8-oxocitronellyl enol/enolate intermediate 3. This then undergoes cyclisation (C) to form a mixture of cis-trans-nepetalactol 4a and iridodials 5.

D, This work: nepetalactone biosynthesis in *Nepeta*. Biosynthetic origin of cis-trans and cis-cis-nepetalactone stereoisomers in *Nepeta* as reported in this paper (R=reduction, T=tautomerisation, C=cyclisation, O=oxidation, GA=general acid, 4b=cis-cis-nepetalactol, 6=8-oxocitronellal).

FIG. 2: Iridoid synthase (ISY) reaction mechanism.

A, Product mixture observed in the ISY catalysed reductive cyclisation of 8-oxogeranial 2. Products: cis-trans-nepetalactol 4a, cis-cis-nepetalactol 4b, cis-trans-iridodial 5a, trans-cis-iridodial 5c, trans-trans-iridodial 5d, tetrahydro-8-oxogeranial 7 and S-8-oxocitronellal 6.

B, 8-oxogeranial 2 reduction catalysed by ISYs from *Antirrhinum majus* (AmISY), *Catharanthus roseus* (CrISY) and *N. mussinii* (NmISY2). The enzymes form nearly identical product mixtures despite their evolutionary distance and sequence identity. * AmISY produces the opposite enantiomeric series to that depicted in panel a. Reactions were incubated for 3 h. Conditions: 0.5 UM ISY, 0.5 mM 2, 1 mM NADPH, 0.1 M MOPS pH 7.5. See FIG. 7 for electron ionisation (EI) spectra for compound identification. STDS=standards, RT=retention time.

C, ISY catalysed reduction of 2 at different buffer concentrations. At low buffer concentrations, the main product is cis-trans-nepetalactol 4a. As buffer concentrations increase, higher quantities of cis-trans-iridodials 5a are observed. At high MOPS (buffer) concentrations (>100 mM) 8-oxocitronellal (6) becomes a major product. We propose ISY reduces 2 and then releases the activated 3 into the solvent, where cyclisation occurs. Buffer appears to act as a general acid catalyst (GA), promoting tautomerisation in place of cyclisation. At low general acid concentrations, cyclisation is favoured but at high general acid concentrations tautomerisation is promoted. Conditions: 0.5 mM 2, 0.5 M NmISY2, 1 mM NADPH, MOPS pH 7.5 (varying concentrations). Reactions were incubated for 3 h. RT=retention time. See FIGS. 8, 9 and 10 for further exploration of the solvent conditions.

D, General acid catalysed cyclisation of S-8-oxocitronellal 6. Non-enzymatic (NE) formation of 4a and 5 achieved via tautomerisation to 3 and spontaneous cyclisation catalysed by general acid (buffer, GA). The product profile at 0.5 M buffer mimics the equivalent ISY catalysed reduction, supporting a non-enzyme catalysed cyclisation. No enzyme (NE) conditions: MOPS pH 7.5 (varying concentration), 0.5 mM 6, incubation for 16 h. NmISY2 conditions: 0.5 μM NmISY2, 0.5 mM 2, 1 mM NADPH, 0.1 M MOPS pH 7.5. See FIG. 11 for reactions with 6 in acidic/alkaline unbuffered water and FIG. 12 for EI spectra. All reactions are presented as GC-MS total ion chromatograms (TICs). RT=retention time.

FIG. 3: Formation of nepetalactones by NEPS enzymes.

A, Summary of NEPS enzyme activities described in this figure. R=reduction, C=cyclisation, O=oxidation.

B, Cis-trans-nepetalactol dehydrogenase activity of NEPS1. NEPS1 catalyses the $NAD^+$-dependent dehydrogenation of cis-trans-nepetalactol 4a to cis-trans-nepetalactone 1a. Conditions: 0.5 mM 4a 0.5 μM NEPS1. 1 mM $NAD^+$, 50 mM HEPES PH 8, 0.1 M NaCl. RT=retention time, STDS=standards, B=boiled.

C, Cis-cis-nepetalactol dehydrogenase activity of NEPS1. NEPS1 catalyses the NAD+-dependent dehydrogenation of cis-cis-nepetalactol 4b to cis-trans-nepetalactone 1b. Conditions: 0.5 mM 4b 0.5 μM NEPS1. 1 mM $NAD^+$, 50 mM HEPES pH 8, 0.1 M NaCl.

D, Combined activities of ISY and NEPS enzymes. Incubation of 8-oxogeranial 2, CrISY, NEPS and cofactors enables the production of products (P) including these main bicyclic products (MBP): cis-trans-nepetalactol 4a (no NEPS or NEPS2), cis-trans-nepetalactone 1a (NEPS1), cis-cis-nepetalactol 4b (NEPS3) or cis-cis-nepetalactone 1b (NEPS1 and NEPS3). Conditions: 0.5 mM 2, 0.5 μM CrISY, 2 μM NEPS, 1 mM NADPH, 5 mM $NAD^+$, 0.1 M MOPS pH 7.5. See FIG. 17 for comparison of NEPS cascades with NmISY2 and CrISY. See FIG. 18 for further analysis of the NEPS3 cyclisation reaction. RT=retention time.

E, NEPS-catalysed formation of cis-trans-nepetalactol 4a. Adjusting the $NAD^+$ and/or NEPS concentrations reveals NEPS1 and NEPS2 can promote the formation of cis-trans-nepetalactol 4a. Conditions: 0.5 mM 2, 0.5 μM CrISY, NEPS1 or 2 (varied concentration), 1 mM NADPH, 0 or 5 mM $NAD^+$, 0.1 M MOPS pH 7.5.

All reactions were incubated for 3 h and are presented as GC-MS TICs. See FIG. 14 for EI spectra.

FIG. 4: NEPS activities explored with S-8-oxocitronellal 6.

A, Summary of NEPS enzyme activities described in this figure. T=tautomerisation, C=cyclisation, O=oxidation, GA=general acid (buffer).

B, NEPS activities with S-8-oxocitronellal 6, buffer and $NAD^+$, presented as GC-MS TICs. The panel largely recapitulates observations of FIG. 3B, but in the absence of ISY. Unknown side products are formed by NEPS1. Conditions: 0.5 mM 6, 2 μM NEPS, 5 mM $NAD^+$, 0.5 M MOPS pH 7.5. The experiment without NEPS did not contain $NAD^+$. See FIG. 19 for reactions with 6, NEPS and CrISY. P=products, MBP=main bicyclic products.

C, Buffer dependence of NEPS activity with S-8-oxocitronellal 6. In the absence of buffer, NEPS1 and NEPS3 have no detectable activity; addition of buffer reveals enzyme activities. Buffer-catalysed tautomerisation of 6 appears to be necessary for enzyme activity, supporting the hypothesis that the activated 8-oxocitronellyl enol 3 and not S-8-oxo-citronellal 6 is the key NEPS substrate. Conditions: 0.5 mM 6, 2 μM NEPS, 5 mM $NAD^+$, MOPS pH 7.5 (0.5M, or no buffer). P=products.

D, NEPS3 catalysed cyclisation to form cis-cis-nepetalactol 4b. The addition of NAD+ is not required for NEPS3 cyclisation activity, though addition does promote the reaction. We hypothesise that the cyclisation is not oxidoreductive, but NAD+ acts in a non-chemical manner (i.e. protein stabilisation). Conditions: 0.5 mM 6, 2 or 20 μM NEPS, 0 or 5 mM $NAD^+$, 0.5 M MOPS pH 7.5. All reactions analyses are presented as GC-MS TICs.

FIG. 5: Structure of NEPS enzymes.

X-ray crystal structure of NEPS3 (6F9Q) and homology model (HM, template 6F9Q) structures of NEPS1 and NEPS2. Active site $NAD^+$ and residues are depicted as sticks. Dashed lines represent proposed H-bonds. The NEPS3 active site lacks the characteristic Ser/Thr of the SDR catalytic tetrad (G152). It also features a chloride bound to S154 and H-bonding between S153 and P190, features absent from NEPS1 (L156) and NEPS2 (L152). The role of residues in bold and underlined have been analysed by mutation. See FIG. 20 for further analysis of the NEPS3 crystal structure.

FIG. 6: NEPS variants.

A, Coupled assay with 8-oxogeranial 2, ISY and NEPS variants, presented as GC-MS TICs. The product profile was measured after 3 h. The substitution S154L in NEPS3 appears to remove the cis-cis cyclase activity (absence of 4b), but with 10 μM enzyme the formation of cis-trans-nepetalactol 4a appears to be promoted relative to iridodials 5. The L156S substitution in NEPS1 largely removes dehydrogenase activity of NEPS1 (less cis-trans-nepetalactone 1a) but no increase in cis-cis-nepetalactol 4b is observed. Conditions: 0.5 mM 2, 0.5 μM CrISY, 2 or 10 μM NEPS, 1 mM NADPH, 5 mM $NAD^+$ and 0.1 M MOPS pH 7.5. SP=side products, RT=retention time.

B, Time course of coupled assay with 8-oxogeranial 2, ISY and NEPS1 WT or T154G. Quantities of cis-trans-nepetalactol 4a (open squares) and cis-trans-nepetalactone 1a (closed circles) measured over the course of the reaction. Product proportions described as GC-MS TIC peak areas as a percent proportion of total product peak area (PA). NEPS1-WT oxidises 4a into 1a rapidly whilst NEPS1-T154G oxidises 4a with less efficiency. See FIG. 22 for all TICs of time course, and Table 2 for kinetic analysis. T=time. Conditions: 0.5 mM 2, 0.5 μM CrISY, 2 μM NEPS, 1 mM NADPH, 1 mM NAD$^+$ and 0.1 M MOPS pH 7.5.

C, Putative binding mode of cis-trans-nepetalactol 4a in the NEPS1 active site. Binding mode generated by computational docking calculations using the NEPS1 homology model. The putative H-bond interaction between the lactol and T154 is highlighted with a dotted line. The depicted binding mode was ranked third of ten predicted binding modes (rank 1 score=−6.4 kcal·mol−1, depicted rank 3 energy=−6.3 kcal·mol−1).

D, Scheme of NEPS1 activities and interactions. NEPS1 appears to have two distinct activities—cyclisation and dehydrogenation. The behaviour of the mutant T154G suggests that T154 is involved in dehydrogenation. The two activities appear distinct and may even involve different active site interactions. The slightly improved cyclase activity of T154G may be due to poor binding of 4a which frees more enzyme for binding and cyclising 3 into 4a. SP=side products, S=solvent.

Figure 7F:
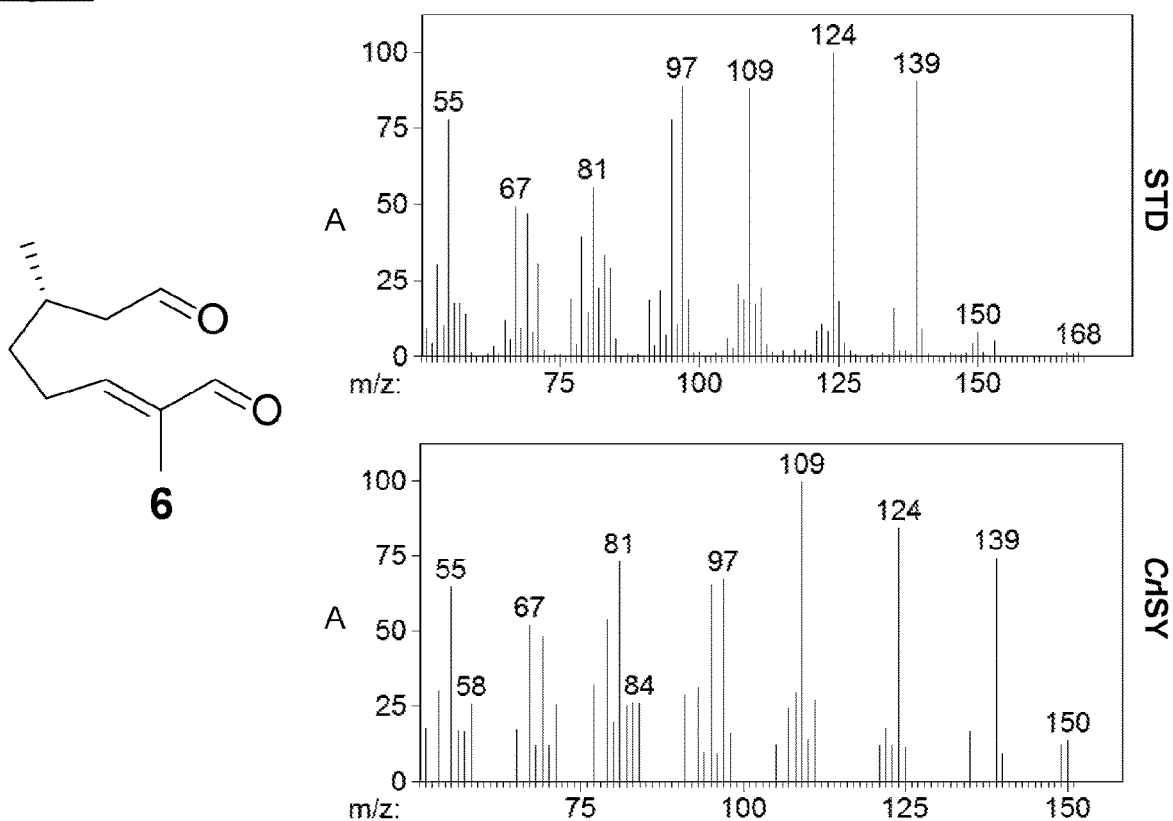
Figure 7G:
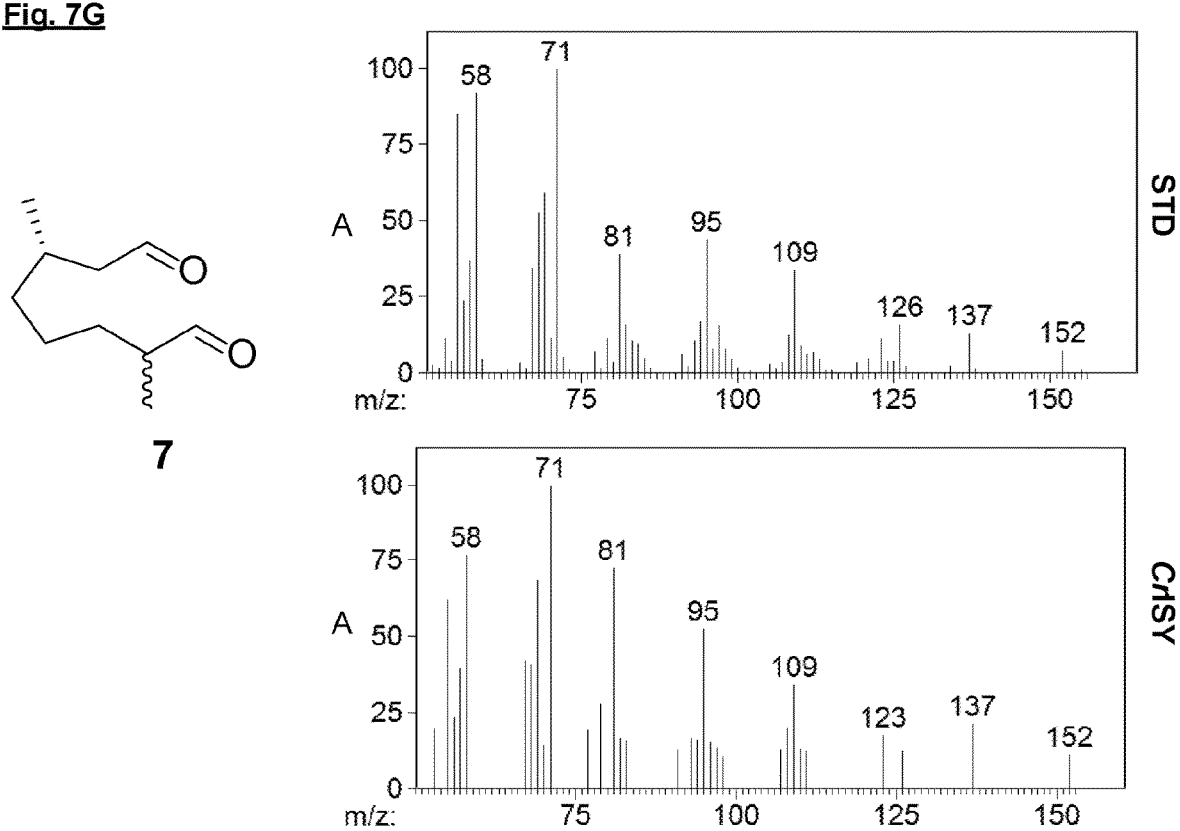

FIG. 7: Electron ionisation (EI) spectra of compounds from FIG. 2A.

All spectra were obtained from the centre of the peaks, except for the CrISY trans-trans-iridodial 5d' spectrum which was taken from the peak tail to avoid overlap with cis-trans-iridodial 5a'. The identity of the standards presented here have been verified by NMR characterisation as previously reported (see methods). STD=standard, A=abundance.

A, cis-trans-nepetalactol 4a.
B, cis-cis-nepetalactol 4b.
C, cis-trans-iridodials 5a.+5a'.
D, trans-cis-iridodial 5c.+5c'.
E, trans-trans-iridodials 5d.+5d'.
F, S-8-oxocitronellal 6.
G, tetrahydro-8-oxogeranial 7.

FIG. 8: Influence of buffer on ISY catalysed reduction of 8-oxogeranial 2.

A, Reduction of 8-oxogeranial 2 by ISY forming cis-trans nepetalactol 4a, cis-cis-nepetalactol 4b, cis-trans-iridodial 5a, trans-cis-iridodial 5c, trans-trans-iridodial 5d, tetrahydro-8-oxogeranial 7 and S-8-oxocitronellal 6. Conditions: 0.5 μM ISY, 1 mM NADPH buffer.

Figure 8A:
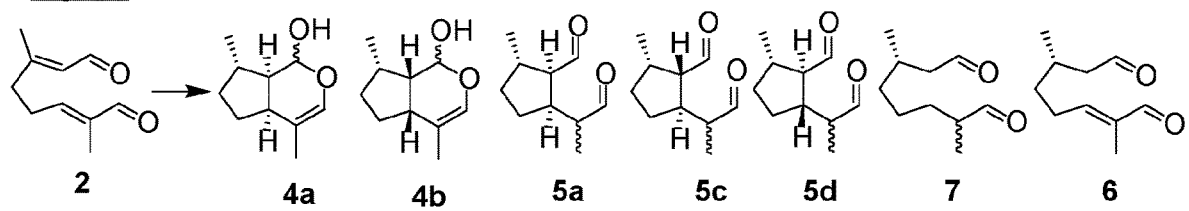
Figure 8B:
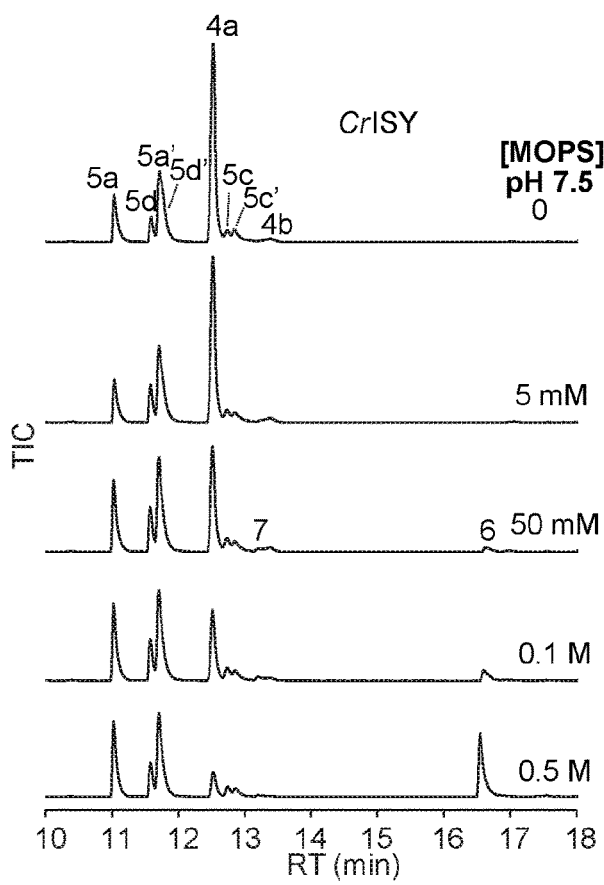
Figure 8C:
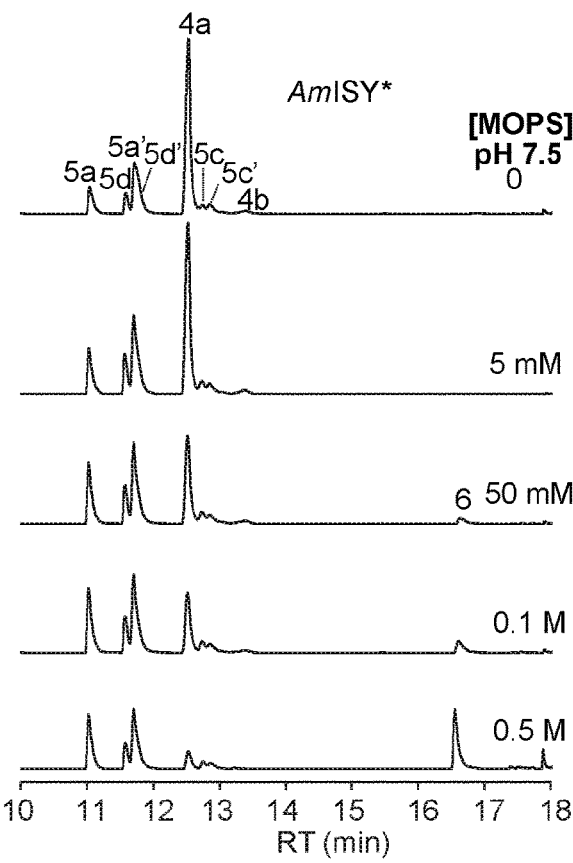
Figure 8D:
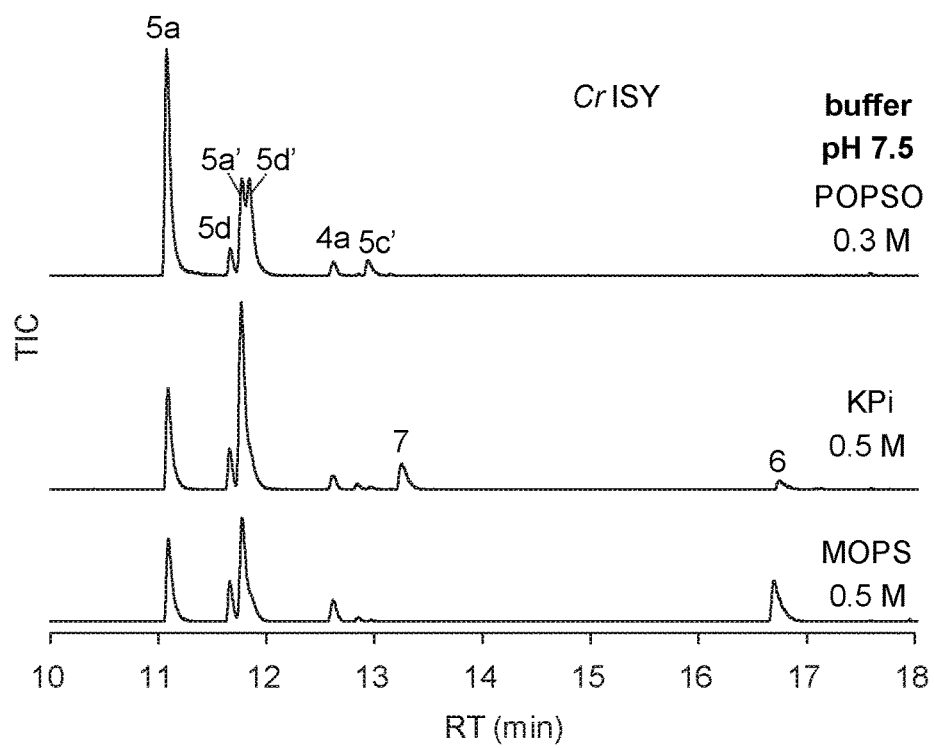

B, Reduction of 2 with CrISY at different MOPS pH 7.5 concentrations, presented as GC-MS TICs. Note the similarity to similar plots with NmISY2 (FIG. 2C) and AmISY (FIG. 8C).

C, Reduction of 2 with AmISY at different MOPS pH 7.5 concentrations. Note the similarity to similar plots with NmISY2 (FIG. 2C) and CrISY (FIG. 8B). * AmISY produces the enantiomeric series to that depicted in panel a.

D, Effect of buffer choice on product profile. Reduction of 2 with CrISY with different buffers. Note the different product profiles: the absence of 6 from POPSO, the presence of 7 in KPi and most crucially the different ratio of diastereomeric ratio 5a and 5a' in POPSO. This indicates direct involvement of buffer in the tautomerisation mechanisms.

E, Effect of pH on product profile of CrISY catalysed reduction of 2. Reducing the pH (more acidic) has a similar result to increasing buffer (general acid) concentrations. The buffer employed was a combination of Good's Buffers (50 mM each of HEPES, CHES and MES).

Figure 9B:
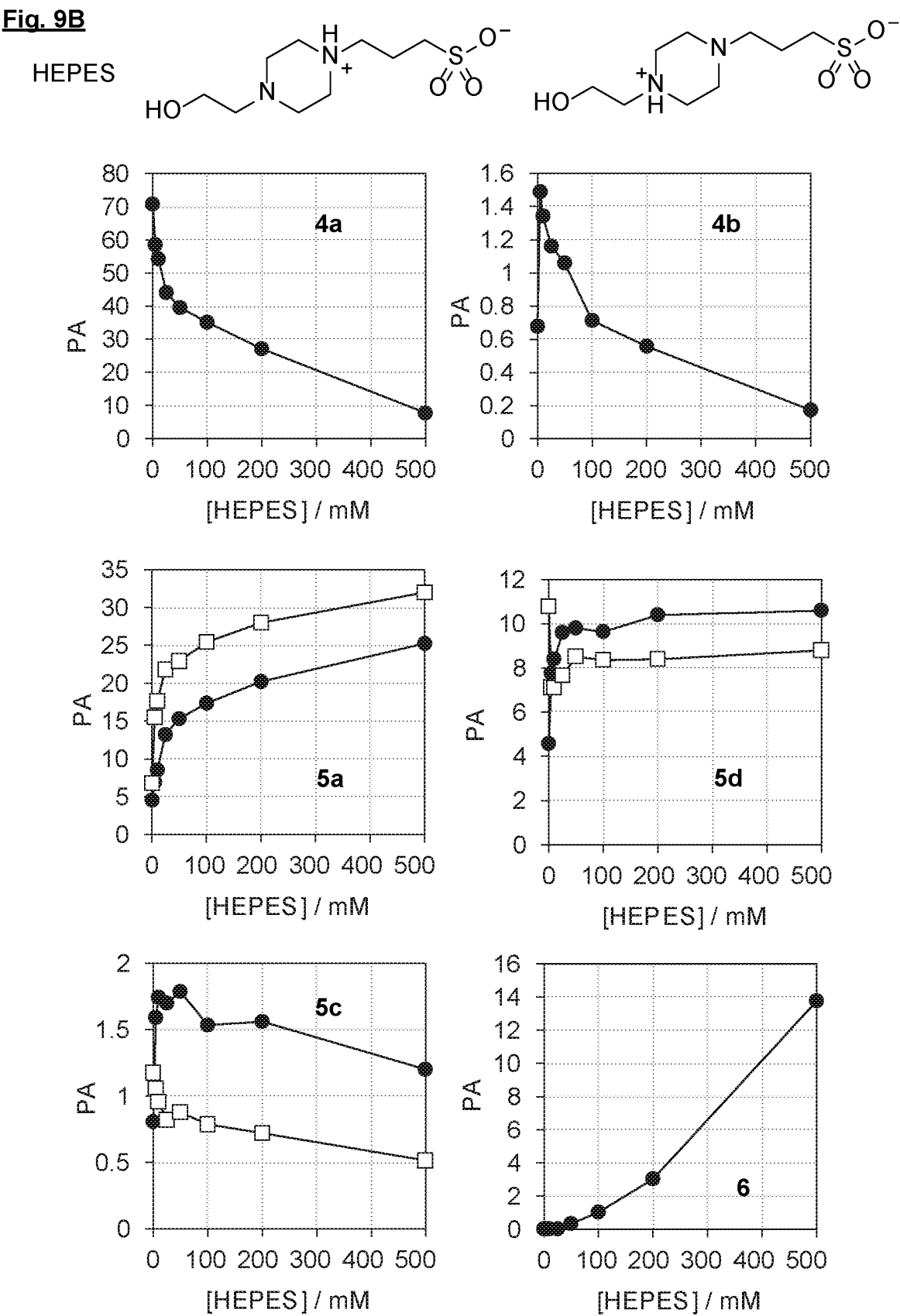
Figure 9C:
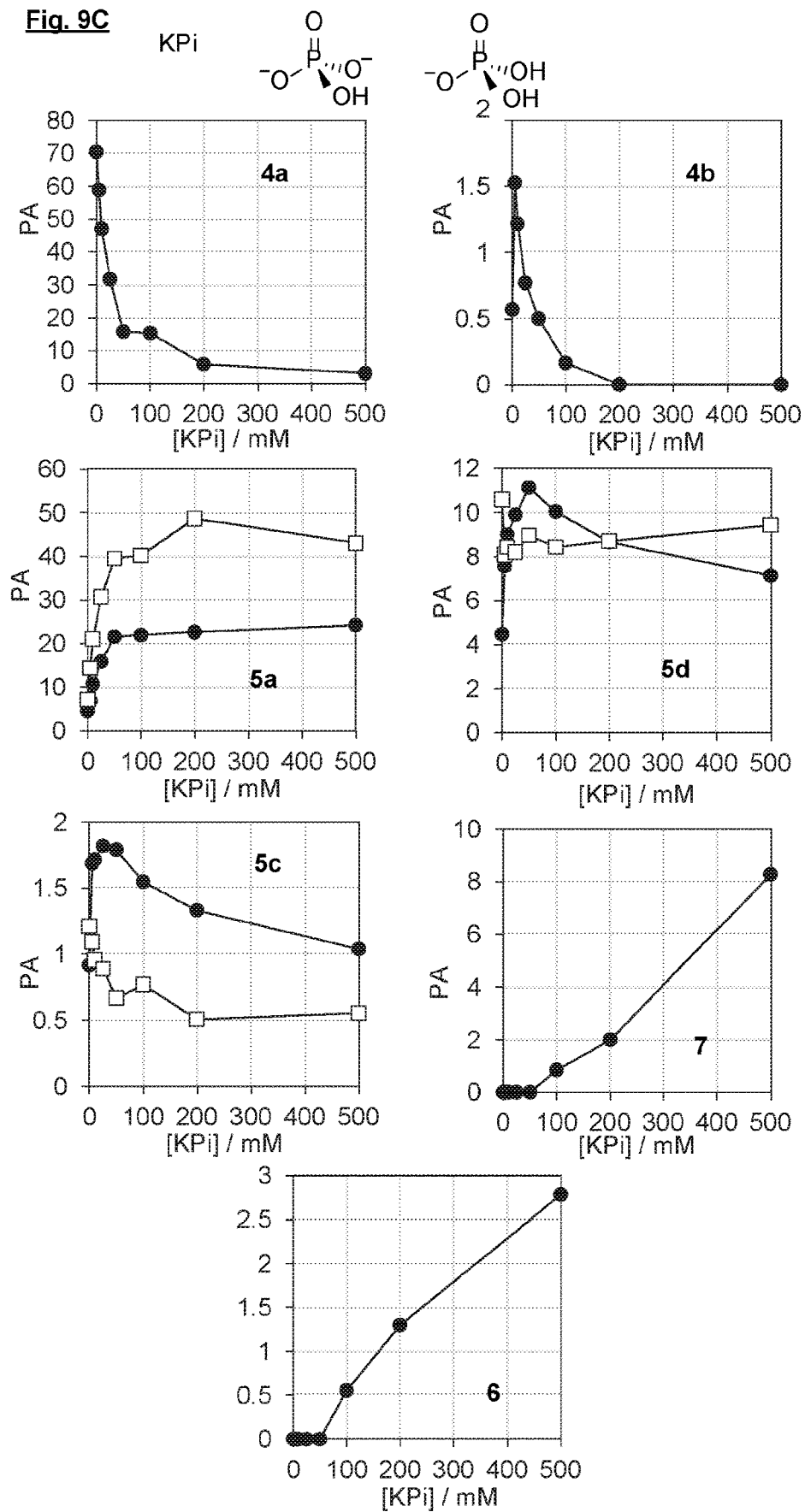

FIG. 9: Analysis of buffer influence on the ISY catalysed reduction of 8-oxogeranial 2. The reduction of 2 by CrISY (ISY) and NADPH was performed with different buffers at different buffer concentrations, at pH 7.5. Products were cis-trans-nepetalactol 4a, cis-cis-nepetalactol 4b, cis-trans-iridodial 5a, trans-cis-iridodial 5c, trans-trans-iridodial 5d, tetrahydro-8-oxogeranial 7 and S-8-oxocitronellal 6.

A, MOPS (3-(N-morpholino)propanesulfonic acid);
B, HEPES (4-(2-hydroxyethyl)-1-piperazineethanesulfonic acid);
C, KPi (potassium phosphate);
D, POPSO (Piperazine-1,4-bis(2-hydroxypropanesulfonic acid)). In all cases concentration of cis-trans-nepetalactol 4a decreases as buffer concentration increases. Between 0-100 mM buffer concentrations of cis-trans-iridodials 5a increase. Above 100 mM buffer the effects are more buffer dependent: for MOPS, HEPES and KPi, the concentration of 8-oxocitronellal 6 increases; for KPi we also see an increase in tetrahydro-8-oxogeranial 7; and for POPSO we see no 6 but an increase in specific iridodial 5 diastereomers. Furthermore, POPSO appears to produce different diastereomer ratios of 5 compared to the other buffers. This data is evidence of direct buffer involvement in cyclisation/tautomerisation processes in the ISY catalysed reduction of 2. Product peak areas are represented as percentage product proportions, obtained by dividing product peak area by total product peak areas (PA). Product peak areas are not normalised by standard curves so do not represent absolute concentrations. Note that peaks of 5a' and 5d' overlap in the GC method—peak areas for these compounds were measured as a split peak (i.e. both to baseline) and not as a peak shoulder. MOPS, HEPES, and POPSO chemical structures depicted in zwitterionic form, KPi depicted as major phosphate forms at pH 7.5.

FIG. 10: Nepetalactol stability in buffer.

Cis-trans-nepetalactol (4a, FIG. 10A) and cis-cis-nepetalactol (4b, FIG. 10B) stability in 10 mM and 0.5 M MOPS pH 7.5. 4a appears to be stable in both these conditions. 4b appears mostly stable in 10 mM MOPS pH 7.5, but is not stable in high buffer concentrations (0.5 M MOPS pH 7.5) and degrades to form iridodials 5. Chromatograms are all GC-MS TICs, RT=retention time (min), incubation was 16 h, 30° C.

FIG. 11: Cyclisation of S-8-oxocitronellal 6 in acidic and alkaline conditions.

A, Outline of cyclisation reaction. S-8-oxocitronellal 6 cyclises to cis-trans-nepetalactol 4a, cis-trans-iridodial 5a, trans-cis-iridodial 5c and trans-trans-iridodial 5d in the presence of H$^+$ or OH$^-$ and H$_2$O.

B, Incubation of S-8-oxocitronellal 6 (0.5 mM) in water at acidic (HCl) or alkaline (NaOH) pH. Samples were incubated at 30° C. for 3 h. Samples at pH 2, 3, 4, 5, 6, 7, 8 and 9 were also examined, but no conversions were observed. RT=retention time (min).

C, As in panel b but after 24 h incubation at 30° C. Between pH 2 and 10 very little conversion was observed. Samples at pH 12 appeared to show complete degradation of 6 and products. No cis-cis-nepetalactol 4b was detected at any pH.

D, Incubation of S-8-oxocitronellal 6 (0.5 mM) in water between pH 10.5 and 11.0 (NaOH). Samples were incubated at 30° ° C. for 16 h. Samples between pH 10.0-10.5 were also examined, but little conversion was observed. It is notable that whilst the bicyclic cis-trans-nepetalactol 4a is a major product in alkaline conditions, cis-cis-nepetalactol 4b is absent. It appears that the spontaneous formation of cis-cis-nepetalactol 4b is unfavourable.

FIG. 12: Electron ionisation (EI) spectra of compounds from FIG. 2D.

Comparison of EI spectra from non-enzymatic reaction with 8-oxocitronellal 6 and 0.5 M MOPS pH 7.5 and enzymatic reaction with 8-oxogeranial 2, NmISY2, NADPH and 0.5 M MOPS pH 7.5. The spectra verify the products are chemically identical despite their different origin. Spectra of two unknown compounds produced in the non-enzymatic reactions are included. These appear to be non-cyclic isomers of 6. All spectra were obtained from the centre of the peaks, except for the trans-trans-iridodial 5d' spectra which were taken from the peak tail to avoid overlap with cis-trans-iridodial 5a'.

A, cis-trans-nepetalactol 4a.
B, S-8-oxocitronellal 6.
C, cis-trans-iridodials 5a.+5a'.
D, trans-cis iridodials 5c.+5c'.
E, trans-trans-iridodials 5d.+5d'.
F, unknown peaks a and b from reaction containing 0.5 mM 6 and 0.5 M MOPS.
RT=retention time (min).

FIG. 13: Identification of trichome located nepetalactol dehydrogenase.

A, Isolation of trichomes using dry ice abrasion. Representative micrograph of isolated trichomes. Trichome types: non-glandular hairs (a), peltate trichomes (b) and capitate trichomes (c).

B, Isoprenoid 2-C-methylerythritol 4-phosphate (MEP) pathway and iridoid biosynthetic pathway. C, Enrichment of MEP and iridoid biosynthetic proteins in the trichome. Proteins were putatively identified by Swiss-Prot annotations and shotgun proteomics. All proteins were significantly trichome enriched (trichome compared to trichome-depleted leaves, Fisher's exact test, p<0.05) except for MCS and CMS. TDL=trichome depleted leaves, L=leaves, T=trichomes. PA=protein abundance (total spectra).

D, Enrichment of selected oxidoreductases in the trichome. Proteins were selected based on trichome enrichment and functional annotation. All proteins were significantly trichome enriched (trichome compared to trichome-depleted leaves, Fisher's exact test, p<0.05). Characterised *N. mussinii* ISY included for comparison.

E, Observation of cis-trans-nepetalactol dehydrogenase activity. Trichome enriched oxidoreductases were cloned, expressed, and assayed as clarified lysate with 1 mM NAD+, 0.5 mM cis-trans-nepetalactol 4a and 50 mM sodium phosphate pH 8.8. Formation of NADH was monitored by absorbance at 340 nm. Blue bars are averages of A340 over the first 5 mins of reaction, green bars are averages of A340 over the final 5 mins of reaction (reaction time 30 minutes). Error bars show one standard deviation from the mean. A=absorbance (340 nm) AU, B=blank, EV=empty vector.

Figure 14D:
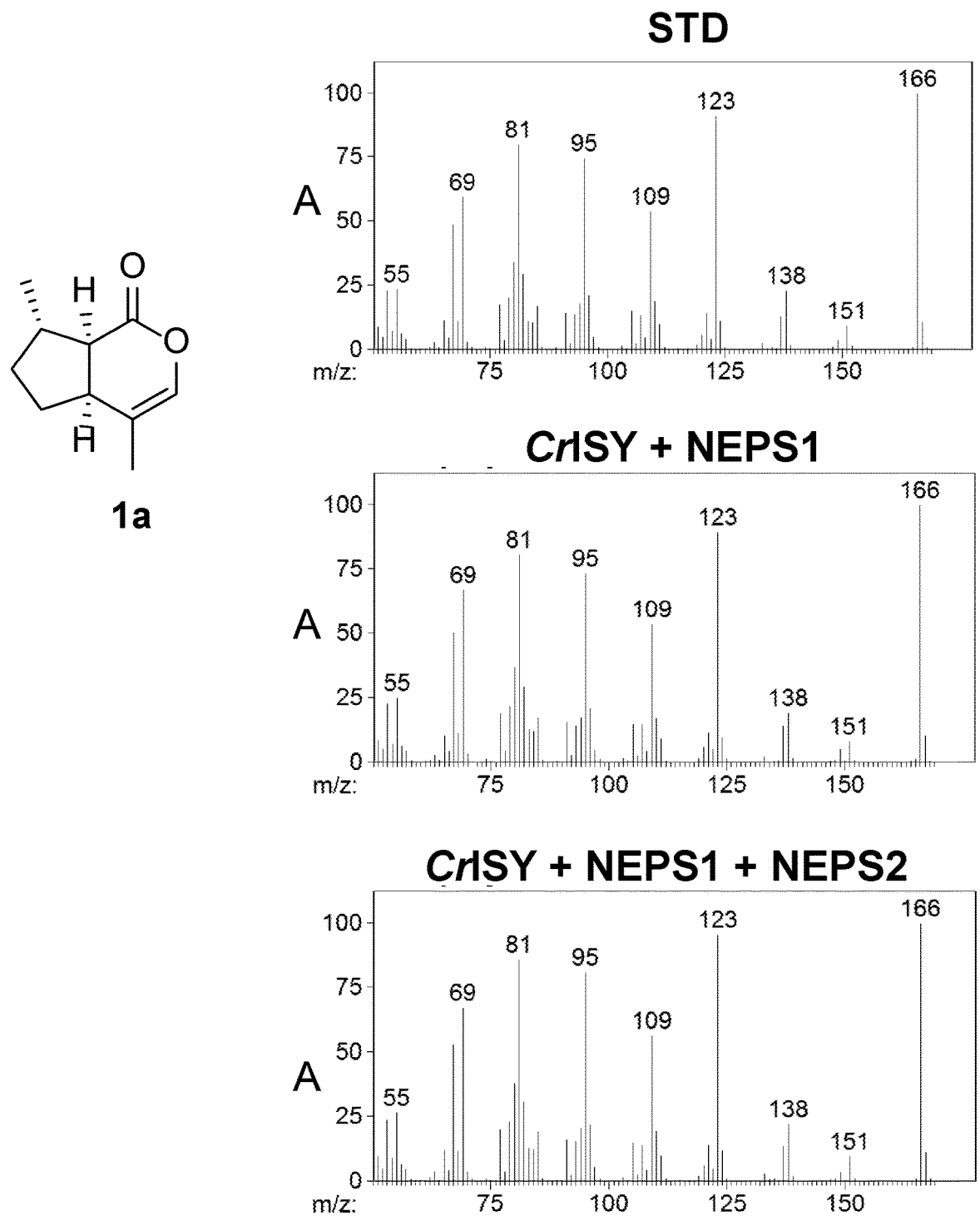
Figure 14E:
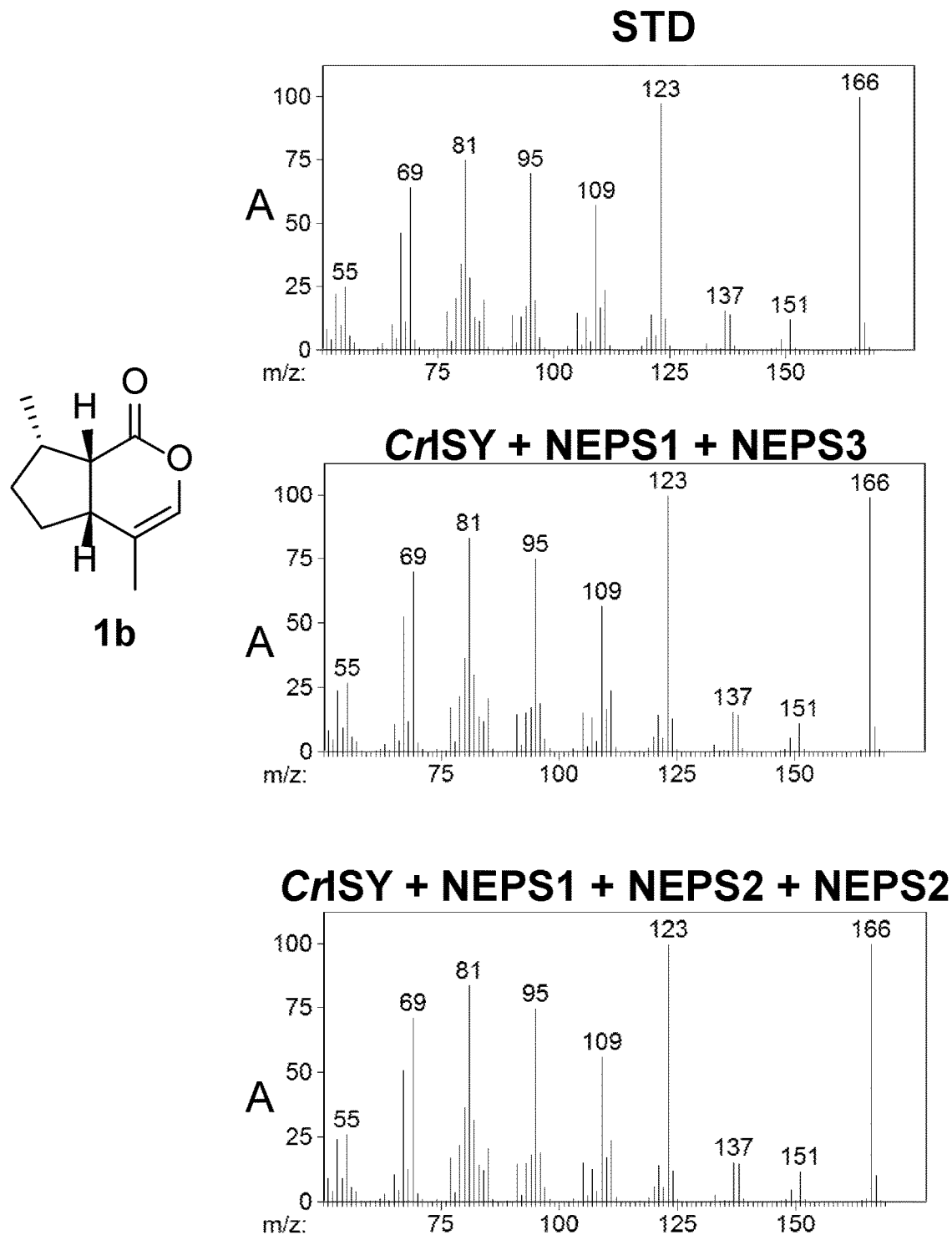
Figure 14F:
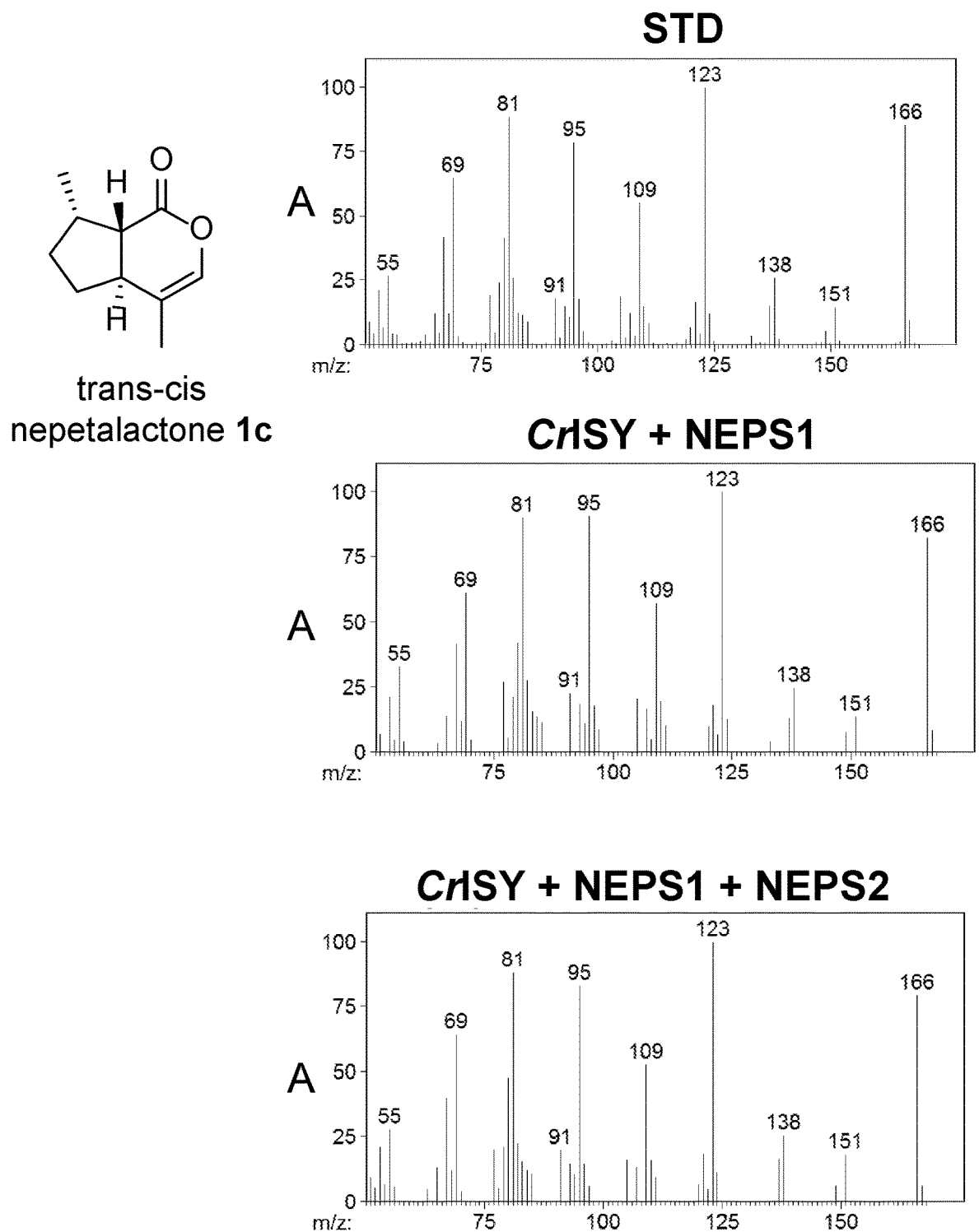

FIG. 14: Electron ionisation (EI) spectra of compounds from FIG. 3.

A, Spectra of products (cis-trans-nepetalactone 1a and cis-cis-nepetalactone 1b) from FIGS. 3B and C (dehydrogenation reaction).

Figure 3A:
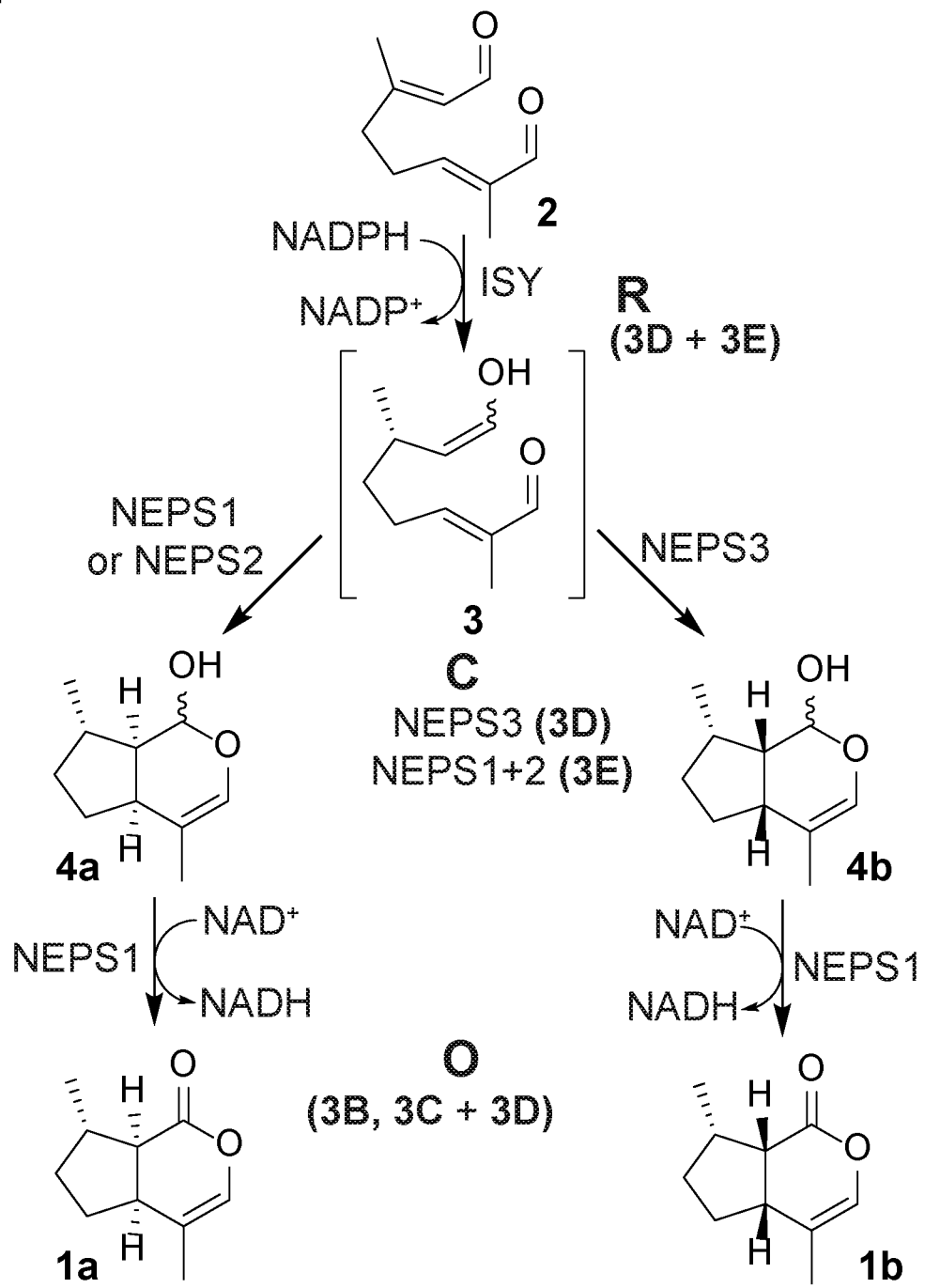
Figure 3D:
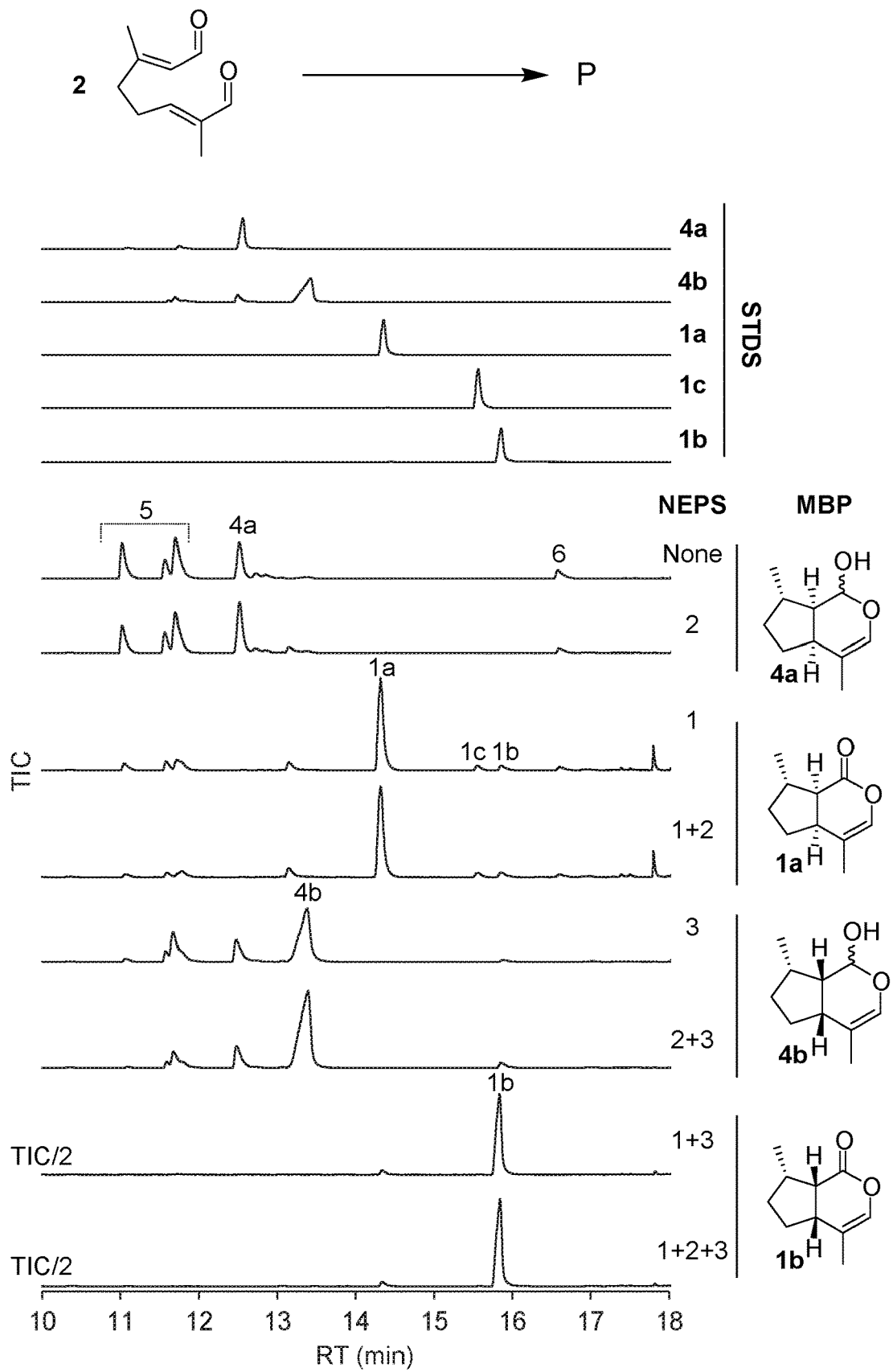

B, cis-trans-nepetalactol 4a product from FIG. 3D (cascades with NEPS and ISY).
C, cis-cis-nepetalactol 4b from FIG. 3D.
D, cis-trans-nepetalactone 1a from FIG. 3D.
E, cis-cis-nepetalactone 1b from FIG. 3D.
F, trans-cis-nepetalactone 1c from FIG. 3D.
STD=standard, A=abundance.

FIG. 15: Sequences and phylogeny of NEPS enzymes.

A, Amino acid sequences of NEPS enzymes cloned from *Nepeta mussinii*. *Mentha x piperita* isopiperitenol/carveol dehydrogenase (MpIPDH) (Uniprot Q5C919) included for comparison. Important residues highlighted below the sequence: * are the SDR catalytic tetrad (N-Y-K-T/S) and ° hypothesised to be involved in oxyanion binding in NEPS3.

B, Sequence identity (%) between NEPS enzymes and MpIPDH. Based on alignment in panel a.

C, Evolutionary context of NEPS enzymes. NEPS enzymes examined in this study are in bold, as is the previously characterised MpIPDH enzyme. The NEPS1 sequence was used to obtain the closely related sequences from across the entire mint plant family (Lamiaceae). Sequences for Lamiaceae and outgroups were obtained from the Mint Genome Project (http://mints.plantbiology.msu.edu/, NCBI BioProject PRJNA359989). Homologous sequences were identified by BLAST and curated, keeping only full-length sequences and removing close paralogs (>95% identity). The codon sequences were aligned and a maximum-likelihood phylogenetic tree was estimated. NEPS enzymes appear to locate to a single clade unique to *Nepeta* (bold), implying that these enzymes evolved within the *Nepeta* lineage. Sequences from two cultivars of *Nepeta mussinii* are included: the cultivar used in this study (and a cultivar used in the Mint Genome Project. Species acronyms: AGFO, *Agastache foeniculum*; AUPE, *Aureolaria pectinata* (outgroup); BAPS, *Ballota pseudodictamnus*; COPY, *Cornutia pyramidata*; GLHE, *Glechoma hederacea*; GMPH, *Gmelina philippensis*; HOSA, *Holmskioldia sanguinea*; HYOF, *Hyssopus officinalis*; HYSU, *Hyptis suaveolens*; LAAL, *Lamium album*; LATI, *Lancea tibetica* (outgroup); LECA, *Leonurus cardiaca*; LYAM, *Lycopus americanus*; MAVU, *Marrubium vulgare*; MEOF, *Melissa officinalis*; MEPI, *Mentha x piperita*; MESP, *Mentha spicata*; MODI, *Monarda didyma*; NECA, *Nepeta cataria*; NEMU, *Nepeta mussinii*; ORMA, *Origanum majorana*; PEAT, *Perovskia atriplicifolia*; PEBA, *Petraeovitex bambusetorium*; PHFR, *Phlomis fruticosa*; ROMY, *Rotheca myricoides*; ROOF, *Rosmarinus officinalis*; SAHI, *Salvia hispanica*; SCBA, *Scutellaria baicalensis*; STOF, *Stachys officinalis/Betonica officinalis*; THVU, *Thymus vulgaris*; VIAG, *Vitex agnus-castus*. Selected gene labels: a=NECA_c35378_g1_i1, b=NEMU_c14104_g1_i1, c=SAHI_c28856_g3_i1, d=SAHI_c28856_g1_12, e=MESP_c41507_g1_i, f=MpIPDH. CS=clade support, SPC=substitutions per codon.

FIG. 16: Enzyme assays with NEPS enzymes and nepetalactone related substrates.

A, cis-trans-nepetalactol 4a to cis-trans-nepetalactone 1a.
B, cis-cis-nepetalactol 4b to cis-cis-nepetalactone 1b.
C, cis-trans-iridodial 5a to cis-trans-nepetalactone 1a.
D, cis-cis-iridodial 5b to cis-cis-nepetalactone 1b.
E, trans-cis-iridodial 5c to trans-cis-nepetalactone 1c.
F, cis-trans-nepetalactone 1a to unknown product.
G, 8-oxogeranial 2 reduction to unknown product.

Besides NEPS1 dehydrogenase activity with 4a and 4b, no other notable activities are observed (i.e. substrates are not converted into products). NEPS1 appears to produce trace quantities of 1a with 5a, however this may be simply conversion of residual 4a present in the substrate sample. There is also trace formation of nepetalactones 1b and 1c by NEPS1 in samples with 5b and 5c respectively. An unknown degradation product of 1a (marked with *) is present in samples using 1a as the substrate. This is also present in the boiled enzyme control so was not considered to be a NEPS activity. Reactions presented as GC-MS TICs. All conditions: 0.5 mM substrate, 1 mM NAD$^+$, 50 mM HEPES pH 8, 0.1 M NaCl, with the exception of g which used NADH in place of NAD$^+$. RT=retention time (min), B=boiled.

FIG. 17: Behaviour of NEPS enzymes with two distinct ISYs.

Cascade reactions with 2, ISY (CrISY or NmISY2), NEPS (1 and/or 3), co-factors and buffer. Products formed: cis-trans-nepetalactone 1a, cis-cis-nepetalactone 1b, trans-cis-nepetalactone 1c, cis-trans-nepetalactol 4a, cis-cis-nepetalactol 4b, iridodials 5, tetrahydro-8-oxogeranial 7 and S-8-oxocitronellal 6. Conditions: 2 µM NEPS, 0.5 µM ISY, 1 mM NADPH, 5 mM NAD$^+$ and 0.1 M MOPS pH 7.5. The behaviour of NEPS enzymes does not appear to be influenced by the ISY employed. This is especially notable due to the evolutionary distance and low sequence identity of CrISY and NmISY2. This outcome suggests the interplay between the ISY and NEPS activities is chemical in nature and does not rely on specific protein-protein interactions. The only observable difference between the chromatograms is the trace presence of the double reduction product 7 in reactions with CrISY—this is a result of a promiscuous CrISY activity. RT=retention time (min)

Figure 18C:
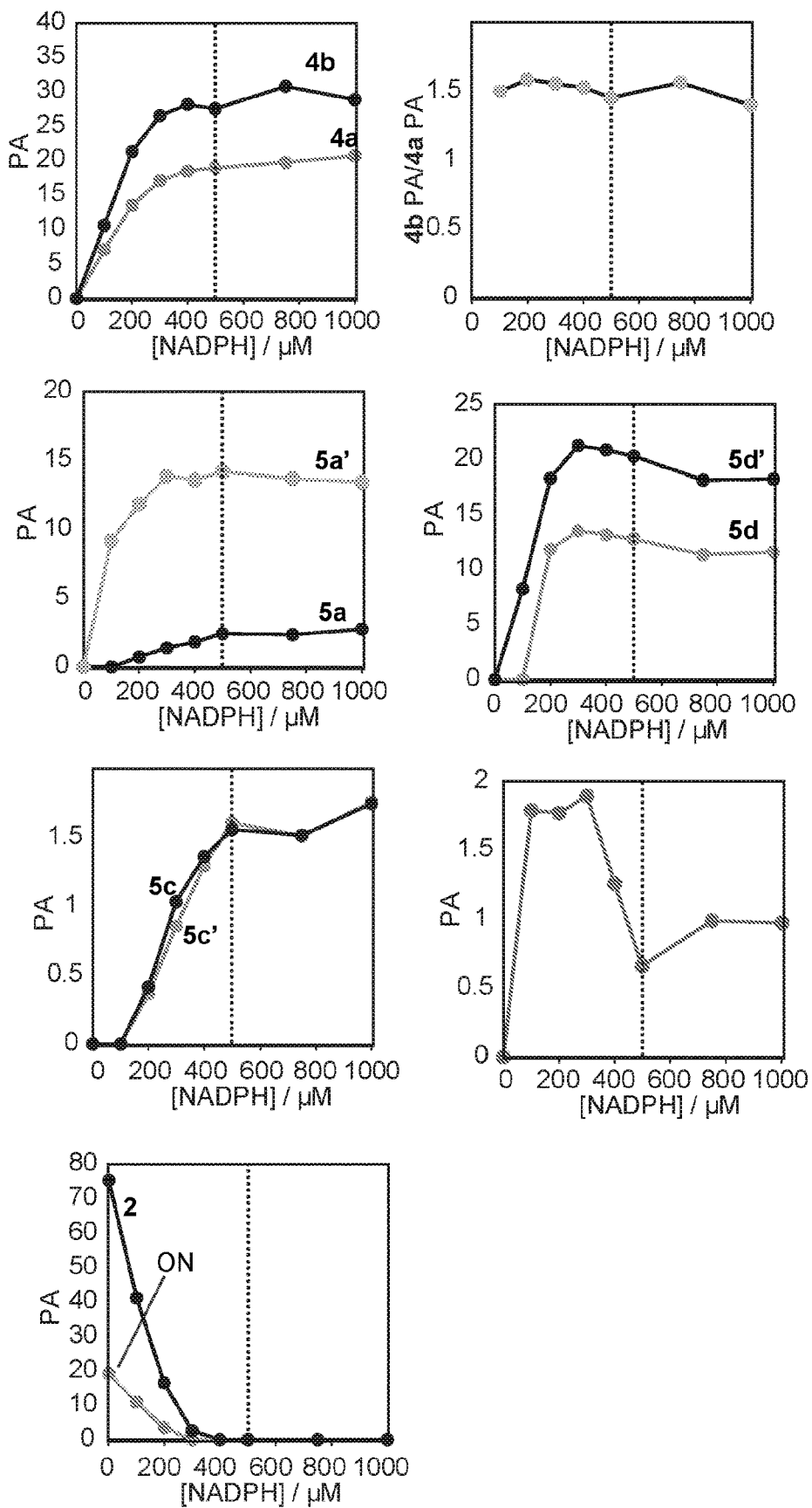

FIG. 18: Influence of enzyme and co-factor concentrations on NEPS3 activity in conjunction with ISY.

Products measured: cis-trans-nepetalactol 4a, cis-cis-nepetalactol 4b, cis-trans-iridodials 5a, trans-trans-iridodials 5d, trans-cis-iridodials 5c, cis-cis-nepetalactone 1b, 8-oxogeranial 2, 8-oxoneral ON. Conversions reported as PA=peak area (% of total).

A, Influence of NEPS3 concentration on products. As NEPS3 concentration is increased, the proportion of cis-cis-nepetalactol 4b formed increases. The proportion of cis-trans-nepetalactol 4a, cis-trans-iridodials 5a and trans-cis-iridodials 5c decrease. At high NEPS3 concentrations, trace formation of cis-cis-nepetalactone is observed. Reactions were conducted with 0.5 µM CrISY, 0.5 mM 2, 1 mM NAD+, 1 mM NADPH, 50 mM HEPES pH 8 and 100 mM NaCl.

B, Influence of NAD+ concentration. Reactions contained 0.5 mM 8-oxogeranial 2, and the equivalent quantity of NAD+ is represented as a dotted vertical line. If NAD+ is consumed in the reaction (with equal stoichiometry to 2), then we would expect maximum conversion at 500 µM and no change beyond this concentration. However, at 50-150 PM [NAD+] the product proportions reach a maximum, and >200 µM appear relatively stable, most notably proportions of cis-trans-nepetalactol 4a and cis-cis-nepetalactol 4b. Only cis-cis-nepetalactone 1b, an oxidation product which requires consumption of NAD+, shows different behaviour. Furthermore, no remaining substrate 2 was observed in any samples, suggesting full conversion. Between 0-150 µM [NAD+] the proportions of 4a and 4b do appear to change, with 4b concentration increasing as NAD+ is supplemented. This data indicates that NAD+ is not consumed in the NEPS3 catalysed formation of 4b (i.e. the cyclisation is not oxidoreductive) but its presence does aid the formation of 4b. It appears to play a strictly catalytic role, for example contributing to the NEPS3 structure. Reactions were conducted as in panel a but with varying [NAD+] and fixed 5 µM NEPS3.

C, Influence of NADPH concentration. Reactions contained 0.5 mM 8-oxogeranial 2, and the equivalent stoichiometric quantity of NADPH is represented as a dotted vertical line. If NADPH is consumed in the reaction (with equal stoichiometry to 2), then we would expect maximum conversion at 500 µM and no change beyond this concentration. This is essentially what is observed. The relative proportions of cis-trans-nepetalactol 4a and cis-cis-nepetalactol 4b are unaffected by changing [NADPH], but the overall conversion appears to be limited when [NADPH]<500 µM. This is also observed in the unreacted substrate 2 at [NADPH]<500 µM. NADPH appears to be consumed by ISY catalysed reduction, and does not affect NEPS3 cyclisation. Reactions were conducted as in panel a but with varying [NADPH] and fixed 5 µM NEPS3. Product peak areas are represented as percentage product proportions, obtained by dividing product peak area by total product peak areas. Product peak areas are not normalised by standard curves so do not represent absolute concentrations. Note that peaks of 5a' and 5d' overlap in the GC method-peak areas for these compounds were measured as a split peak (i.e. both to baseline) and not as a peak shoulder.

Figure 19B:
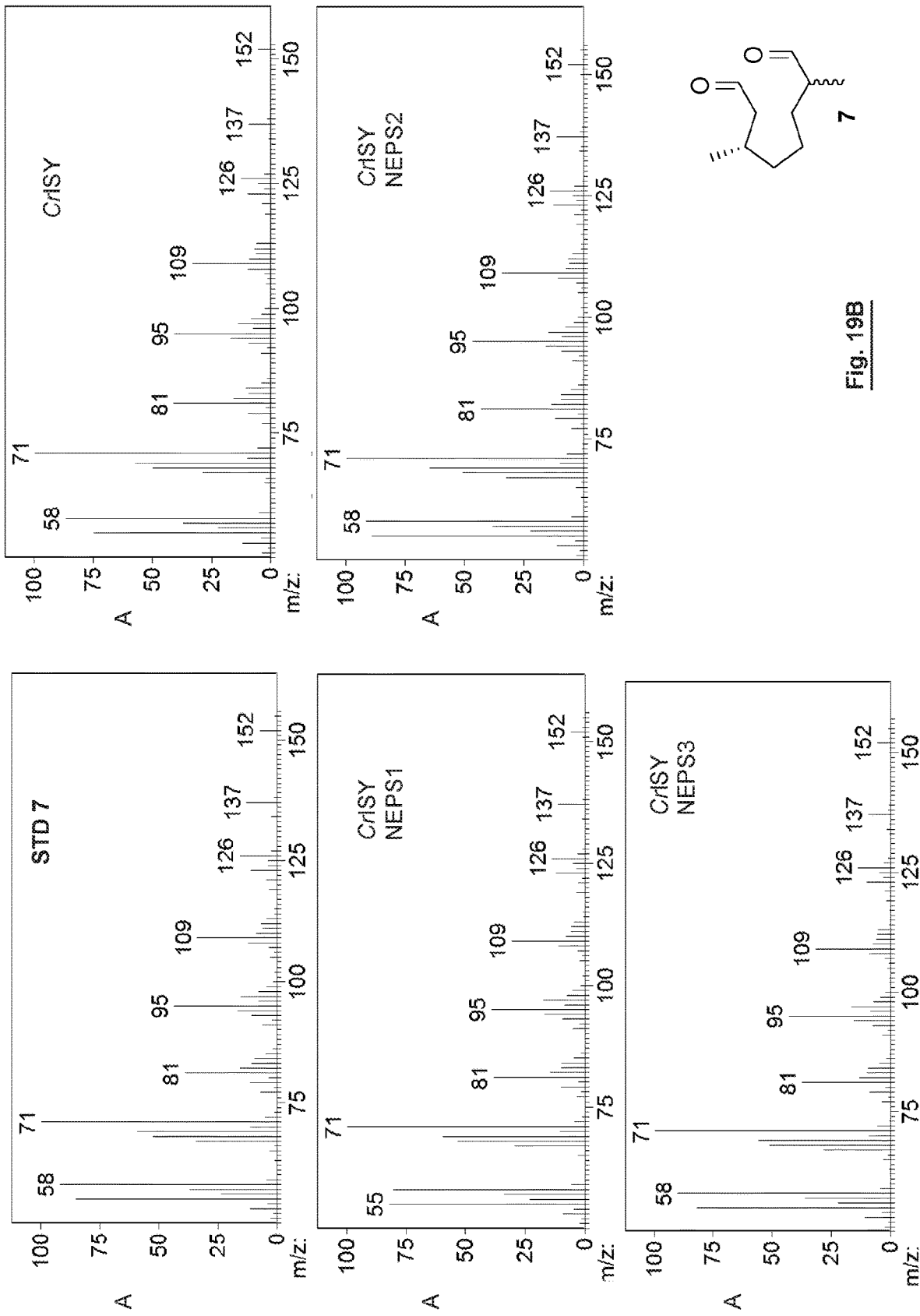
Figure 19C:
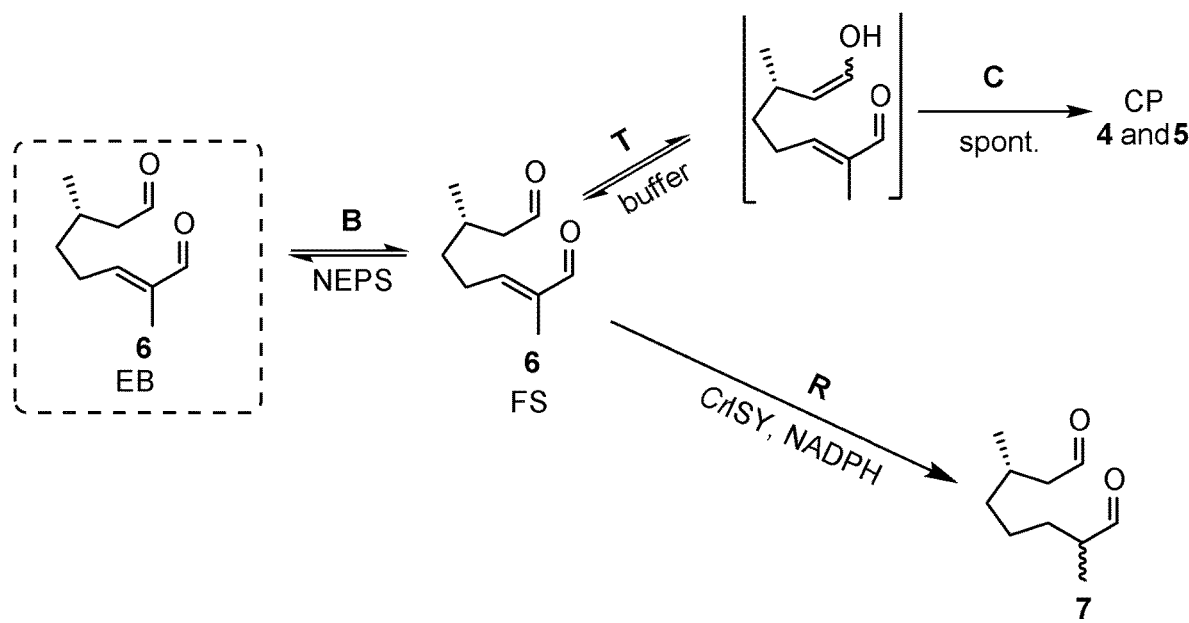

FIG. 19: Reaction with 8-oxocitronellal 6, CrISY and NEPS enzymes.

A, GC-MS TICs of reactions with 0.5 mM S-8-oxocitronellal 6, 0.5 µM CrISY, 2 µM NEPS, 0 or 5 mM NAD$^+$, 1 mM NADPH and 0.5 M MOPS pH 7.5. Compounds formed: tetra-hydro-8-oxogeranial 7, and products. The production of tetrahydro-8-oxogeranial 7 when both CrISY and NEPS are present is notable. TIC abundances for CrISY+NEPS2 and CrISY+NEPS3 have been reduced threefold. STD=standard, RT=retention time (min), E=enzyme.

B, EI spectra of tetrahydro-8-oxogeranial 7 in different reactions from panel a. A=abundance.

C, Scheme of proposed processes occurring in cascades with 8-oxocitronellal 6, CrISY and NEPS. B=binding, T=tautomerisation, C=cyclisation, R=reduction, EB=enzyme bound, CP=cyclic products, FS=free in solution (low conc in presence of NEPS).

When no enzymes are present, 6 undergoes buffer catalysed tautomerisation (to enol 3) and cyclisation to form 4a and iridodials 5 (panel a, second chromatogram from top). CrISY reduces 6 to tetrahydro-8-oxogeranial 7. This reduction is in competition with the spontaneous tautomerisation/cyclisation—the 6 that CrISY is not able to reduce will undergo tautomerisation/cyclisation (panel a, third chromatogram from top). When both CrISY and NEPS enzymes are added, the tautomerisation/cyclisation process appears to be minimised, and 7 accumulates (panel a, bottom three chromatograms). To account for this, we hypothesise that NEPS are reversibly binding 6, reducing the concentration of free 6 in solution. CrISY is then able to reduce all the free 6 into 7, depleting 6 before it undergoes tautomerisation/cyclisation. In reactions with NEPS2 or 3 this process appears to ultimately convert all 6 into 7 (panel a, bottom two chromatograms). A crucial aspect of this process is that NEPS enzymes appear to be binding 6 without turning it over. This supports the notion that the enol 3 and not 6 is the key substrate for NEPS enzymes.

FIG. 20: Structure of NEPS3 (6F9Q).

A, NEPS3 tetramer structure. Subunit main-chain ribbons are rainbow coloured from N-termini (blue) to C-termini (red). NAD+co-factors depicted as black spheres.

B, NEPS3 subunit A structure aligned to secoisolariciresinol dehydrogenase (2BGL). NEPS3 depicted as light brown ribbons, secoisolariciresinol dehydrogenase depicted as cyan ribbons. Active site residues and NAD+ depicted as sticks. The two enzymes have 42% sequence identity.

C, NEPS3 subunit A main chain depicted as ribbons, with NAD+ depicted as sticks. The 1.4 Å resolution electron density for the cofactor only (blue mesh, 2mFo-DFc, contoured at 1 σ) is also shown.

D, Comparison of CrISY substrate binding site (5DBI) and NEPS3 chloride binding site. We hypothesise that the chloride occupies an oxyanion site (S154), analogous to the site on CASY (K146). The chloride in NEPS3 is discreetly disordered and was refined in two positions A and B each with 50% occupancy. The chloride position B has a lower B-factor than position A in all four subunits. Due to this, it appears that position B is the major contributor to the electron density.

FIG. 21: Screen of NEPS1 and NEPS3 mutants.

NEPS1 and NEPS3 mutants were grown in 10 mL cultures, partially purified and assayed. The assays were conducted with 0.5 mM 8-oxogeranial 2, 0.25 µM CrISY, 2.5 mM NAD+, 1 mM NADPH and 0.1 M MOPS pH 7.5. Products observed were cis-trans-nepetalactol 4a, cis-cis-nepetalactol 4b and cis-trans-nepetalactone 1a. Reactions were incubated for 8 h at 30° C. NEPS concentrations were approximately 2 µM (total protein including impurities) based on absorbance at 280 nm. RT=retention time (min).

A, NEPS3 variants with soluble expression. N150T has maintained NEPS3 activity. S154L, K169M and M196S demonstrate low or no detectable formation of cis-cis-nepetalactol 4b. Variants A151T, G152T, S153P, Y165F had no detectable soluble expression.

B, NEPS1 variants demonstrating no detectable formation of cis-trans-nepetalactone 1a: T152N, L156S, Y176F, K171M, T202A. Variants labelled * (TT152NA, S198M) demonstrated poor soluble expression and thus low conversions may be a result of low NEPS concentrations and not simply activity.

C, NEPS1 variants demonstrating detectable formation of cis-trans-nepetalactone 1a. V110A demonstrated the greatest conversion to cis-trans-nepetalactone 1a, superior even WT. Variants T153A and V199A demonstrated reasonable conversions. Variants N125A and P155S catalysed trace but detectable formation of 1a. N125A demonstrated poor soluble expression/purification and thus low conversions may be a result of low NEPS concentrations and not simply activity.

D, NEPS1 variants containing the T154G substitution. All variants containing T154G showed increased formation of cis-trans-nepetalactol 4a compared to WT. T154G and TTT152NAG demonstrated the greatest cyclase activity (formation of 4a and decrease in iridodials 5), whilst maintaining reasonable dehydrogenase activity (evidenced by presence of 1a). TTTP152NAGS and TTTPL152NAGSS showed greater formation of 4a than WT but only trace dehydrogenase activity (1a). T154G is examined further in FIG. 6, FIG. 22 and Table 2.

FIG. 22: Behaviour of NEPS1-T154G variant.

A, Time course of coupled assay with 8-oxogeranial 2, ISY and NEPS1 WT or T154G, presented as GC-MS TICs. Peak areas of 4a and 1a described in FIG. 6B. Conditions: 0.5 mM 8-oxogeranial 2, 0.5 µM CrISY, 2 µM NEPS1 variants, 1 mM NADPH, 1 mM NAD+, 0.1 M MOPS pH 7.5. Products formed: cis-trans-nepetalactone 1a, cis-cis-nepetalactone 1b, trans-cis-nepetalactone 1c, cis-trans-nepetalactol 4a, cis-cis-nepetalactol 4b, cis-trans-iridodials 5a, trans-trans-iridodials 5d, tetrahydro-8-oxogeranial 7 and S-8-oxocitronellal 6. RT=retention time (min); T=time (h).

B, Cyclase activity of NEPS1 investigated with 8-oxocitronellal 6. In the absence of additional co-factor, NEPS1 does not appear to detectably form cis-trans-nepetalactol 4a in the presence of 6 and buffer at greater than background levels. In contrast, NEPS1-T154G forms 4a at greater than background levels in the same conditions. Kinetic analysis of NEPS-T154G can be found in Table 2. Conditions: 0.5 mM S-8-oxocitronellal 6, 20 µM NEPS1, 0.5 M MOPS pH 7.5, No NAD+. Formation of cis-trans-nepetalactol 4a detected.

References to colour features correspond with colour figures of a journal paper entitled "Uncoupled activation and cyclisation in catmint reductive terpenoid biosynthesis" (see Lichman et al., 2019, Nat Chem Biol 15: 71-79). Greyscale features in the figures filed herewith corresponding to the colour features of the paper figures and can be cross-referenced with the colour features noted in the examples below.

DETAILED DESCRIPTION OF THE INVENTION

In a first aspect the invention relates to a method for producing a monoterpenoid compound, comprising:
(1) providing a monoterpenoid precursor;
(1) providing an enzyme; and
(1) contacting the monoterpenoid precursor with the enzyme under catalytic conditions to produce an monoterpenoid compound,
wherein the enzyme comprises an amino acid sequence comprising SEQ ID NO: 1 [NEPS1], and/or SEQ ID NO: 2 [NEPS2], and/or SEQ ID NO: 3 [NEPS3], or a functional variant or homologue of any or all of these enzymes.

The enzyme may comprise an amino acid sequence comprising SEQ ID NO: 1 and be encoded by a nucleotide sequence comprising SEQ ID NO: 4 [NEPS1], and/or the enzyme may comprise an amino acid sequence comprising SEQ ID NO: 2 and be encoded by a nucleotide sequence comprising SEQ ID NO: 5 [NEPS2], and/or the enzyme may comprise an amino acid sequence comprising SEQ ID NO: 3 and be encoded by a nucleotide sequence comprising SEQ ID NO: 6 [NEPS3].

The monoterpenoid compound may comprise a monoterpene indole alkaloid (MIA).

The monoterpenoid precursor may comprise 8-oxocitronellyl enol and/or 8-oxocitronellal and/or derivatives thereof.

The method may further comprise an iridoid synthase (ISY) for example an ISY comprising an amino acid sequence of SEQ ID NO: 7 [AmISY], SEQ ID NO: 8 [NmISY] or SEQ ID NO: 9 [CrISY], or a functional variant or homologue thereof.

The ISY may further comprise an amino acid sequence of SEQ ID NO: 7 encoded by a nucleotide sequence comprising SEQ ID NO: 10 [AmISY], or an amino acid sequence of SEQ ID NO: 8 is encoded by a nucleotide sequence comprising SEQ ID NO: 11 [NmISY2], or an amino acid sequence of SEQ ID NO: 9 is encoded by a nucleotide sequence comprising SEQ ID NO: 12 [CrISY]. The monoterpenoid precursor may comprise 8-oxogeranial.

The monoterpenoid precursor or compound may comprise nepetalactol. The nepetalactol may comprise cis-trans nepetalactol, for example wherein the enzyme comprises an amino acid sequence comprising SEQ ID NO: 1 and/or SEQ ID NO: 2, or a functional variant or homologue thereof. The nepetalactol may comprise cis-cis nepetalactol, wherein the enzyme comprises an amino acid sequence comprising SEQ ID NO: 1, or a functional variant or homologue thereof.

The monoterpenoid compound may comprise nepetalactone. The nepetalactone may comprise cis-trans nepetalactone, wherein the enzyme comprises an amino acid sequence comprising SEQ ID NO: 1 and/or SEQ ID NO: 2, or a functional variant or homologue thereof. The nepetalactone may comprise cis-cis nepetalactone, wherein the enzyme comprises an amino acid sequence comprising SEQ ID NO: 1 and/or SEQ ID NO: 3, or a functional variant or homologue thereof.

The nepetalactone may comprise both cis-trans nepetalactone and cis-cis nepetalactone, wherein the enzyme comprises an amino acid sequence comprising SEQ ID NO: 1 and/or SEQ ID NO: 3, or a functional variant or homologue thereof.

The catalytic conditions may comprise an oxidizing agent, for example oxidized nicotinamide adenine dinucleotide ($NAD^+$).

The monoterpenoid compound may comprise a cyclopentapyran and/or oxadecalin.

The method of the invention may be performed in vivo, for example in planta.

The enzyme or enzymes may be provided by expression in vivo, for example heterologous expression.

The method of the invention may be performed in vitro, for example in an isolated plant cell, wherein the plant may be *Nicotiana benthalmiana, Catharanthus roseus*, or *Nepeta* ssp, for example *Nepeta cataria, Nepeta racemosa, Nepeta faassenii* or *Nepeta mussinii*.

The method may be performed in yeast, for example *Pichia pastoris* or *Saccharomyces cerevisiae*, or in bacteria, for example *E. coli*. The enzyme or enzymes may be provided by expression, for example heterologous expression, in the yeast, bacteria or plant cell.

In another aspect the invention relates to a method for producing a biologically active compound according to a method of the invention, and converting the monoterpenoid compound into a biologically active compound. The biologically active compound may be an insect repellent, insect attractant and/or feline attractant.

The biologically active compound may be a monoterpene indole alkaloid, for example vinblastine, vincristine, camptothecin, quinine and/or yohimbine.

In another aspect the invention relates to an isolated enzyme having an amino acid sequence comprising SEQ ID NO: 1, or a functional variant or homologue thereof.

In another aspect the invention relates to an isolated enzyme having an amino acid sequence comprising SEQ ID NO: 2, or a functional variant or homologue thereof.

In another aspect the invention relates to an isolated enzyme having an amino acid sequence comprising SEQ ID NO: 3, or a functional variant or homologue thereof.

In another aspect the invention relates to an isolated nucleic acid having a nucleotide sequence comprising SEQ ID NO: 4, or a functional variant or homologue thereof.

In another aspect the invention relates to an isolated nucleic acid having a nucleotide sequence comprising SEQ ID NO: 5, or a functional variant or homologue thereof.

In another aspect the invention relates to an isolated nucleic acid having a nucleotide sequence comprising SEQ ID NO: 6, or a functional variant or homologue thereof.

In another aspect the invention relates to a kit comprising:
a first enzyme having a first amino acid sequence selected from the group comprising: SEQ ID NO: 1, SEQ ID NO: 2 and/or SEQ ID NO: 3, or a functional variant or homologue thereof; and optionally also comprising:
a second enzyme having an amino acid sequence selected from the group comprising: SEQ ID NO: 7, SEQ ID NO: 8 and/or SEQ ID NO: 9 or a functional variant or homologue thereof.

In another aspect the invention relates to an expression vector encoding an isolated enzyme of the invention, and optionally also encoding: a second enzyme having an amino acid sequence selected from the group comprising: SEQ ID NO: 7, SEQ ID NO: 8 and/or SEQ ID NO: 9, or a functional variant or homologue thereof. The expression vector optionally includes an artificial regulatory sequence.

In another aspect the invention relates to a host cell comprising the nucleic acid of and/or the expression vector of the invention.

In another aspect the invention relates to a host cell which has been genetically modified to express the enzyme of the invention and optionally also to express: a second enzyme having an amino acid sequence selected from the group comprising: SEQ ID NO: 7, SEQ ID NO: 8 and/or SEQ ID NO: 9, or a functional variant or homologue thereof.

In another aspect the invention relates to a host cell of the invention, wherein the cell is a yeast cell such as a *Pichia pastoris* cell, or a plant cell, for example a *Nicotiana benthalmiana, Catharanthus roseus*, or *Nepeta* ssp cell, for example *Nepeta cataria, Nepeta racemosa, Nepeta faassenii* or *Nepeta mussinii* cell.

In another aspect the invention relates to an a genetically modified plant comprising the nucleic acid and/or the expression vector of the invention.

In yet another aspect the invention relates to a plant which has been gene edited to express the enzyme(s) the invention, and optionally also gene edited to express a second enzyme having an amino acid having an amino acid sequence selected from the group comprising: SEQ ID NO: 7, SEQ ID NO: 8 and/or SEQ ID NO: 9, or a functional variant or homologue thereof.

The plant of the invention may be *Nicotiana benthalmiana, Catharanthus roseus*, or *Nepeta* ssp, for example *Nepeta cataria, Nepeta racemosa, Nepeta faassenii* or *Nepeta mussinii*.

References to "variant" include a genetic variation in the native, non-mutant or wild type sequence. Examples of such genetic variations include mutations selected from: substitutions, deletions, insertions and the like.

More generally, as used herein the term "polypeptide" refers to a polymer of amino acids. The term does not refer to a specific length of the polymer, so peptides, oligopeptides and proteins are included within the definition of polypeptide. The term "polypeptide" may include polypeptides with post-expression modifications, for example, glycosylations, acetylations, phosphorylations and the like. Included within the definition of "polypeptide" are, for example, polypeptides containing one or more analogs of an amino acid (including, for example, unnatural amino acids), polypeptides with substituted linkages, as well as other modifications known in the art both naturally occurring and non-naturally occurring.

As used herein, a "functional variant or homologue" is defined as a polypeptide or nucleotide with at least 50% sequence identity, for example at least 55% sequence identity, at least 60% sequence identity, at least 65% sequence identity, at least 70% sequence identity, at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity with the reference sequence.

Sequence identity between nucleotide or amino acid sequences can be determined by comparing an alignment of the sequences. When an equivalent position in the compared sequences is occupied by the same base or amino acid, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps.

Calculation of maximum percent identity involves the production of an optimal alignment, taking into consideration gap penalties.

Suitable computer programs for carrying out sequence comparisons are widely available in the commercial and public sector. Examples include MatGat (Campanella et al., 2003, BMC Bioinformatics 4: 29; program available from http://bitincka.com/ledion/matgat), Gap (Needleman & Wunsch, 1970, J. Mol. Biol. 48: 443-453), FASTA (Altschul et al., 1990, J. Mol. Biol. 215: 403-410; program available from http://www.ebi.ac.uk/fasta), Clustal W 2.0 and X 2.0 (Larkin et al., 2007, Bioinformatics 23: 2947-2948; program available from http://www.ebi.ac.uk/tools/clustalw2) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp 1-44, Addison Wesley; programs available from http://www.ebi.ac.uk/tools/emboss/align). All programs may be run using default parameters.

For example, sequence comparisons may be undertaken using the "Needle" method of the EMBOSS Pairwise Alignment Algorithms, which determines an optimum alignment (including gaps) of two sequences when considered over their entire length and provides a percentage identity score. Default parameters for amino acid sequence comparisons ("Protein Molecule" option) may be Gap Extend penalty: 0.5, Gap Open penalty: 10.0, Matrix: Blosum 62. Default parameters for nucleotide sequence comparisons ("DNA Molecule" option) may be Gap Extend penalty: 0.5, Gap Open penalty: 10.0, Matrix: DNAfull.

In one aspect of the invention, the sequence comparison may be performed over the full length of the reference sequence.

Particular non-limiting embodiments of the present invention will now be described in detail.

EXAMPLES

Example 1

Introduction

Terpene synthases typically form complex molecular scaffolds by concerted activation and cyclization of linear starting materials in a single enzyme active site. Here we show that iridoid synthase, an atypical reductive terpene synthase, catalyses the activation of its substrate 8-oxogeranial into a reactive enol intermediate but does not catalyse the subsequent cyclisation into nepetalactol. This discovery led us to identify a class of nepetalactol-related short-chain dehydrogenase enzymes (NEPS) from catmint (*Nepeta mussinii*) which capture this reactive intermediate and catalyse the stereoselective cyclisation into distinct nepetalactol stereoisomers. Subsequent oxidation of nepetalactols by NEPS1 provides nepetalactones, metabolites that are well known for both insect-repellent activity and euphoric effect in cats. Structural characterisation of the NEPS3 cyclase reveals it binds to $NAD^+$ yet does not utilise it chemically for a non-oxidoreductive formal [4+2] cyclisation. These discoveries will complement metabolic reconstructions of iridoid and monoterpene indole alkaloid biosynthesis.

Results

The Mechanism of Iridoid Synthase (ISY)

Recently we hypothesised that synthesis of the different nepetalactone stereoisomers in *Nepeta* was controlled by species-specific ISYs catalysing both the reduction of 2 and the subsequent stereodivergent cyclisations. However, this was not the case; *Nepeta* ISYs produced the same stereoisomeric product profile as CrISY. Therefore, an alternative mechanism for the control of iridoid stereochemistry was developed.

Figure 2A:
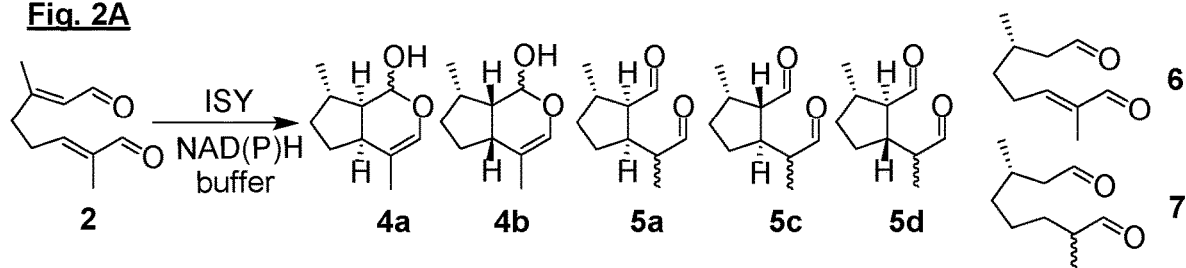
Figure 2B:
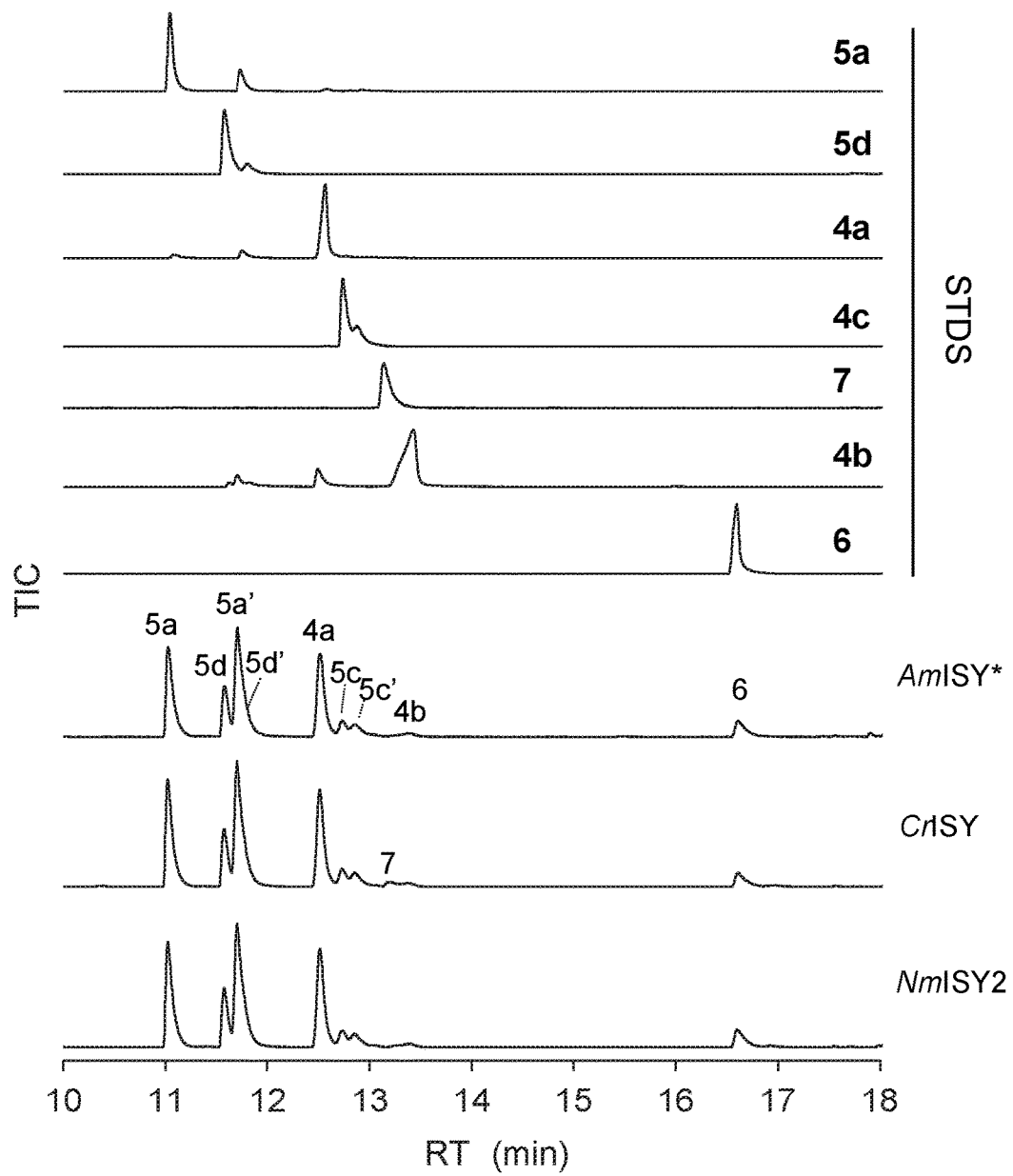

The first step toward understanding the origin of the divergent stereochemistry of nepetalactones 1 was to further explore the ISY mechanism. As observed in previous studies, the ISY catalysed reduction of 8-oxogeranial 2 generates a number of isomeric products (FIGS. 2A and B, FIG. 7). The achiral product profile of the observed isomers is largely independent of the ISY employed, despite modest sequence identities (48-65%) and different stereoselectivities of the reduction step (AmISY is 7R-selective, NmISY2 and CrISY are 7S-selective) (FIG. 2B).

Figure 8E:
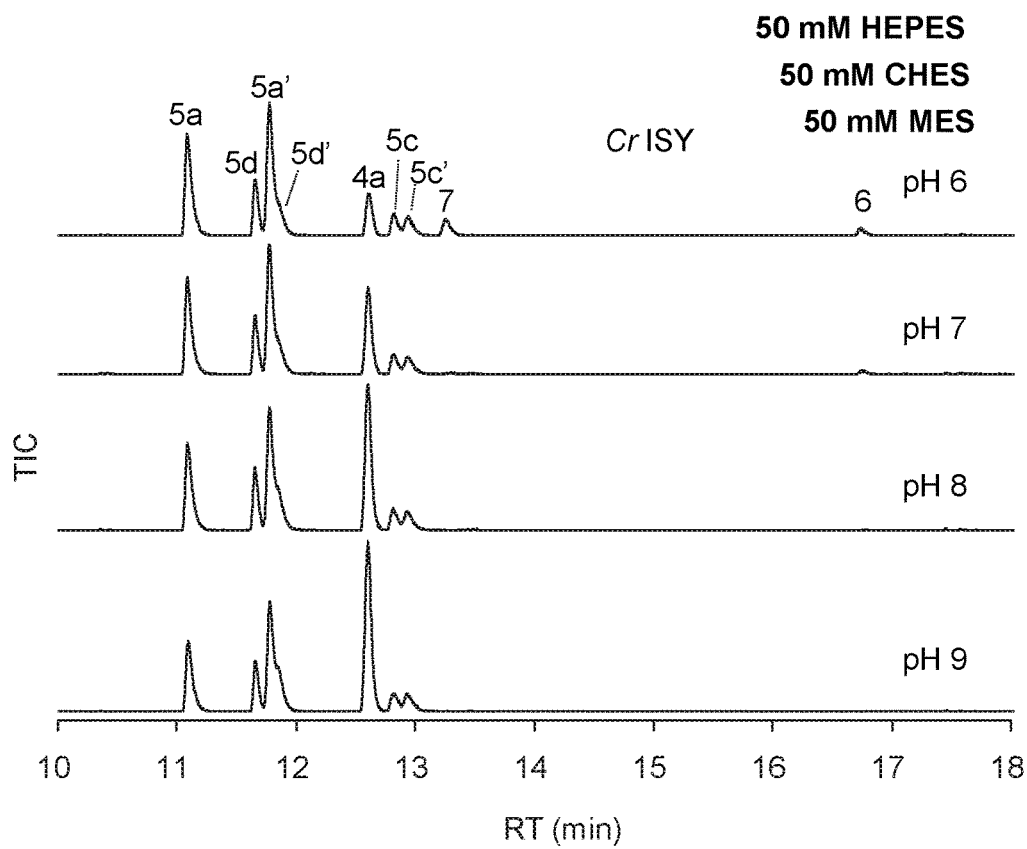
Figure 10A:
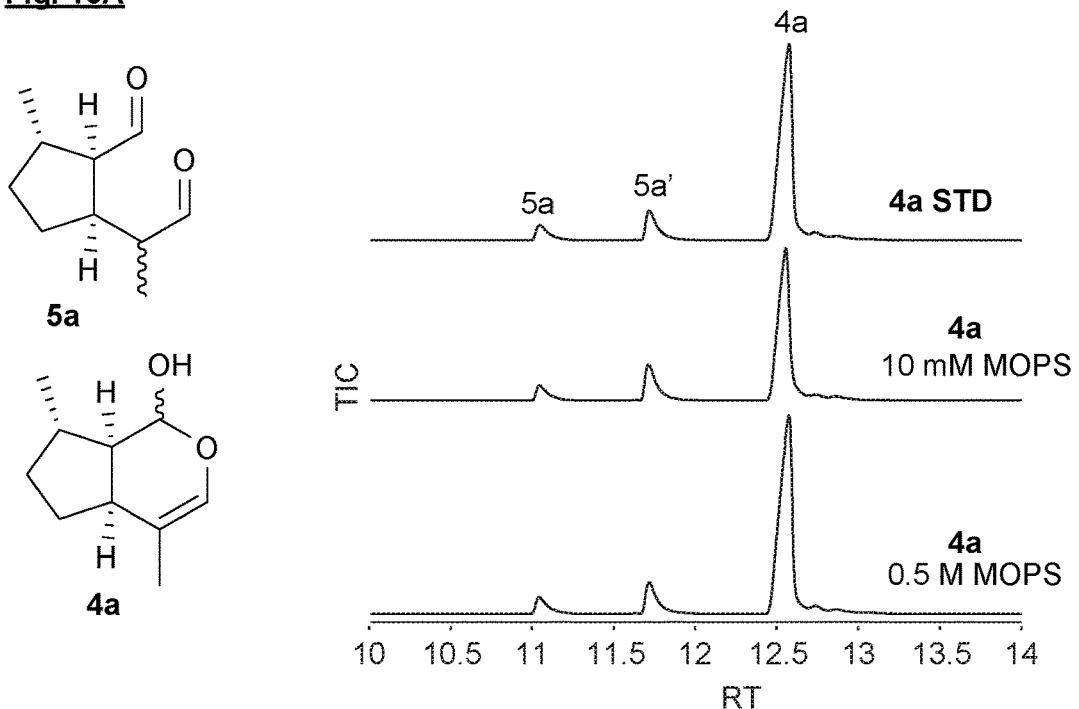
Figure 10B:
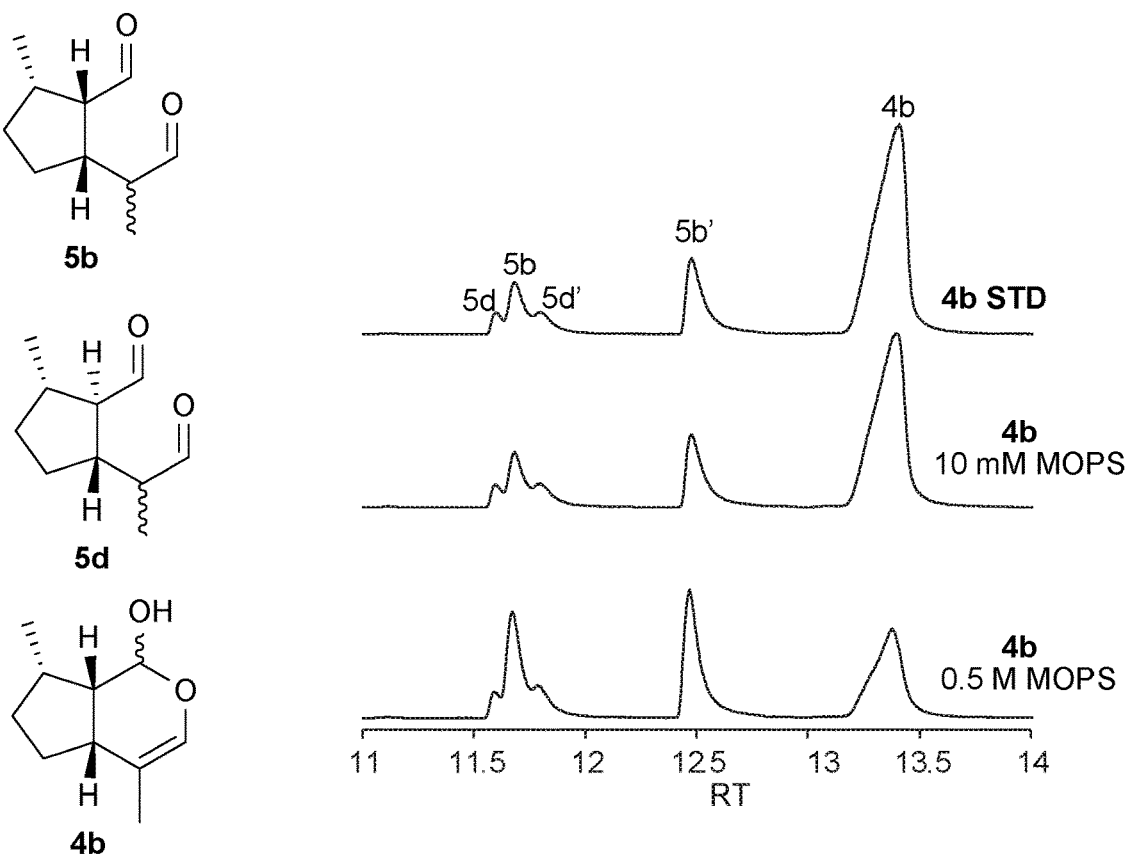
Figure 11A:
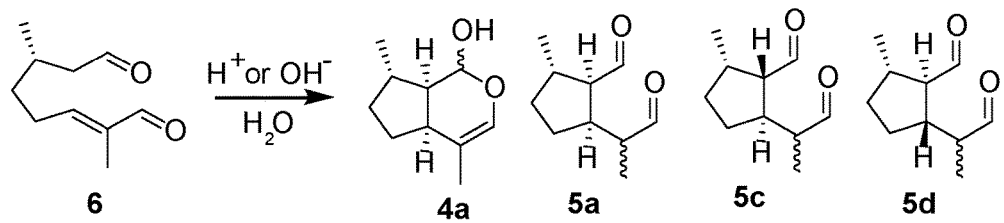
Figure 11B:
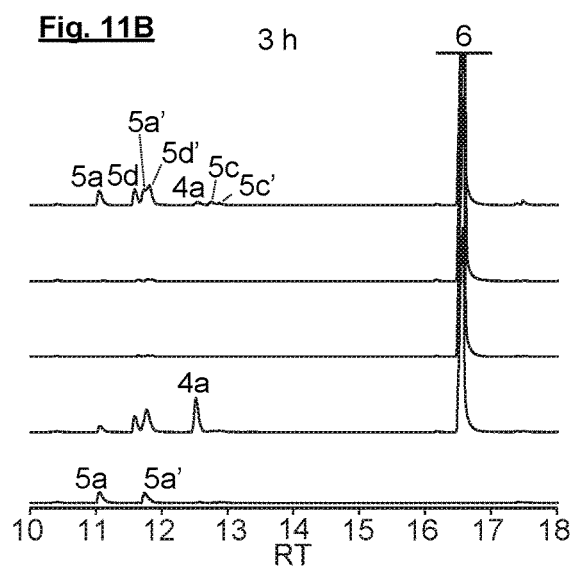
Figure 11C:
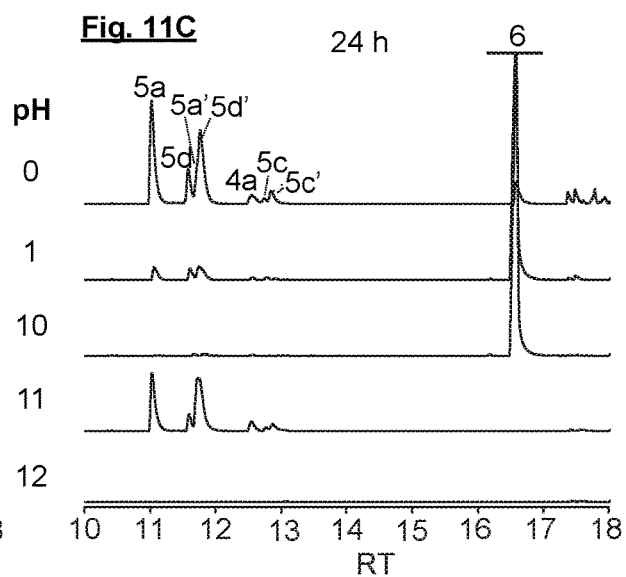
Figure 11D:
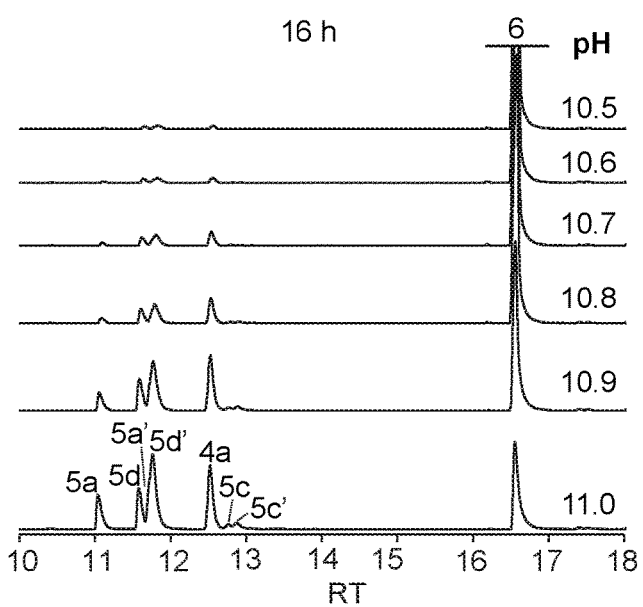

Although the product profile was invariant with respect to the enzyme catalyst, it was strongly influenced by the reaction conditions, especially the concentration of the buffer (FIG. 2C). With low buffer concentration, cis-trans-nepetalactol 4a was the major product; as buffer concentration was increased, more iridodials 5 and non-cyclised 8-oxocitronellal 6 were observed. A similar pattern was observed with all ISYs and buffers tested (FIGS. 8A-D, 9). The trend was not a result of cis-trans-nepetalactol 4a ring opening in high buffer concentrations (FIG. 10A). Furthermore, changing the buffer pH also affected the product profile, with lower pH resulting in the formation of more cis-trans-iridodials 5a compared to cis-trans-nepetalactol 4a (FIG. 8E).

The sensitivity of the product distribution to changes in solvent conditions led us to hypothesise that ISY reduces 2 to form the activated intermediate 3 which then leaves the enzyme active site and diffuses into the solvent. In the solvent, 3 can quench through either cyclisation or tautomerisation to form a mixture of products. We propose that the buffer acts as a general acid catalyst, promoting tautomerisation. Using MOPS buffer, this results in three regimes (FIG. 2C): at low buffer concentrations (<50 mM) two cyclisations generate the bicyclic 4a as the dominant product; in moderately buffered concentrations (50-500 mM) one cyclisation followed by keto-enol tautomerisation to form monocyclic 5a becomes favoured; at high buffer concentrations (≥500 mM) direct keto-enol tautomerisation of 3 into 6 becomes the dominant route. The promotion of tautomerisation by buffer molecules mirrors simulations that have highlighted the active involvement of solvent molecules in tautomerisation mechanisms.

Figure 2D:
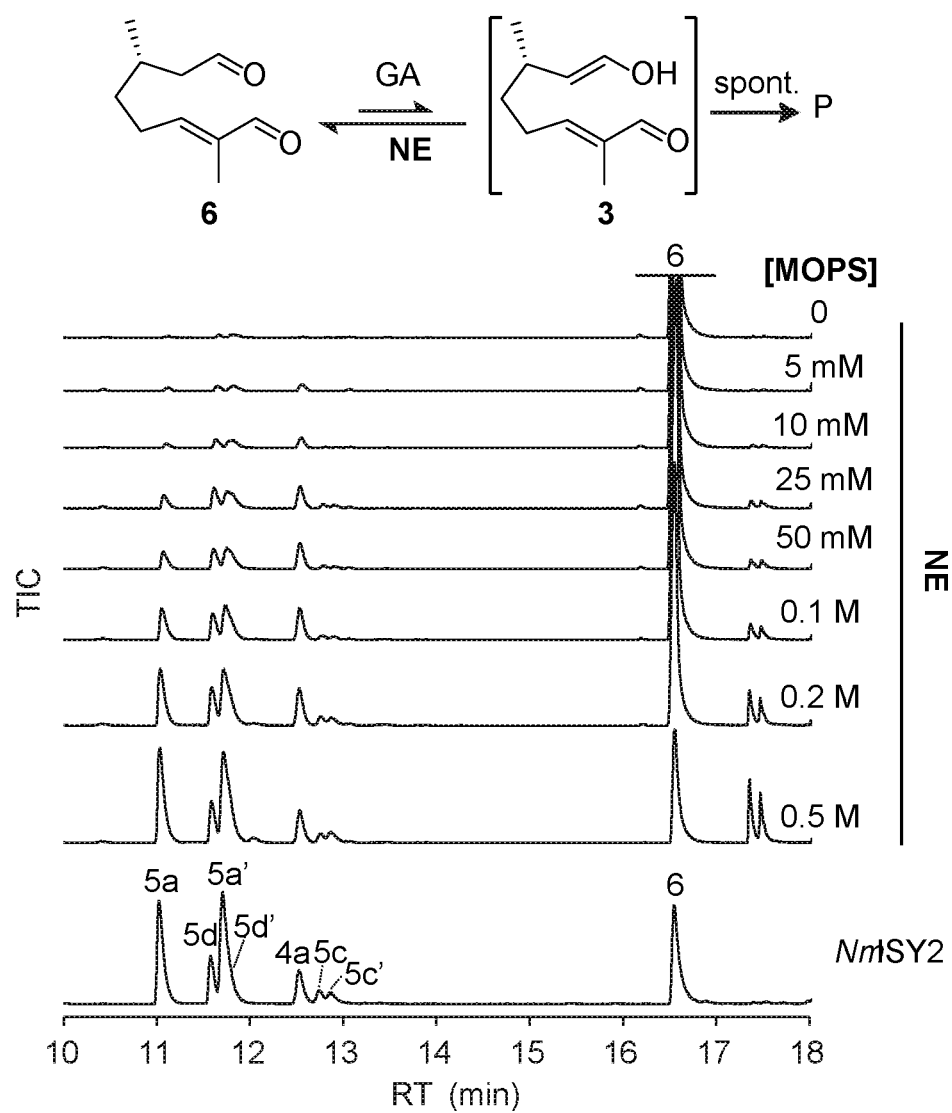

To validate that the ISY product profile was a result of the non-enzymatic cyclisation of 3, we aimed to form 3 in the absence of enzyme. This was achieved by incubation of S-8-oxocitronellal 6 in unbuffered water at acidic (<2) or alkaline (>10) pHs (FIG. 11), or in buffered water at pH 7.5 (FIG. 2D, FIG. 12). Buffer or extreme pH promotes keto-enol tautomerisation of 6 into 3, which could then undergo cyclisation/tautomerisation in an analogous manner to ISY reactions. In fact, formation of 4a from 6 is an established synthetic route. In high concentrations of buffer (500 mM MOPS), the product profiles of the ISY catalysed reduction of 2 and the non-chemical cyclisation of 6 are remarkably similar (FIG. 2D, FIG. 12), supporting the hypothesis that iridoid cyclisation is not enzymatically catalysed.

Figure 1B:
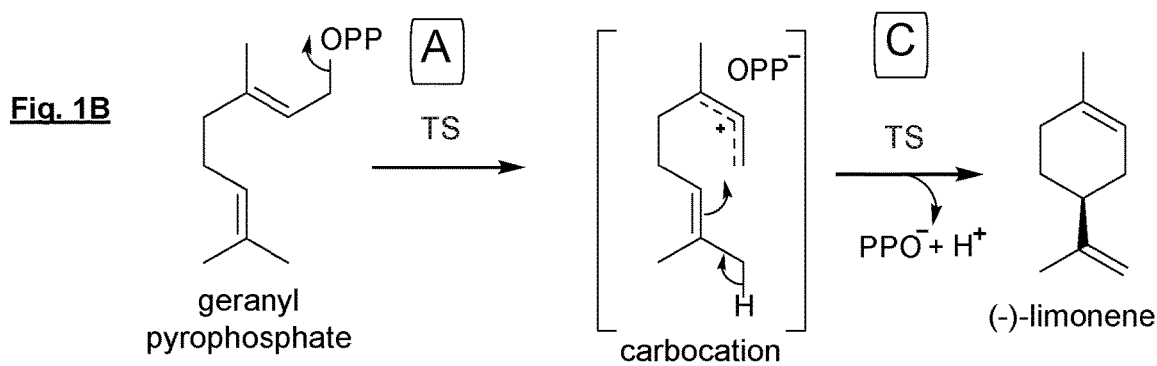
Figure 1C:
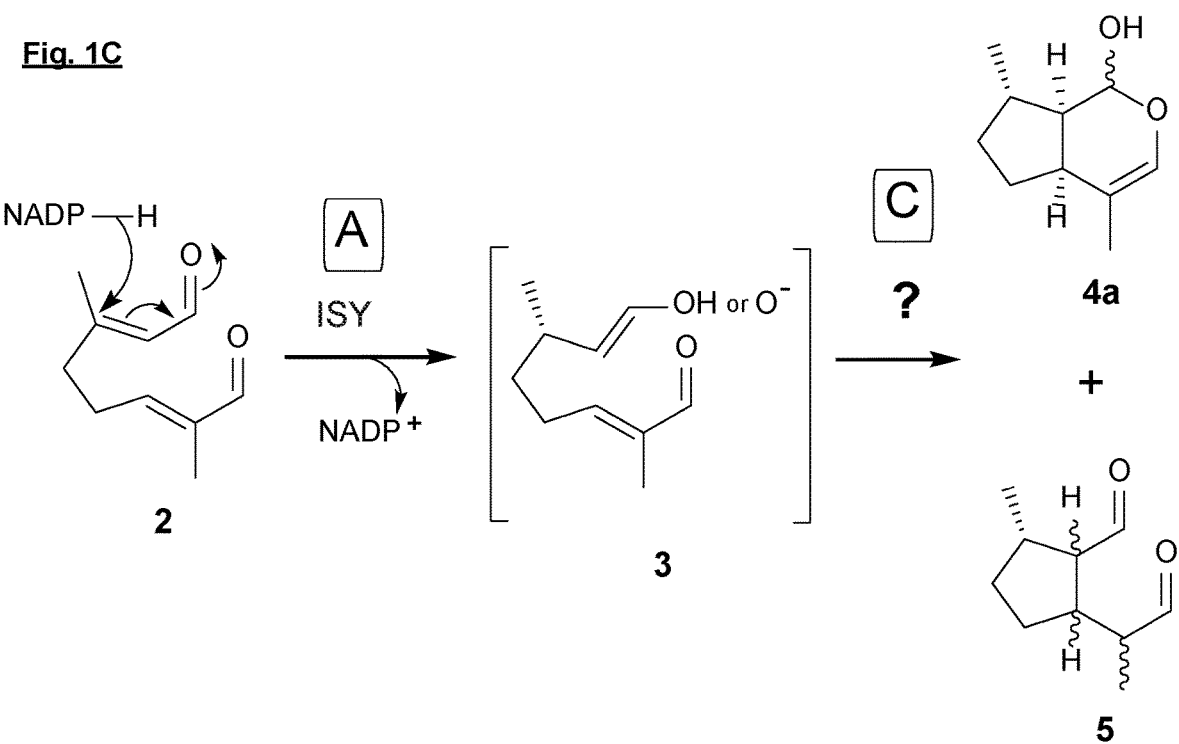
Figure 1D:
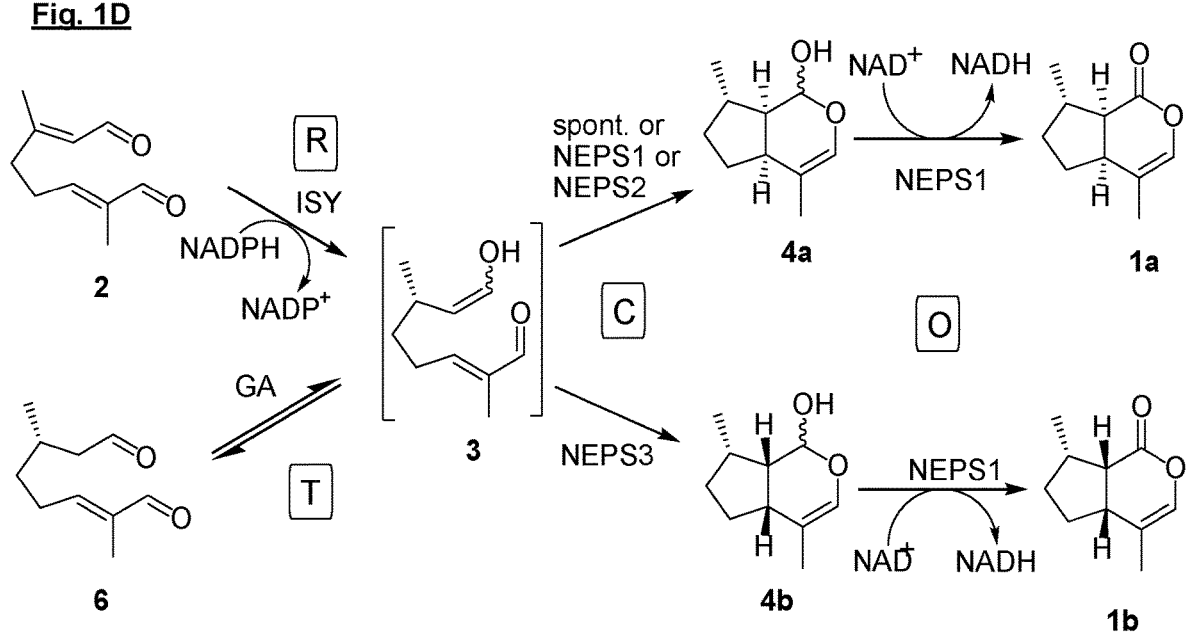

Therefore, unlike canonical terpene synthases which catalyse concerted activation and cyclisation (FIG. 1B), ISY catalyses the activation of its linear substrate (8-oxogeranial 2 to 8-oxocitronellyl enol 3) but does not appear to catalyse the subsequent cyclisation. Instead, we hypothesise that 3 diffuses out of the ISY active site into the solvent where it cyclises. This mechanism is supported by the ISY crystal structure which did not show substrate binding modes conducive to cyclisation. The notion of free 3 raised the possibility that the iridoid stereochemistry may be defined by a partner cyclase enzyme, capable of accepting 3 as a substrate and catalysing diastereoselective cyclisation.

Identification of Nepetalactol Related Short-Chain-Reductases (NEPS)

Identifying a cyclase that works in partnership with ISY presents a challenge: because this proposed reaction is unprecedented, it is difficult to predict what type of enzyme family would catalyse such a cyclisation. However, nepetalactone biosynthesis in *Nepeta* is localised to a specific plant organ, glandular trichomes. Therefore, we could compare the proteome of trichomes to trichome-depleted leaves to identify genes that are selectively expressed at the site of nepetalactone biosynthesis, thereby considerably narrowing the pool of potential gene candidates.

Figure 13A:
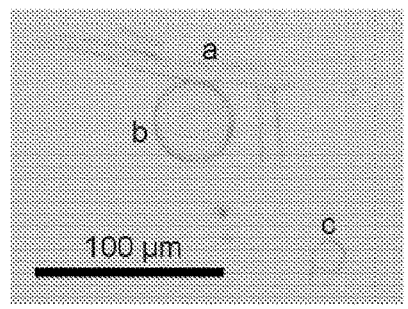
Figure 13B:
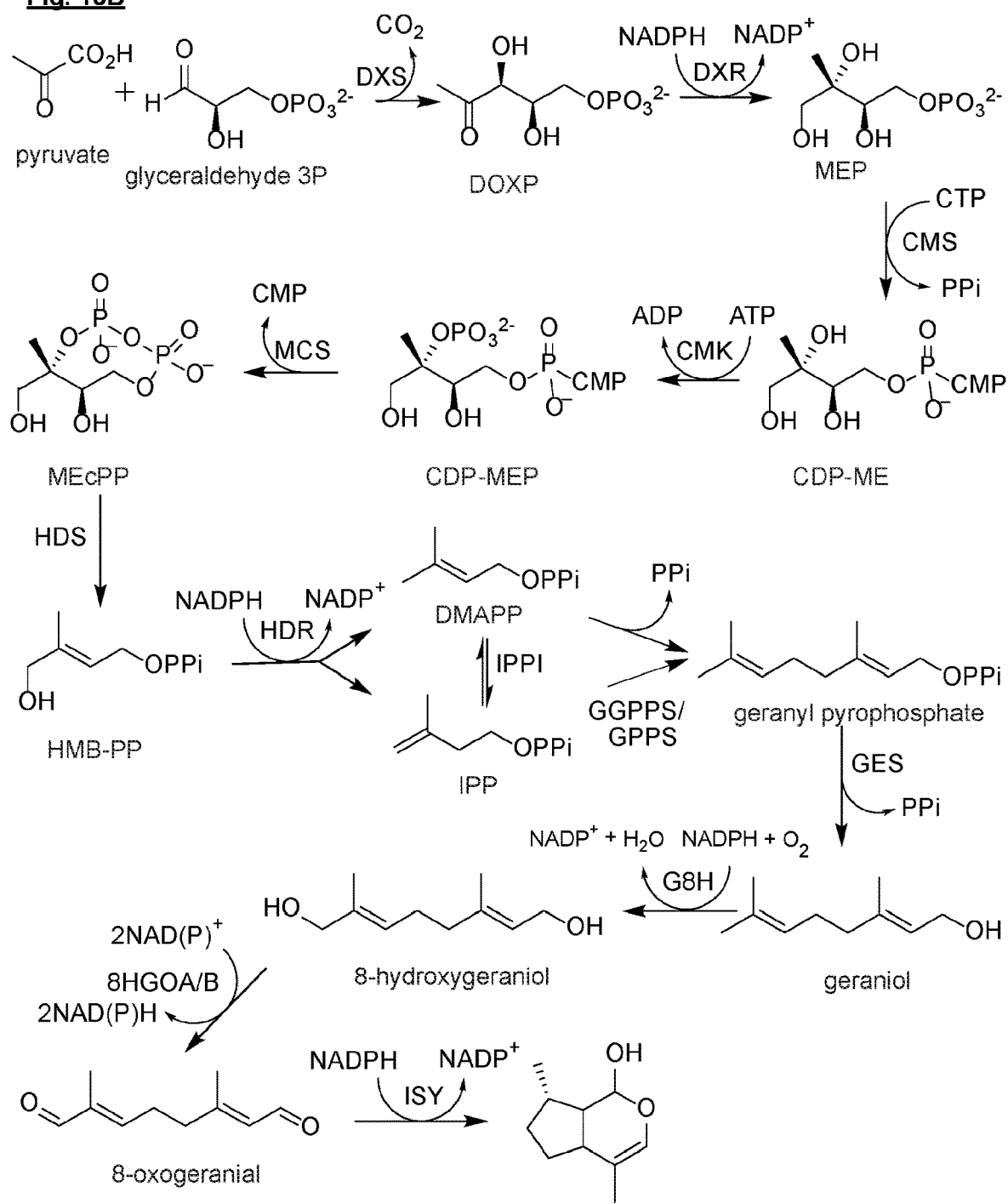
Figure 13C:
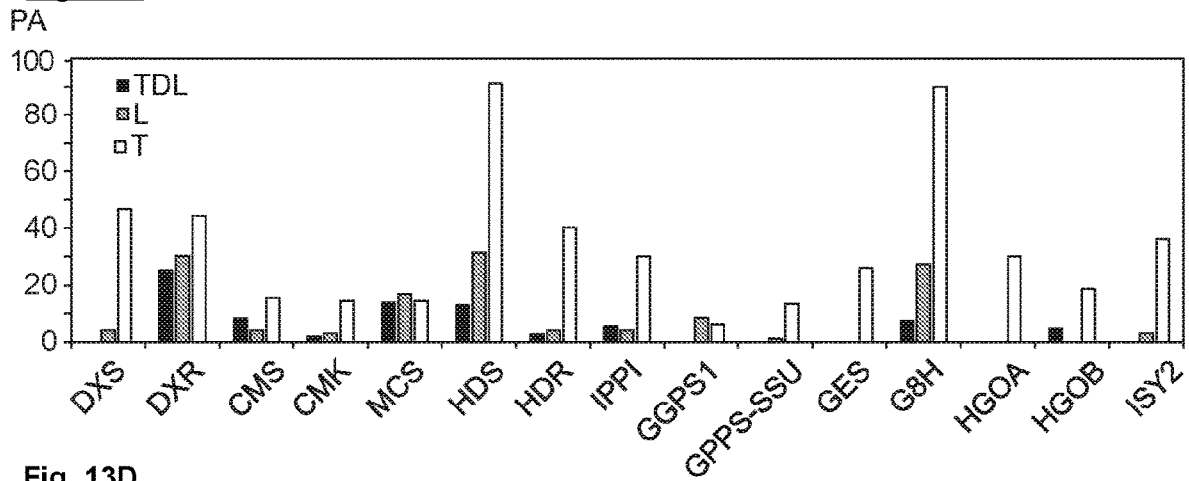

We obtained proteomes for *Nepeta mussinii* trichomes, leaves and trichome-depleted leaves (FIG. 13A). Comparison of these proteomes enabled identification of trichome enriched proteins. This approach was validated by the identification of trichome enriched enzymes from upstream isoprenoid biosynthesis (the 2-C-methylerythritol 4-phosphate (MEP) pathway) and iridoid biosynthesis (FIG. 13B, C).

Figure 13D:
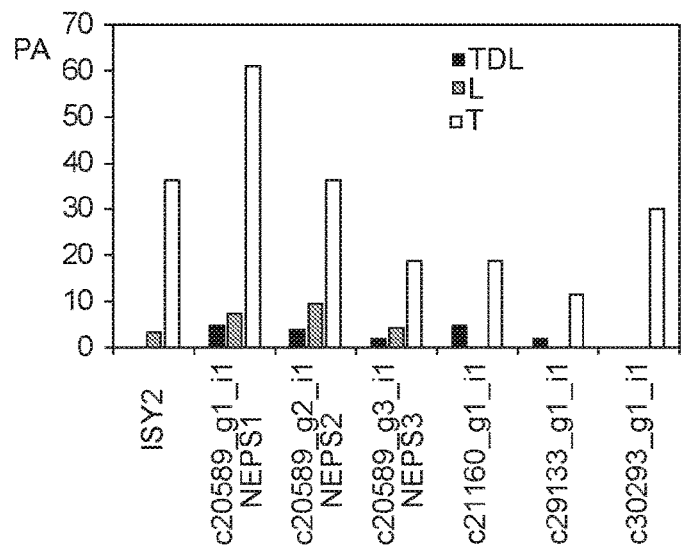
Figure 13E:
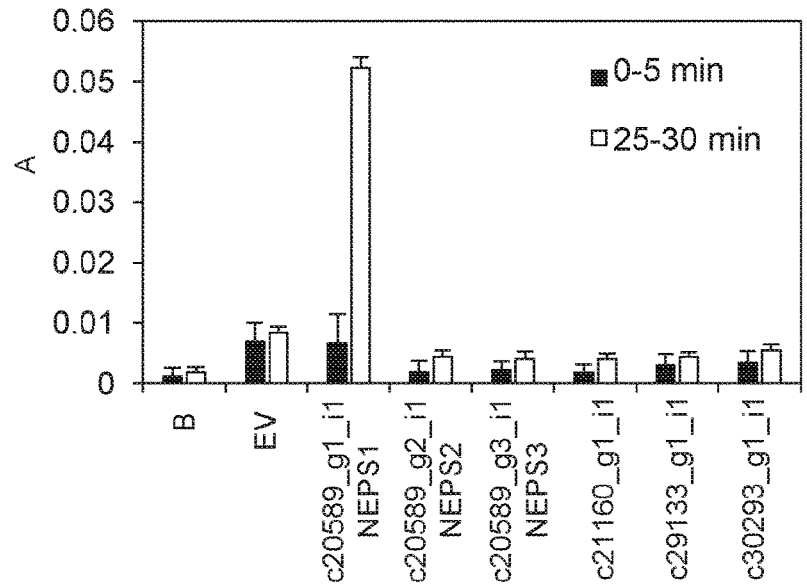

As a starting point, we initially used these proteomes to identify the enzyme that converts nepetalactol 4 to nepetalactone 1, an $NAD^+$ dependent enzyme. An enzyme with such activity had previously been isolated from the trichomes of *Nepeta mussinii* but its sequence was not identified. Six trichome enriched dehydrogenase genes were cloned and recombinantly expressed in *E. coli* (FIG. 13D, Table 1). Of these, one demonstrated cis-trans-nepetalactol 4a dehydrogenase activity (FIG. 13E).

The active enzyme is a short-chain reductase (SDR), part of the SDR110C family, a large and diverse family of NAD-dependent dehydrogenases often associated with plant secondary metabolism. Consequently, it was named Nepetalactol-related SDR 1 (NEPS1). NEPS1 could catalyse the $NAD^+$-dependent dehydrogenation of either cis-trans-nepetalactol 4a or cis-cis-nepetalactol 4b to the corresponding nepetalactones 1a and 1b (FIG. 3A-C, FIG. 14A, Table 2). Whilst the overall catalytic efficiency was slightly greater for dehydrogenation of 4a, 4b was turned over with twice the rate. This ratio of activities was in accordance with characterisation of the native enzyme.

Figures 15B, 15C:
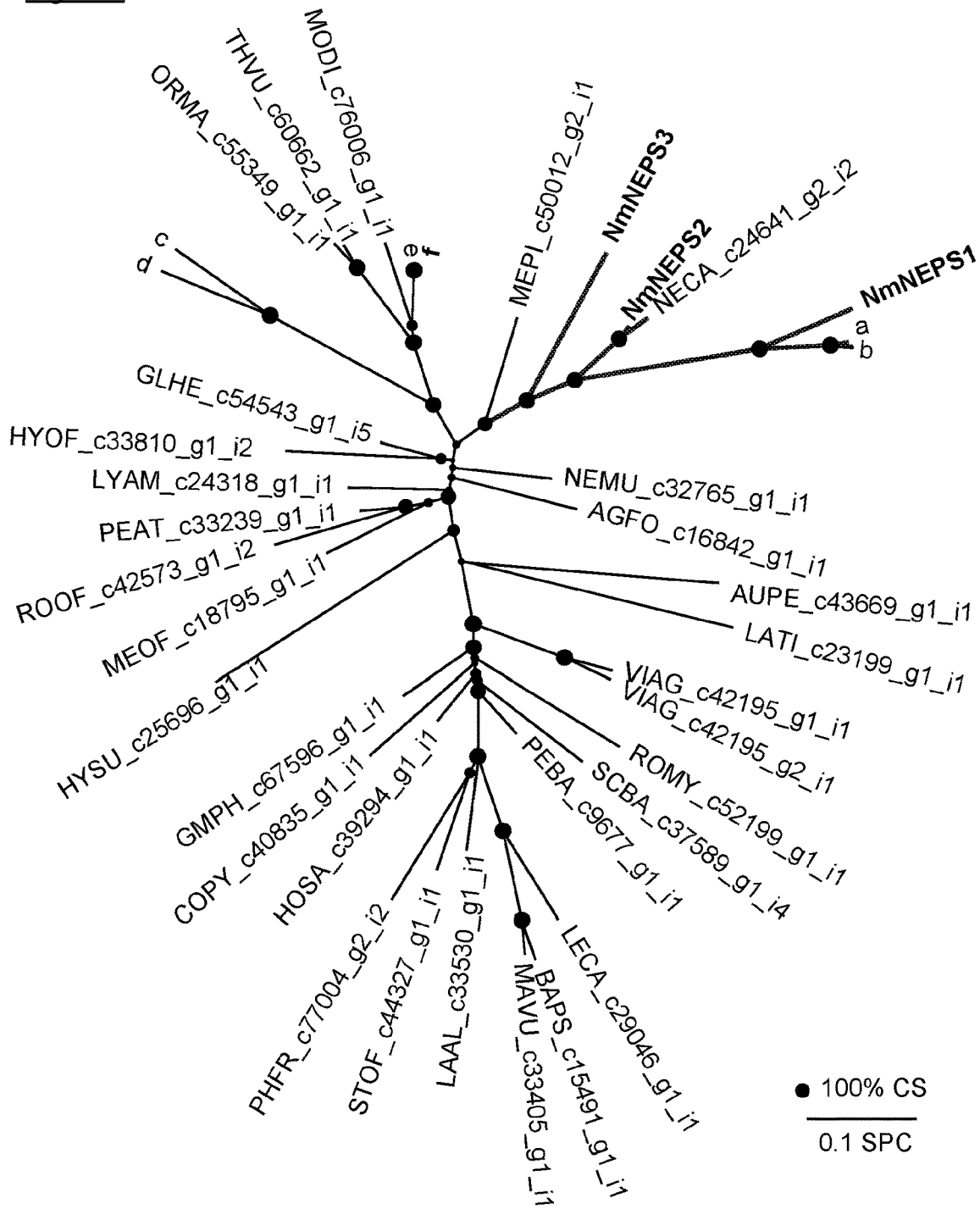

Sequence analysis of NEPS1 and the remaining dehydrogenase candidates revealed two additional trichome enriched paralogs of NEPS1, NEPS2 and NEP3 (FIG. 15A,B). Phylogenetic analysis revealed that these three proteins have a close evolutionary relationship and are found uniquely within the *Nepeta* lineage (FIG. 15C). Therefore, we hypothesised that NEPS2 and NEP3 also play a role in nepetalactone biosynthesis. Consequently, NEPS1-3 enzymes were assayed with a variety of nepetalactone related compounds and precursors such as nepetalactol 4, iridodials 5 and 8-oxogeranial 2 (FIG. 16). However, besides the NEPS1 activities described above, no other notable activities were observed for NEPS1-3.

NEPS Activities in Conjunction with ISY

Figure 3E:
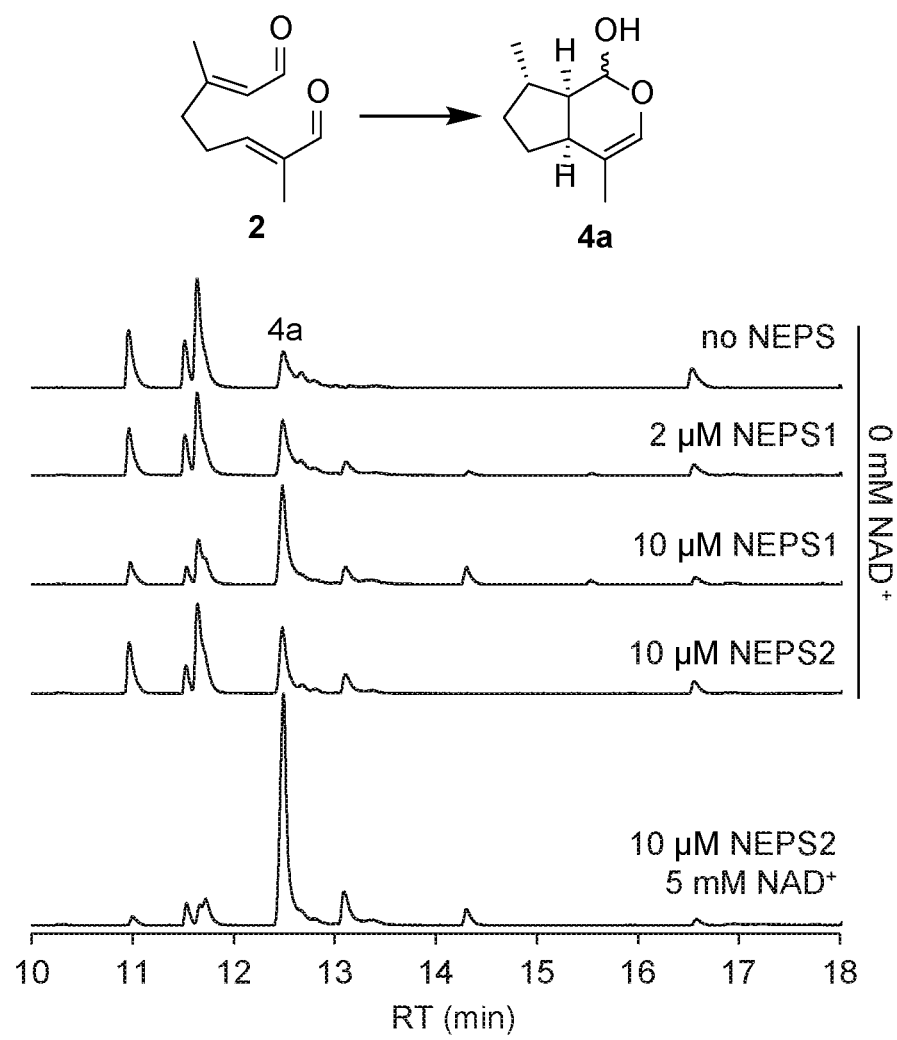

As described above, mechanistic investigations of ISY led us to hypothesise that a separate cyclase enzyme may act on the activated intermediate 3 that is generated by ISY. To test whether NEPS act as such cyclases, we performed one-pot cascade reactions combining NEPS enzymes with the ISY catalysed reduction of 8-oxogeranial 2 (FIG. 3A, D, E). As anticipated, addition of NEPS1 and excess $NAD^+$ led to the formation of cis-trans-nepetalactone 1a (FIG. 3D, FIG. 14B), though unexpectedly ISY iridodial side products 5 were diminished. Remarkably, addition of NEPS3 to ISY and 8-oxogeranial 2 led to the formation of cis-cis-nepetalactol 4b. A combination of NEPS1 and NEPS3 led to the production of cis-cis-nepetalactone 1b. Adjusting enzyme and cofactor concentrations revealed that NEPS1 and NEPS2 promoted the formation of cis-trans-nepetalactol 4a at the expense of iridodial 5 (FIG. 3E). The products observed indicated that the NEPS enzymes are cyclases (FIG. 3A), capable of accepting 3, the product of ISY, and cyclising it to 4a (NEPS1 and 2) or 4b (NEPS3). NEPS1 can then oxidise 4a and 4b into 1a and 1b respectively. The activities of NEPS enzymes did not appear to differ when tested with CrISY or NmISY2, suggesting that protein-protein interactions between ISYs and NEPS do not play a role in the system (FIG. 17).

The cyclisation of 3 into 4 is a non-oxidoreductive net [4+2] cycloaddition. The cyclase activities of NEPS also do not appear to be oxidoreductive. Investigation into the co-factor dependence of the ISY-NEPS3 reactions demonstrated this: $NAD^+$ concentrations were not limiting to overall reaction conversions, suggesting that $NAD^+$ was not consumed (FIG. 18). Furthermore, NEPS3 was active in the absence of supplemented $NAD^+$, though addition did improve activity. It appeared that although $NAD^+$ is not turned over by NEPS3 during cyclisation it may promote the enzyme's catalytic ability, perhaps through stabilisation of the protein structure.

NEPS Activities with S-8-Oxocitronellal

To verify the NEPS activities, reactions were conducted with S-8-oxocitronellal 6 and without ISY (FIG. 4). High concentrations of buffer were employed to promote the formation of 3, the proposed NEPS substrate, from 6. In these conditions, the previously observed activities of NEPS were recapitulated (compare FIG. 4B to FIG. 3D).

Figure 4A:
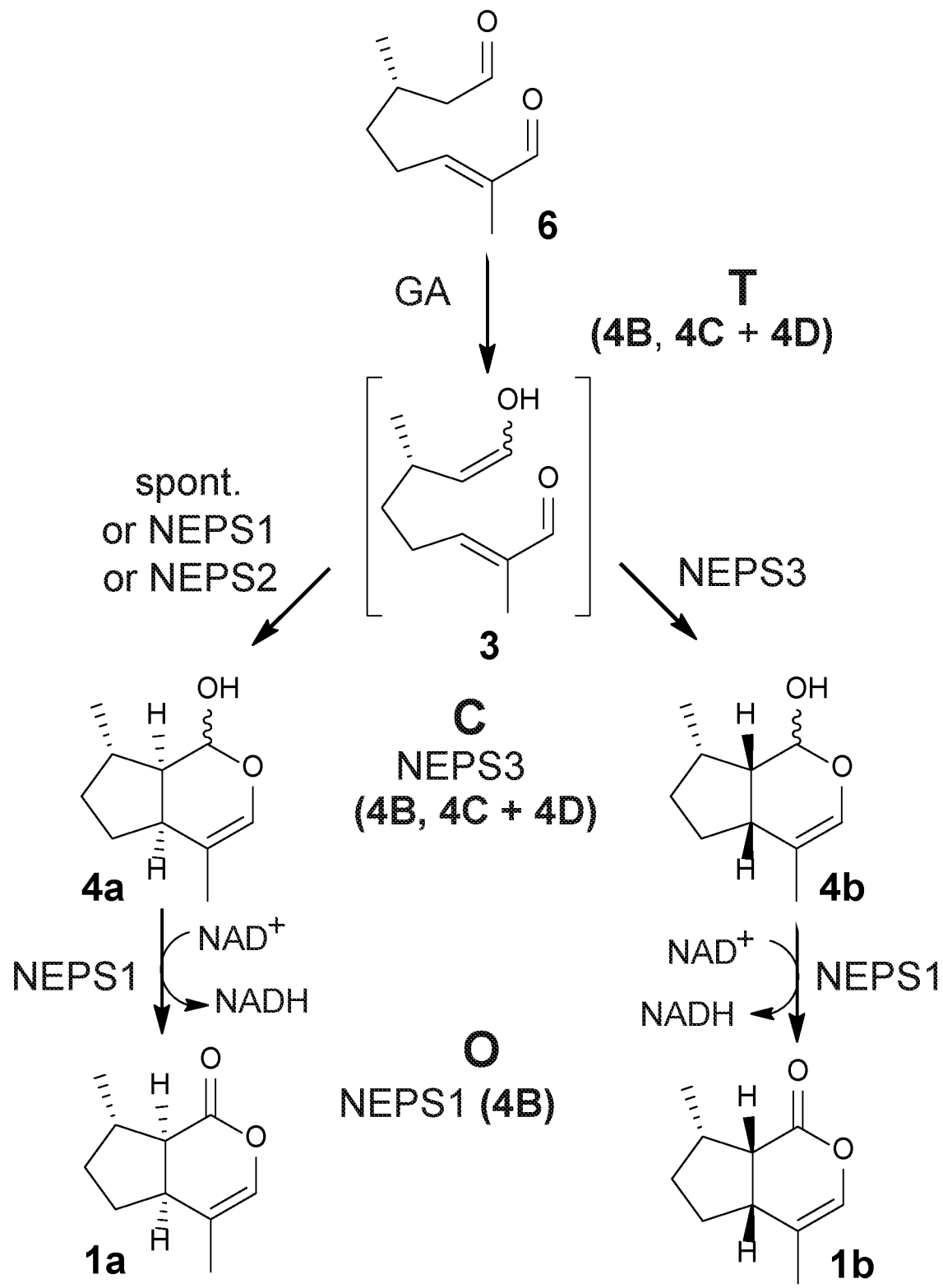
Figure 4B:
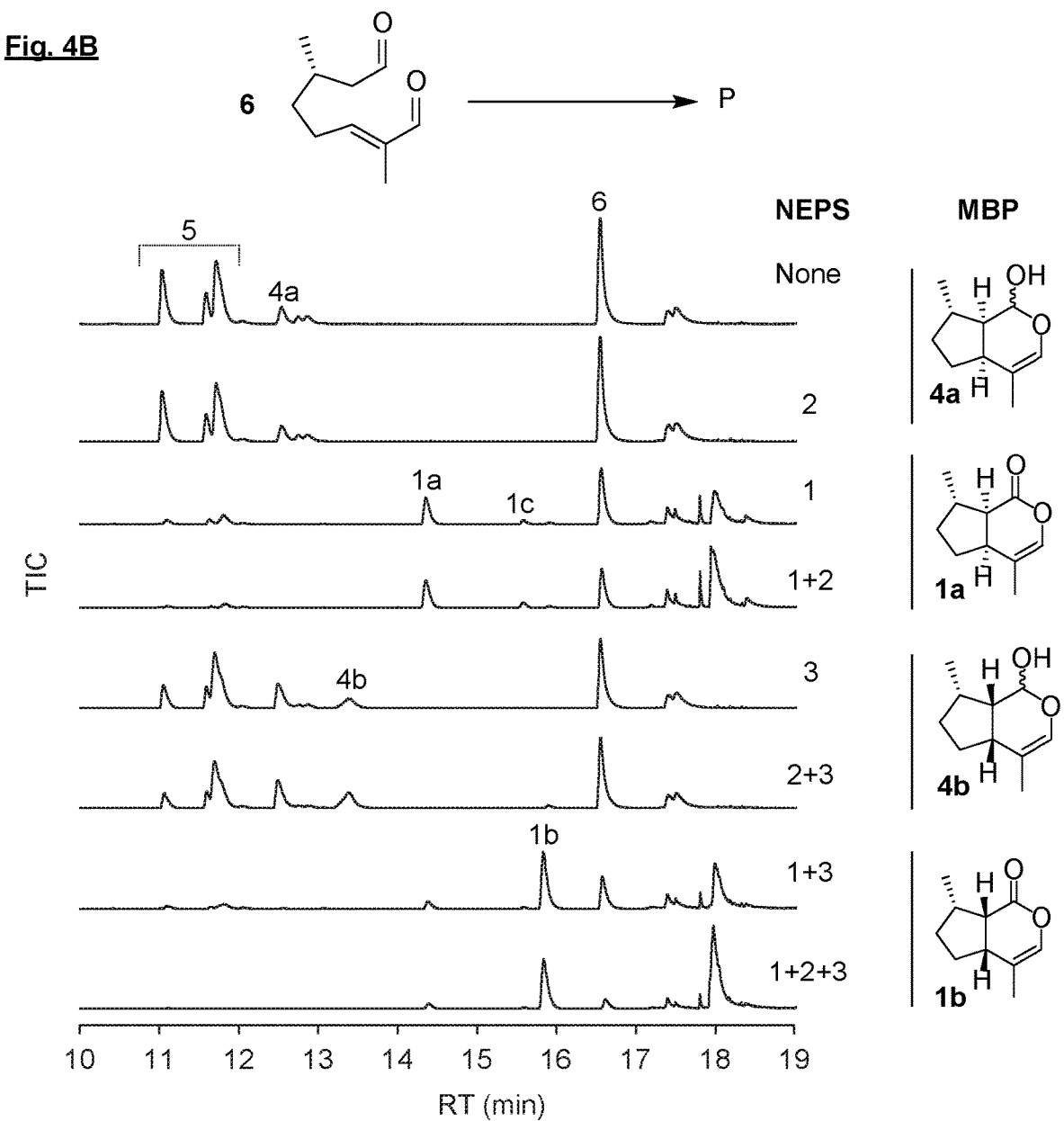
Figure 4C:
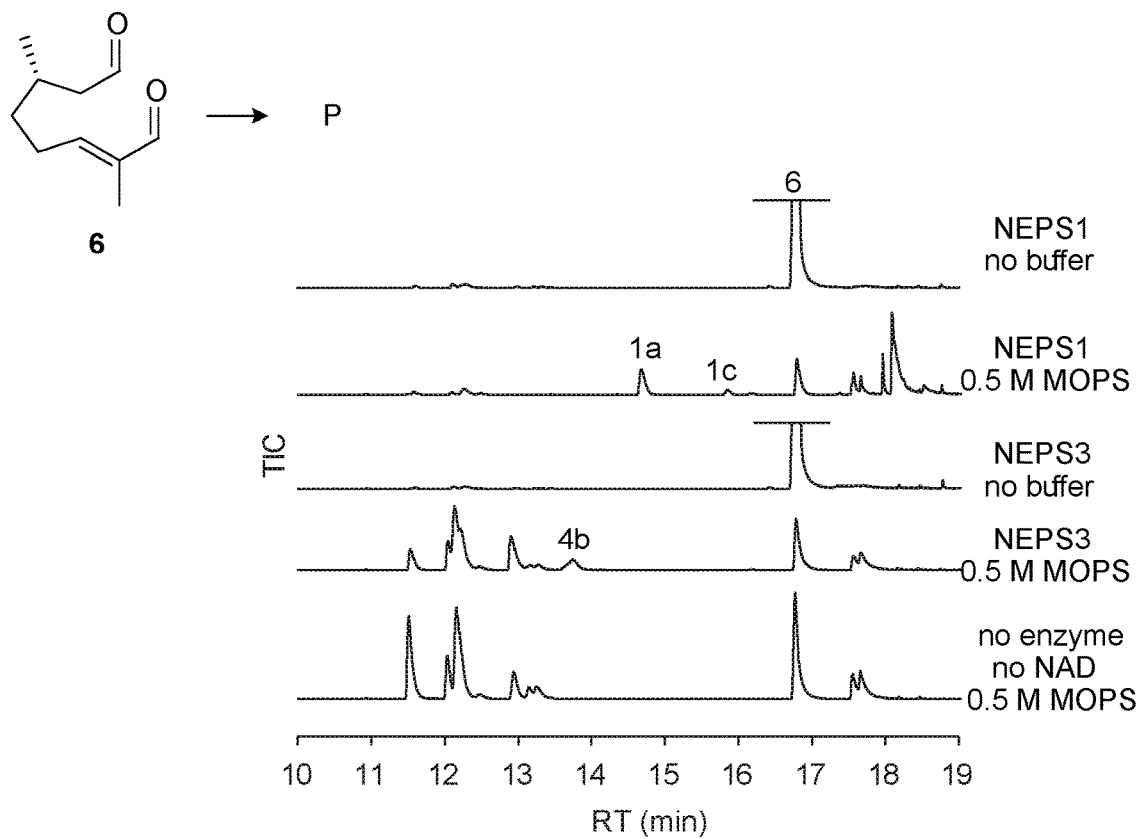

Neither NEPS1 nor NEPS3 were active when incubated with 6 in the absence of buffer (FIG. 4C). Buffer was necessary for activity, supporting the notion that that 6 is not the key substrate, but the tautomer 3 is. Further evidence for this was obtained by adding CrISY to reactions containing NEPS and 6—the pattern of products observed implied NEPS were binding to 6 without turning it over (FIG. 19).

Figure 4D:
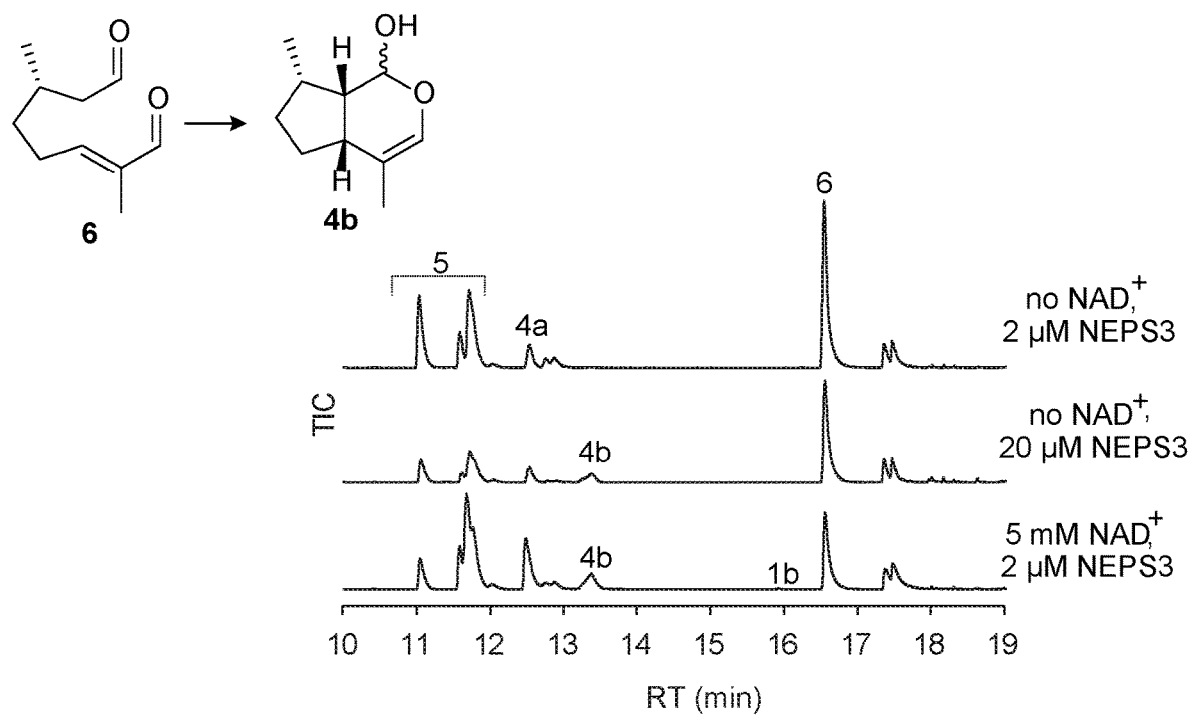

Support for the non-oxidoreductive nature of the NEPS3 cyclisation came from incubating NEPS3 with 6 and buffer in the absence of supplemented $NAD^+$ or NADPH: formation of cis-cis-nepetalactol 4b was still observed (FIG. 4D). As noted above, addition of $NAD^+$ does promote the reaction, though it is not necessary for activity. Interestingly, at high $NAD^+$ concentrations, trace quantities of 1b are observed (FIG. 4D, also FIG. 3D). Overall, NEPS reactions with 6 support the notion of 3 as the substrate and add further evidence for a non-oxidoreductive cyclisation (FIG. 4A).

Structure and Mechanism of NEPS Enzymes

To understand the mechanism of the NEPS3 cis-cis cyclisation reaction, we obtained an X-ray crystal structure of NEPS3 bound to $NAD^+$ (6F9Q, Table 3). In common with structural homologs, it forms a homotetramer with 222 symmetry, with the four active centres contained entirely within individual protomers (FIG. 20A). Efforts to generate an apo or ligand bound structure were unsuccessful, as were efforts to crystallise NEPS1. Despite the fact that NEPS3 appears to function primarily as a non-oxidoreductive cyclase, its structure is characteristic of classical SDRs, with $NAD^+$ bound in the typical fashion (FIG. 20B,C). Although evidence suggests $NAD^+$ is not turned over by NEPS3 during cyclisation, the co-factor appears important for the enzyme structure as it was required for crystallisation and it is bound by multiple H-bonds by the protein.

Homology models of NEPS1 and NEPS2, based on the NEPS3 structure, were generated to enable comparison of the enzyme active sites (FIG. 5). Whilst NEPS1 and NEPS2 have a typical SDR catalytic tetrad (N-Y-K-T/S), NEPS3 lacks the theronine/serine and instead has a glycine (G152). In addition, NEPS3 features H-bonding between active site residues S153 and P190, absent from both NEPS1 and NEPS2 due to the presence of a proline in place of the serine.

Interestingly, the NEPS3 structure appeared to feature a chloride anion bound to the amide NH and side chain of S154. Based on the presence of the chloride, and the similarity to the substrate oxyanion binding site in CrISY, this position may be a substrate oxyanion binding site (FIG. 20C). This site appears to be absent in NEPS1 and 2 due to the steric hindrance of the leucine side chain present in the equivalent position.

Figure 21A:
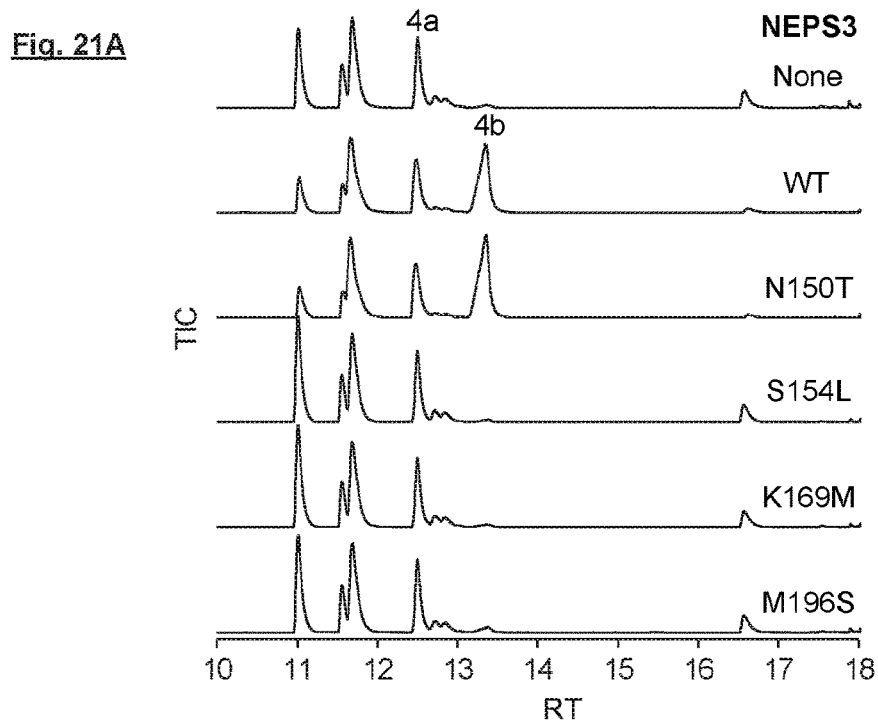
Figure 21B:
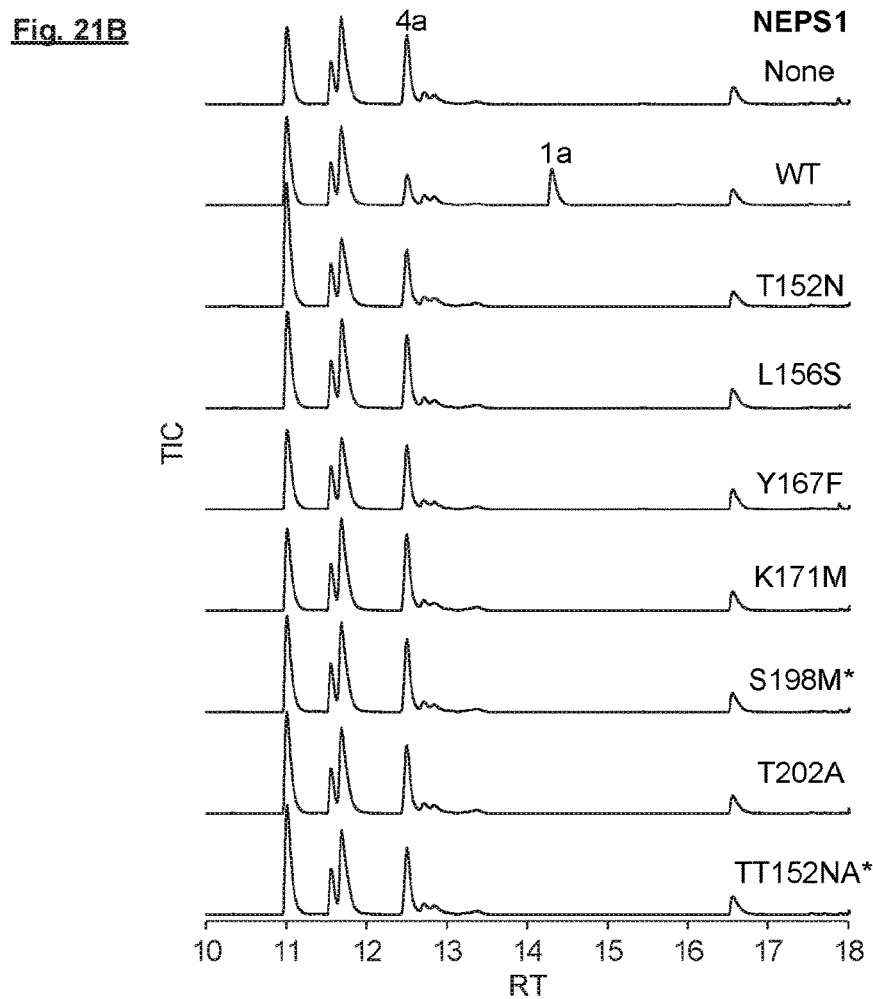
Figure 21C:
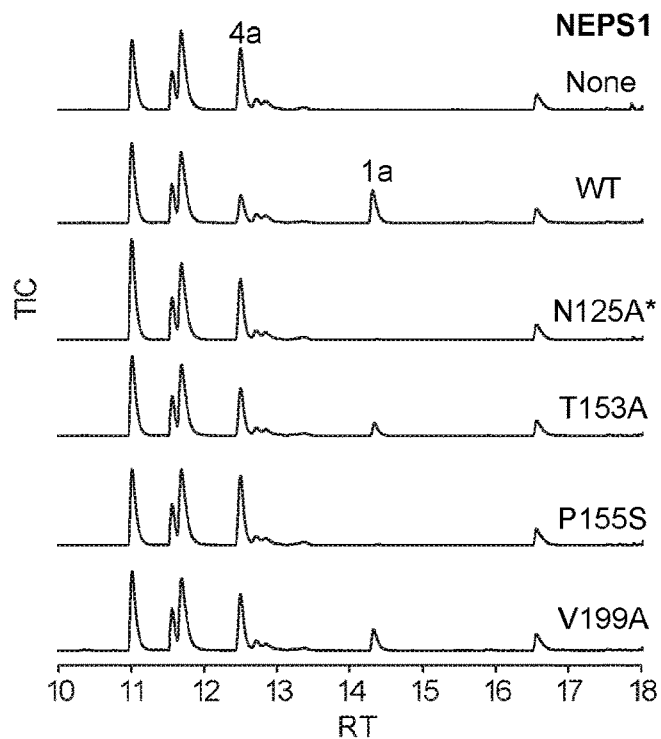
Figure 21D:
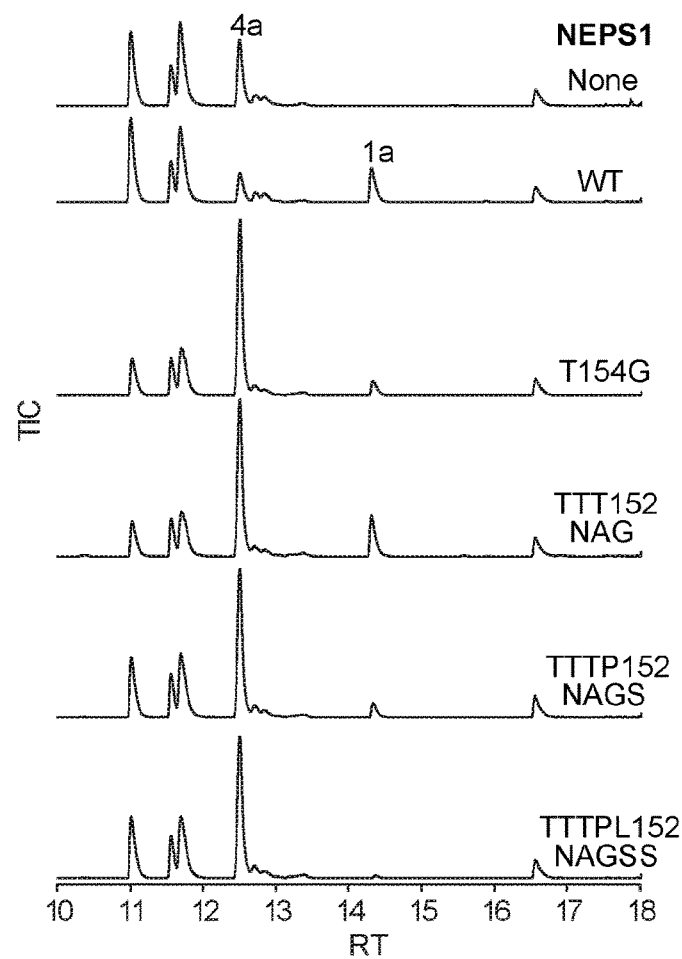

Active site residue roles in NEPS1 and NEPS3 were probed via mutational screens (Table 4). NEPS3 was especially sensitive to mutation, with several active site substitutions abolishing detectable soluble expression (A151T, G152T, S153P, Y165F). These mutations may have disrupted the H-bonding network in the active site, reducing protein stability. Of the mutations yielding soluble protein, only N150T maintained native levels of activity, whilst S154L, K169M and M196S had a severe reduction or complete loss of activity (FIG. 21A). Several NEPS1 variants had no detectable formation of 1a, signifying that these may be functionally important residues (T152N, L156S, Y167F, K171M, S198M, T202A, FIG. 21B). Near-WT levels of 1a were identified in samples with the variants V110A, T153A, V199A, whilst trace quantities of 1a was identified with N125A and P155S (FIG. 21C). Most interesting were variants containing the T154G substitution, which produced considerably greater quantities of 4a than WT (FIG. 21D).

Figure 6A:
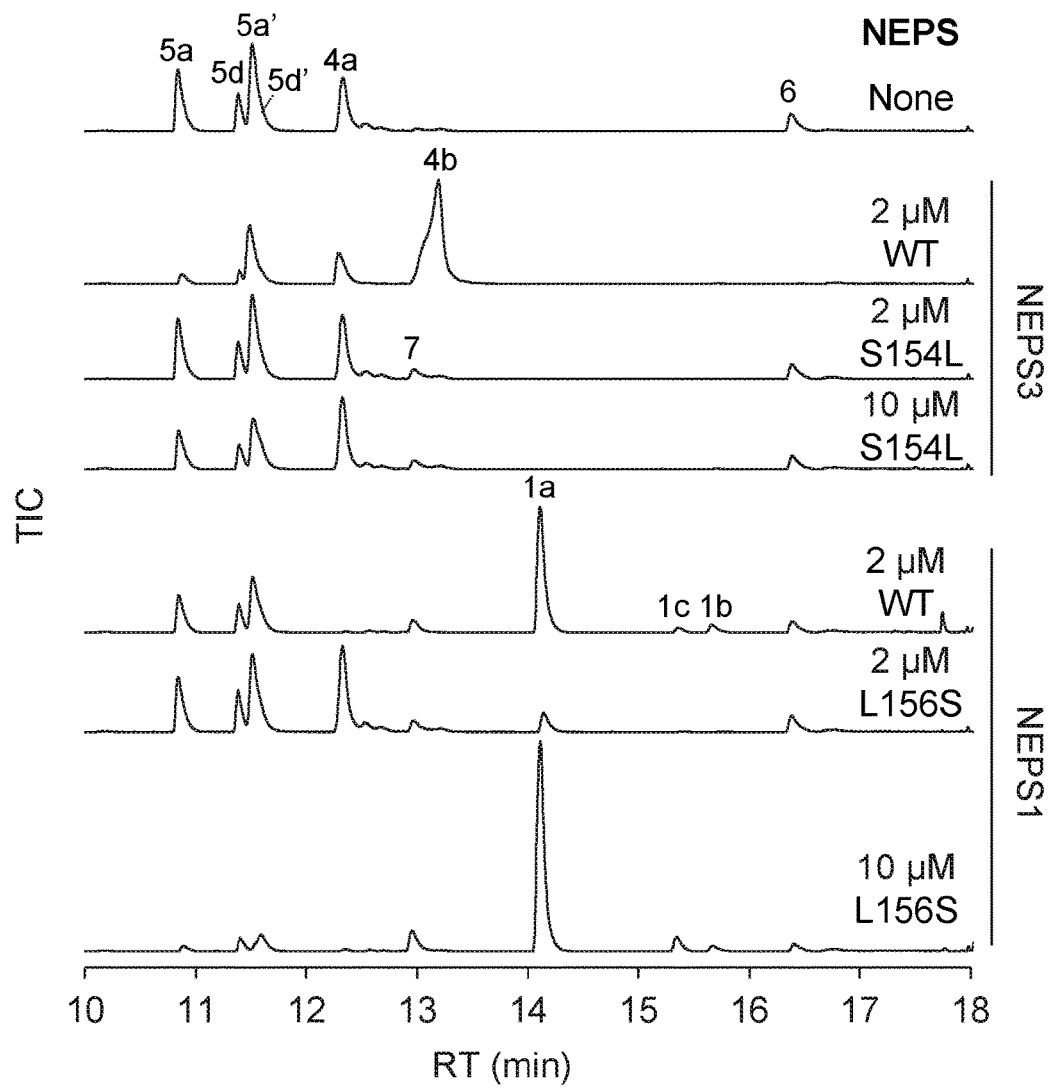

The role of the NEPS3 S154 putative oxyanion binding site was examined by further characterisation of NEPS3-S154L and the complementary NEPS1-L156S variant. NEPS3-S154L (2 M) demonstrated no detectable cis-cis cyclase activity, though at higher enzyme concentrations (10 µM), the variant appeared to promote the formation of cis-trans-nepetalactol 4a (FIG. 6A). The complementary substitution in NEPS1, L156S, reduced dehydrogenase activity but failed to increase the formation of cis-cis-nepetalactol 4b or lactone 1b (FIG. 6A). The NEPS3-S154 oxyanion binding site therefore appears necessary for cis-cis cyclisation in NEPS3 but its introduction into NEPS1 is not sufficient to establish cis-cis cyclisation activity. In contrast, the removal of S154 from NEPS3 appears to switch the cyclisation selectivity from cis-cis to cis-trans.

Figure 6B:
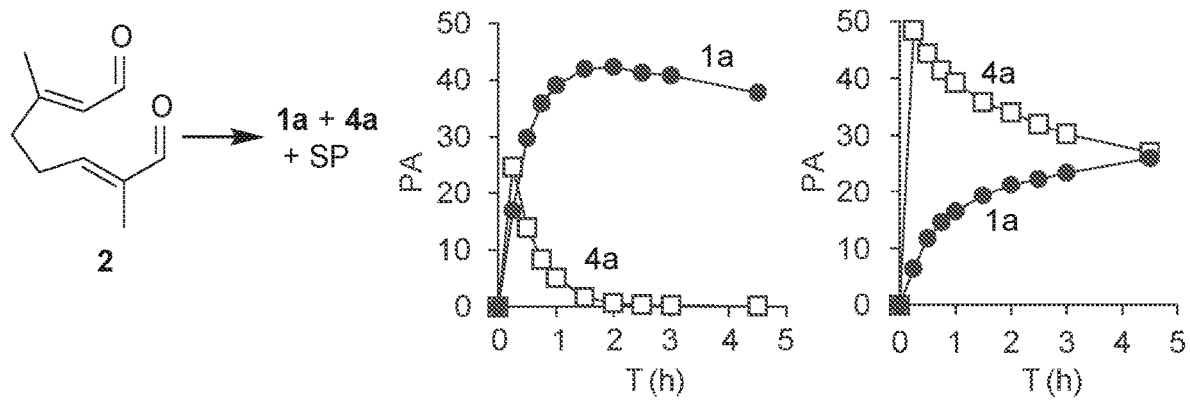
Figure 6C:
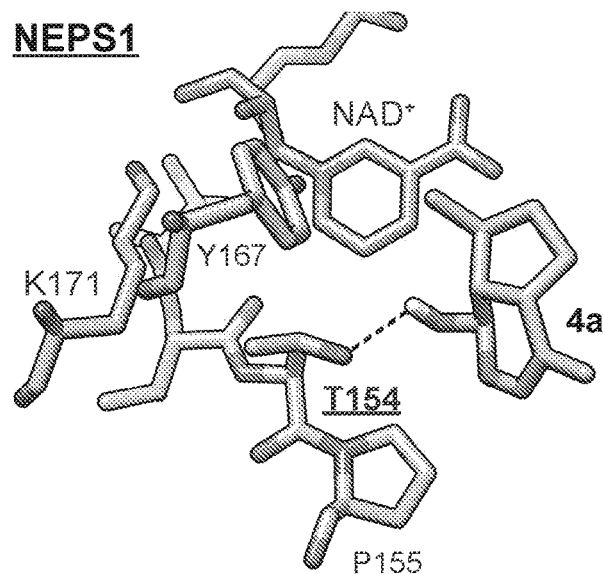
Figure 6D:
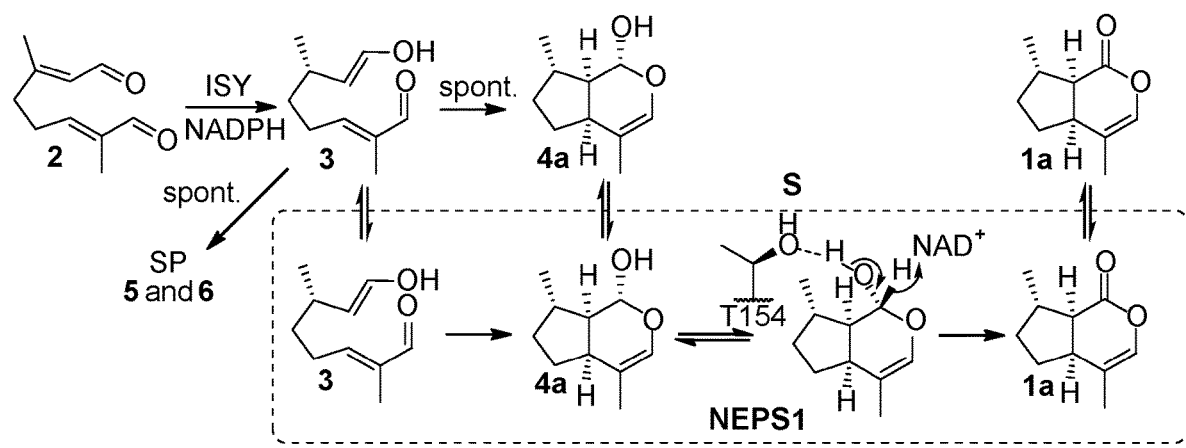
Figure 22A:
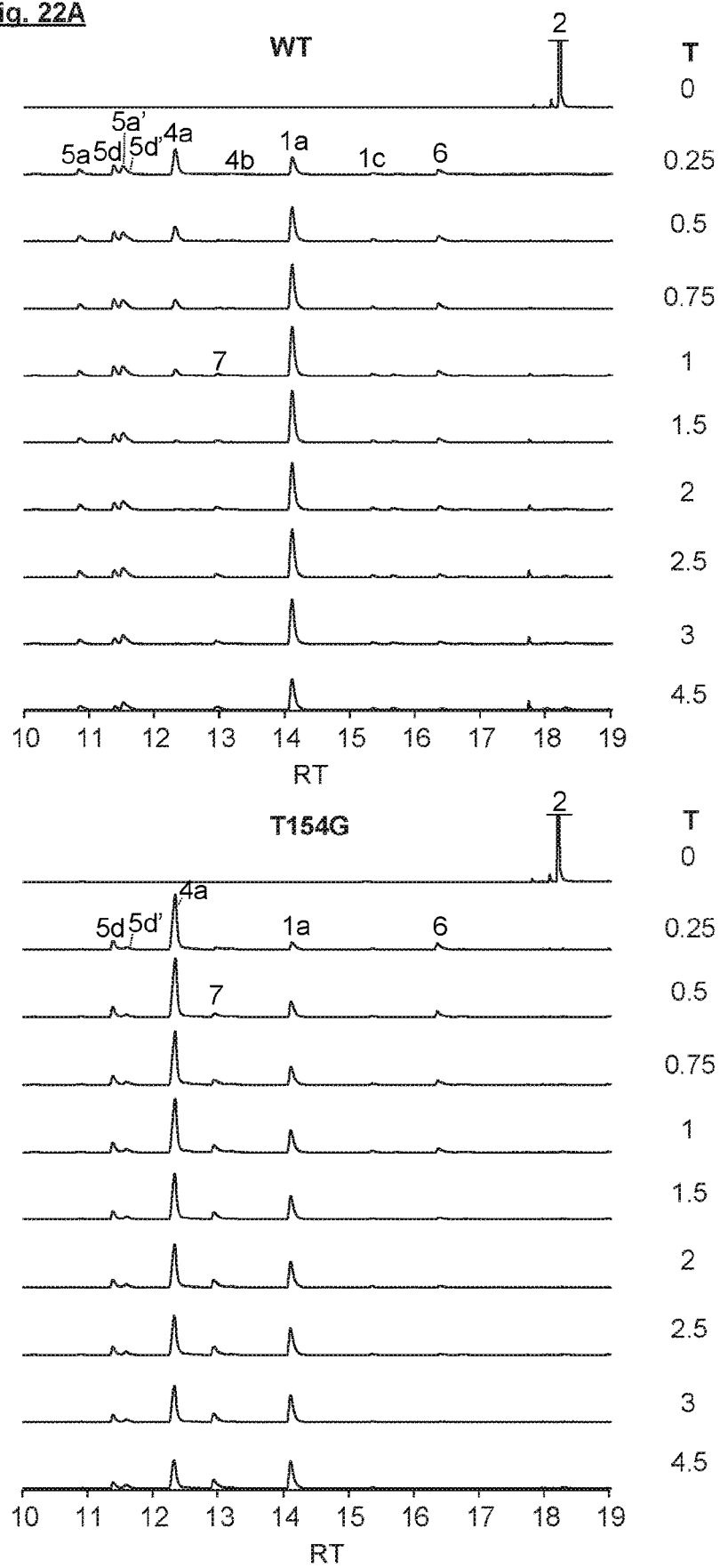
Figure 22B:
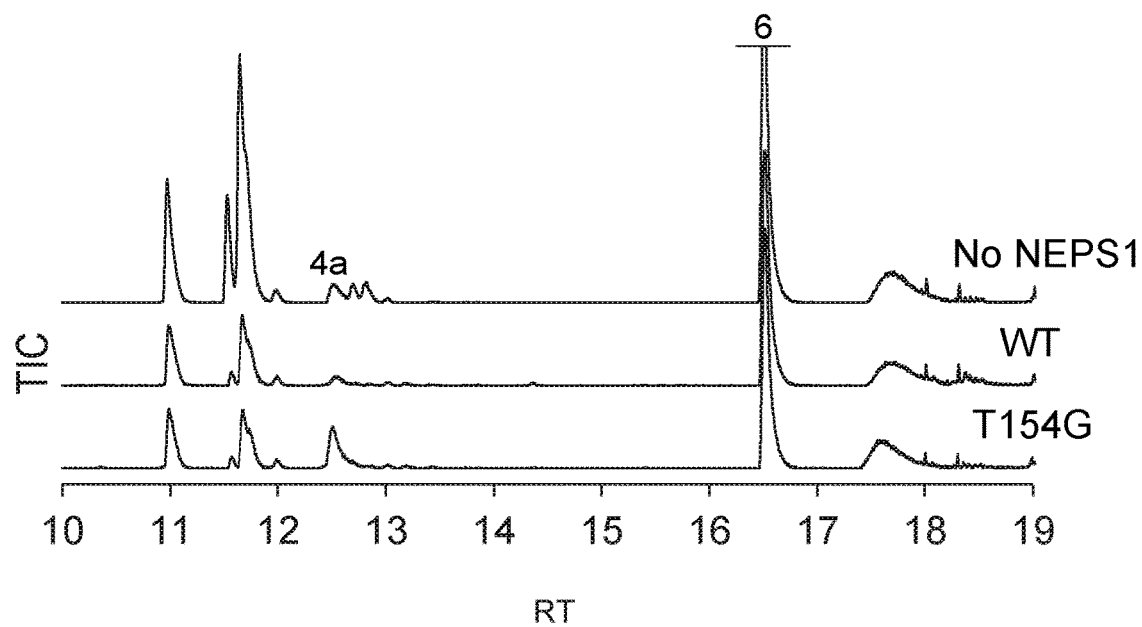

The NEPS1-T154G variant was also characterised further. Compared to NEPS1-WT, the variant accumulated 4a and showed impaired formation of 1a (FIG. 6B, FIG. 22A). This loss of dehydrogenase activity appears to be a result of a 150-fold increase in $K_m$ for 4a caused by the T154G substitution (Table 2). This result indicates that T154 interacts with 4a during or prior to the dehydrogenation step; a putative binding mode is provided by docking calculations (FIG. 6C). Interestingly, the variant appears to have slightly enhanced cyclisation activity: reactions with T154G show minimal formation of cis-trans-iridodial 5a side products (FIG. 22A) and the variant is also able to form detectable levels of 4a from 6 in buffer without supplemented cofactors (FIG. 22B). This improved cyclisation may be a consequence of poor 4a binding-if 4a is released rapidly then there is more available enzyme to bind 3 and catalyse its cyclisation (FIG. 6D).

Discussion

Here we demonstrate how a mechanistic analysis of ISY led to the hypothesis that a separate cyclase is responsible for setting the stereochemistry of the iridoid framework. A comparative proteomic analysis allowed discovery of these cryptic enzymes. These NEPS enzymes demonstrate the plasticity and innovation characteristic of plant secondary metabolism enzymes. NEPS3, for example, is an SDR by structure and sequence yet its primary catalytic activity is non-oxidoreductive; $NAD^+$ is utilised not as a co-substrate but as a protein structural scaffold. Interestingly, at very high $NAD^+$ concentrations NEPS3 can catalyse dehydrogenation with low catalytic efficiency, a phenomenon that may be a glimpse into its evolutionary past.

Due to its inherent reactivity, in situ generation of the substrate 3 was required to reveal the activity of the NEPS enzymes. Reactive non-isolable substrates appear elsewhere in plant specialised metabolism, including monoterpene indole alkaloid and lignan biosynthesis. NEPS are reminiscent of dirigent proteins, proteins in lignan biosynthesis that control the stereoselective cyclisation of a reactive intermediate that is generated by a separate enzyme. There may be similar undiscovered steps in other metabolic pathways; these cannot be revealed in simple one substrate, one enzyme assays, but require multi-enzyme cascade strategies, making discovery of such enzymes challenging.

Based on the structural and mutant data, we propose that NEPS1/2 and NEPS3 catalyse cyclisation in different fashions. NEPS1/2 appear to allow the enol 3 to proceed down a default 'uncatalysed' path, forming the same product as formed in water (FIG. 2). Their key role in the cyclisation appears to be to protect the intermediate from general acid catalysed tautomerisation; there is no evidence to suggest that NEPS1/2 mechanisms do not mirror the stepwise Michael addition seen in solution. NEPS3, on the other hand, has specific 7S-cis-cis-nepetalactol cyclase activity, binding to 3 possibly via S154 and exerting steric and/or electrostatic influence to enable formation of the cis-cis stereochemistry. Further analysis is required to determine whether NEPS3 catalyses the [4+2] cyclisation in a stepwise or concerted manner (i.e. Michaelase or Diels-Alderase). The contrast between the 'passive' NEPS1/2 and 'active' NEPS3 mechanisms mirrors the of dichotomy of intrinsic substrate reactivity versus enzyme influence in canonical terpene synthase mechanisms.

Phylogenetic analysis suggests the NEPS enzymes are unique to Nepeta. Yet ISYs from other organisms also do not catalyse iridoid cyclisation. Thus, it is likely that different cyclases, unrelated to NEPS, are operating in other iridoid producing species. The absence of such cyclases from iridoid pathways reconstituted in microbial organisms may have negatively impacted yields. The NEPS cyclases described here, especially NEPS2, a dedicated cis-trans cyclase, can be incorporated into such systems to improve yield.

We have revealed the biosynthetic origin of cis-trans and cis-cis-nepetalactone, compounds in *Nepeta* responsible for cat attraction and insect repellence. In doing so we have discovered three novel enzymes: two dedicated cyclases and one multifunctional cyclase-dehydrogenase. The structure of one of these enzymes reveals it has re-purposed a dehydrogenase structure for a different catalytic function. We have shown that iridoid biosynthesis involves uncoupled activation and cyclisation: a reactive, non-isolable enol is formed by reduction and cyclised by separate enzymes. Such findings will contribute to synthetic biology metabolic reconstructions and inform the de novo design of (bio)synthetic pathways; they also highlight the dynamic and innovative nature of plant natural product biosynthesis.

Materials and Methods
Data Availability

The sequences of *N. mussinii* NEPS enzyme have been deposited in GenBank/EMBL/DDBJ with the accession codes: MG677124 (NmNEPS1), MG677125 (NmNEPS2) and MG677126 (NmNEPS3). The $NAD^+$ bound NmNEPS3 (7S-cis-cis-nepetalactol cyclase) X-ray structure has been deposited in the PDB with the accession code 6F9Q. The mass spectrometry proteomics data have been deposited to the ProteomeXchange Consortium via the PRIDE partner repository with the dataset identifier PXD008704.

Chemicals

All chemicals were purchased from Sigma-Aldrich unless noted. Compound identity and purity were determined using NMR spectroscopy, using a Bruker 400 MHz/54 mm Ultra-Shield Plus, long hold time automated spectrometer at 400 MHZ (1H-NMR) and 100 MHZ (13C-NMR).

8-oxogeranial 2 was synthesized. Geranyl acetate (5 g, 29.5 mmole) was added to a mixture of selenium dioxide (433 mg), dichloromethane (12.5 mL) and tert-butyl hydroperoxide (12 mL, 70% w/v water), and stirred at room temperature for 30 h. The mixture was diluted in $Et_2O$ (up to 40 mL) and then filtered through celite, washed with $Na_2S_2O_3$ (60 g/L, 3×40 mL), sat. $NaHCO_3$ (40 mL), $H_2O$ (2×40 mL) and brine (40 mL). The organic fractions were dried over $MgSO_4$/charcoal and concentrated in vacuo. The crude product was purified by silica flash chromatography using hexane and 0-30% v/v EtOAc in a gradient elution. Fractions were concentrated in vacuo to yield 8-oxogeranyl acetate (1.45, 27%) and 8-hydroxygeranyl acetate (1.42, 26%). 8-oxogeranyl acetate (1 g, 4.75 mmole) was then added to a mixture of $K_2CO_3$ (329 mg, 0.5 eq), MeOH (9.5 mL) and $H_2O$ (0.5 mL). The reaction was stirred at room temperature for 2 h, then $H_2O$ (60 mL) and brine (20 mL) were added. This was extracted into EtOAc (9×20 mL) and concentrated in vacuo. The compound was purified by silica flash chromatography using hexane and 0-50% v/v EtOAc in a gradient elution. Fractions were concentrated in vacuo to yield 8-oxogeraniol (0.57 g, 71%). Finally, to 8-oxogeraniol (500 mg, 2.97 mmole) was added dichloromethane (35 mL), $NaHCO_3$ (1.5 g, 6 eq) and Dess-Martin periodinane (1.51 g, 1.2 eq). this mixture was stirred on ice for 1 h. The crude product was partially purified by silica chromatography using $Et_2O$/hexane and then $Et_2O$ as eluant. Fractions were concentrated in vacuo to yield partially purified 8-oxogeranial (416 mg). A portion of this was purified further using Florisil gel chromatography and $Et_2O$/hexane and then $Et_2O$ as eluants. The identity and purity of the final 8-oxogeranial compound was confirmed by NMR and GC-MS.

S-8-oxocitronellal 6 was synthesised. S-citronellal (1 g, 6.48 mmole) was added to a mixture of selenium dioxide (115 mg), dichloromethane (2.5 mL) and tert-butyl hydroperoxide (2.6 mL, 70% w/v water). The mixture was stirred at room temperature. After 48 h, the mixture was diluted with $Et_2O$ (to 10 mL) and filtered over celite. The filtrate was washed with aq. $Na_2S_2O_3$ (60 g/L, 3×10 mL), sat. $NaHCO_3$ (10 mL), $H_2O$ (2×10 mL) and brine (10 mL). The organic fractions were dried over $MgSO_4$/charcoal and concentrated in vacuo. The crude product was purified by silica flash chromatography using a hexane and 0-30% v/v EtOAc in a gradient elution. The fractions containing the product S-8-oxocitronellal were identifiable by TLC by their strong UV absorbance and anisaldehyde staining. These fractions were combined and concentrated to yield S-8-oxocitronellal 6 (152 mg, 14%). The identity and purity of this compound was confirmed by NMR and GC-MS. This compound contained approximately 10% of an inseparable impurity tentatively identified as S-8oxocitronellal-1-di-tert-butyl acetal.

2,3,6,7-tetrahydro-8-oxogeranial 7 was obtained by biotransformation. 8-oxocitronellal 6 (10 μmole) was added to a mixture (20 mL) containing CrISY (0.5 μM), NEPS3 (2 μM), NADPH (1 mM), $NAD^+$ (5 mM) and MOPS (0.5 M, pH 7.5). The reaction was incubated at 30° C. for 16 h and then extracted with EtOAc (3×20 mL). The organic fractions were washed with brine (20 mL), dried with $MgSO_4$ and concentrated in vacuo to yield 2,3,6,7-tetrahydro-8-oxogeranial (0.4 mg, 23%). The identity of this compound was confirmed by NMR and GC-MS. The compound was not completely pure, but was sufficient for use as a GC-MS compound standard.

Cis-trans-nepetalactone 1a was isolated from *Nepeta fassinii* "Six Hills Giant" (Burncoose Nurseries, Gwennap, Redruth, Cornwall, TR16 6BJ, UK). Cis-cis-nepetalactone 1b was isolated from *Nepeta mussinii* "Snowflake" (Burncoose Nurseries, Gwennap, UK). Trans-cis-nepetalactone 1c was isolated from catnip oil. Cis-trans-nepetalactol 4a was obtained by DIBAL-H reduction of 1a. Cis-cis-nepetalactol 4b was obtained by DIBAL-H reduction of 1b. Cis-trans-iridodial 5a was obtained by acid hydrolysis of cis-trans-nepetalactol 4a. Cis-cis-iridodial 5b was obtained by acid hydrolysis of cis-trans-nepetalactol 4a. Trans-cis-iridodial 5c was obtained by DIBAL-H reduction of trans-cis-nepetalactone 1c. Chemical identity and purity of these compounds were verified by NMR and GC-MS as reported previously. Trans-trans-iridodial 5d was obtained. First cis-cis-nepetalactone 1b was epimerised to trans-trans-nepetalactone and then this compound underwent DIBAL-H reduction to yield 5d.

Proteome Analysis

Whole leaves from *N. mussinii* (1.5 g×4, obtained from Herbal Haven, Coldhams Farm, Rickling, Saffron Walden, CB11 3YL, UK) were placed into a 50 mL centrifuge tube and to this was added powdered dry ice (approximately 20 mL). This was vortexed (1 min, 20,000 rpm) and the dry material was poured through meshes (200 μm and 100 μm) and the material passing through the meshes was collected. To maximise yield, leaves and tubes were washed with cold isolation buffer (200 mM sorbitol, 25 mM HEPES, 5 mM $MgCl_2$, 5 mM succinic acid, 1 mM EGTA, 0.5 mM $NaH_2PO_4$, 5 mM DTT, 2 mM sucrose, pH 7) and this was filtered through a mesh (100 μm) and collected. Samples were inspected by light microscopy to determine success of the extraction step. The samples were centrifuged (700×g, 10 min), the supernatant removed to yield a pellet containing trichomes. Leaves and trichome-depleted leaves were frozen in liquid nitrogen and homogenised with a pestle and mortar. Trichomes were resuspended in extraction buffer (1 mL, 0.1 M Tris-HCl pH 8, 2% w/v SDS, 30% w/v sucrose, 5% v/v 2-mercaptoethanol, 1 mM phenylmethylsulfonyl fluoride), vortexed and homogenised by sonication (10 s ON, 10 s OFF, 20 cycles). Tris-buffered phenol (1 mL) was added to homogenised samples, then vortexed (10 min) and centrifuged (10,000×g, 10 min). The upper layer was obtained and to this was added extraction buffer (1 mL) and the mixture vortexed (5 min) and centrifuged (10,000×g, 10 min). The upper layer was transferred to a new tube and to this, four volumes of methanol/0.1 M NH$_4$Ac (1:1, −20° C.) were added, the sample mixed and then incubated at −20° C. overnight. The precipitated protein was pelleted by centrifugation, and the pellet was washed twice with methanol/0.1 M NH$_4$Ac (1:1, −20° C.) and then with acetone (−20°) C. The acetone was removed and the pellet air-dried.

Protein pellets from leaves and depleted leaves were dissolved in 5% sodium deoxycholate (SDC), 50 mM phosphate buffer pH 8, pellets from trichomes in 1% SDC, 50 mM phosphate buffer pH 8. Protein concentration was determined using the Direct Detect® spectrometer (Merck Millipore, UK). The total protein amount was 400 μg for leaves, 225 μg for depleted leaves and 20 μg for trichomes. Samples were treated with DTT and iodoacetamide to reduce and alkylate cysteine residues. The total trichome sample and 50 μg of the leaf samples were digested with trypsin. SDC was removed by acid precipitation, and aliquots of approx. 1 μg were used for data dependent LC-MS/MS analysis on an Orbitrap-Fusion™ mass spectrometer (Thermo Fisher, Hemel Hempstead, UK) equipped with an UltiMate™ 3000 RSLCnano System using an Acclaim PepMap C18 column (2 μm, 75 μm×500 mm, Thermo). The samples were loaded and trapped using a pre-column which was then switched in-line to the analytical column for separation. Peptides were eluted with a gradient of 6-38% acetonitrile in water/0.1% formic acid at a rate of 0.4% min$^{-1}$. The column was connected to a 10 μm SilicaTip™ nanospray emitter (New Objective, Woburn, MA, USA) for infusion into the mass spectrometer. Data dependent analysis was performed using a parallel HCD/CID fragmentation method with the following parameters: positive ion mode, orbitrap MS resolution=60 k, mass range (quadrupole)=300-1500 m/z, MS2 in ion trap, threshold 2e4, isolation window 1.6 Da, charge states 2-5, inject for all available parallelisable time with 3 s cycle time, AGC target 2e3, max inject time 100 ms, dynamic exclusion 1 count within 10 s and 60 s exclusion, exclusion mass window±7 ppm. MS scans were saved in profile mode while MSMS scans were saved in centroid mode.

Raw files from the Orbitrap were processed with MaxQuant (version 1.5.3.30) to generate recalibrated peaklist files which were used for database searches with the Mascot search engine (version 2.4.1, Matrixscience, London). A predicted peptide library was generated from the *N. mussinii* transcriptome by translation of predicted open reading frames (minimum size 100 bp, ATG start codon, start/stop codons can be outside sequence). This predicted peptide library was annotated with phmmer using Swiss-Prot reference proteins (http://www.uniprot.org/) and used for the Mascot database search using trypsin/P with 2 missed cleavages, carbamidomethylation (C) as fixed and oxidation (M), acetylation (protein N-terminus), and deamidation (N,Q) as variable modifications. Mass tolerances were 6 ppm for precursor ions and 0.6 Da for fragment ions. Mascot search results were imported into the Scaffold software and the Scaffold quantitative value (normalised total spectra) was used for a pairwise comparison between trichome and trichome-depleted leaves samples using Fisher's exact test with Benjamini-Hochberg multiple test correction. MEP pathway enzymes were putatively identified by functional annotation. Nepetalactol dehydrogenase candidates were selected by the following criteria: functionally uncharacterised, statistically significant trichome enrichment (p<0.05) and enzyme class EC 1.1.1.-(oxidoreductase, acting on alcohols, NAD(P)$^+$ dependence).

Cloning cDNA was obtained. Primers for dehydrogenase candidates were designed based on the transcriptome sequence and 5'-overhangs were added for cloning into the pOPINF vector (forward: 5'-AAGTTCTGTTTCAGGGCCCG-3' (SEQ ID NO: 13), reverse: 5'-CTGGTCTAGAAAGCTTTA-3' (SEQ ID NO: 14)). The primers were used to PCR amplify the genes from the cDNA. These were purified from an agarose gel and then cloned into a linearised POPINF vector using an InFusion HD cloning kit (Clontech). Plasmid sequences were verified with Sanger sequencing. Cloned sequences NEPS2 and NEPS3 did not precisely match full length sequences from the transcriptome, but appeared to contain regions from multiple transcripts. The poor assembly of these genes is indicative of close paralogs or alternative splicing. SoluBL21 *E. coli* cells (Genlantis) were transformed with the plasmids for expression.

Mutations were introduced into the NEPS1 and NEPS3 genes by PCR. First, two gene fragments were amplified. The first fragment was cloned using the gene specific forward primer from the original cloning and a reverse primer ending 5' of the mutation site (reverse mutation primer). The second fragment cloned employed a forward mutation primer encompassing the mutation site (forward mutation primer) and the reverse primer from the original cloning. The fragments were gel-purified and then a third PCR, using the original gene specific forward and reverse primers, was used to assemble the fragments. This genelength amplicon was gel-purified and then cloned into the pOPINF vector using an InFusion HD cloning kit (Clontech). Plasmid sequences were verified with Sanger sequencing. SoluBL21 cells (Genlantis) were transformed with the plasmids for expression.

Enzyme Expression and Purification

Expression strain cells containing the plasmids of interest were grown overnight (LB media, 10 mL, 100 μg/mL carbenicillin). 2×YT media with 100 μg/mL carbenicillin was innoculated with overnight culture (5% v/v) and grown at 37° C. until OD$_{600}$=0.5. The culture was then grown at 18° C. until OD$_{600}$=0.6-0.8 and then protein production was induced with addition of IPTG (500 μM). The cells were incubated at 18° C. for 16 hours before harvesting by centrifugation (4000×g, 10 min). If the pellets were not used immediately, they were washed in PBS before storage at −20° C.

For the lysate assays used for screening for dehydrogenase activity, cultures (1 mL) of each dehydrogenase candidate were grown as described above. Cell pellets were resuspended in BugBuster MasterMix (100 μL) (Merck), incubated at 4° C. for 10 min and then centrifuged (20,000× g, 10 min). Supernatant lysate (1 μL) was added to a mixture (100 μL total) containing cis-trans-nepetalactol 4a (0.5 mM), NAD$^+$ (1 mM) and sodium phosphate buffer (50 mM, pH 8.8). The reactions were followed for 30 min on a FLUOStar Omega multiplate reader (BMG Labtech) using absorbance at 340 nm (positioning delay 0.2 s, 22 flashes per well, 32 s cycle time, 1 s 200 rpm shaking each cycle). For each candidate, two control samples lacking both NAD$^+$ and 4a or lacking just 4a were included. Control reactions with empty vector were also measured. Averages of absorbance measurements between 0-5 min and 25-30 min were obtained and compared to identify increases in absorbance (i.e. formation of NADH).

For initial screening of NEPS1 and NEPS3 variants, cultures (10 mL) of each NEPS variant were grown as described above. Cell pellets were resuspended in Bug-Buster MasterMix (1 mL, with complete EDTA-free protease inhibitors (Roche)), incubated at 4° C. for 20 min and then centrifuged (20,000×g, 20 min). Nickel-NTA agarose (100 µL) (Qiagen) was washed in binding buffer (50 mM Tris-HCl PH 8, 50 mM glycine, 5% v/v glycerol, 0.5 M NaCl, 20 mM imidazole, 1 mM DTT), added to the supernatant lysate and the mixture was incubated at 4° C. for 1 h, gently rocking. The mixture was centrifuged (1000×g, 1 min) and the supernatant discarded. The Ni-NTA pellet was washed twice with 1 mL binding buffer, and then elution buffer (50 mM Tris-HCl pH 8, 50 mM glycine, 5% v/v glycerol, 0.5 M NaCl, 500 mM imidazole, 1 mM DTT) was added (500 µL). The mixture was centrifuged (1000×g, 1 min), the supernatant collected and filtered (Ultrafree-MC VV Centrifugal Filter, Merck). The buffer was exchanged into sample buffer (20 mM HEPES pH 7.5, 150 mM NaCl) by four concentration-dilution steps using a centrifugal filtration (Amicon Ultra 10 kDa MWCO, (Merck)). The proteins were aliquoted and flash frozen in liquid nitrogen and stored at −80° C. SDS-PAGE analysis and spectrophotometric analysis (absorbance at 280 nm) was used to check purity and approximate quantity of protein.

For all enzyme assays, excluding the activity screens described above, and for crystal trials, cultures (1 L) were grown as described above. Cell pellets were resuspended in lysis buffer (binding buffer plus complete EDTA-free protease inhibitors (Roche) and 0.4 mg/mL lysozyme) and incubated at 4° C. for 30 min. The lysate was then centrifuged (35,000×g, 45 min, 4°) C. and the supernatant filtered (Minisart NML Plus 0.7 µm GF (Sartorius)). The filtrate was applied to a 5 mL His Trap HP column (GE Lifesciences) attached to a ÄKTA pure system (GE Lifesciences). The column was washed with binding buffer until no protein could be detected coming off the column (detection using absorbance at 280 nm). The protein of interest was then eluted by application of elution buffer to the column. The eluted protein was pooled, filtered (PES membrane, 0.45 µm (Starlab)) and further purified by size-exclusion chromatography on a Superdex 200 16/60 GF column (GE Lifesciences). During this process, the protein was exchanged into sample buffer. Eluant fractions were analysed by SDS-PAGE, and those containing the protein of interest were pooled, concentrated by centrifugation (Amicon 10 kDa MWCO), flash frozen in liquid nitrogen and stored at −80° C. Protein purity was confirmed by SDS-PAGE analysis. Protein concentration was determined by spectrophotometric analysis at 280 nm using extinction coefficients calculated by ProtParam (http://web.expasy.org/protparam/).

Enzyme Assays

Kinetics and dehydrogenase activity measurements were conducted spectrophotometrically on a PerkinElmer Lambda 35 instrument at a wavelength of 340 nm and in cuvettes with 1 cm path length. The reactions were conducted at 25° C. and with 50 mM HEPES pH 8.0, 100 NaCl. Reactions were initiated by addition of the enzyme, and absorbance values were recorded at a rate of 1 Hz. Enzyme concentration was varied from 0.025-0.25 µM to maintain a linear rate. The R software environment was used to fit linear initial rates over the first 20 s of the enzyme reaction. For Michaelis-Menten experiments, at least 8 data points were obtained for each substrate combination. The Michaelis-Menten equation was fitted to the data points in R by the nls function to obtain values for the kinetic parameters. Kinetic parameters are reported as a best fit estimate±SE. For activity measurements with NADP$^+$ and NADH, single substrate concentrations were employed. Velocity values (in italics) are provided as a mean of triplicate measurements±standard deviation from the mean.

End-point assays with purified enzymes were conducted at a total volume of 100 µL. Reactions using either 8-oxogeranial 2 or 8-oxocitronellal 6 as a substrate contained 1% v/v MeCN. In experiments examining the effect of buffer concentrations, enzymes were diluted with water. Trace residual concentrations of sample buffer in the enzyme sample were too low to effect product profiles. All reactions were conducted at 30° C. Reactions containing 8-oxogeranial 2 as a substrate were incubated for 3 h, whilst reactions with 8-oxocitronellal 6 were incubated for 16 h, unless noted. At reaction termination, a camphor standard (10 µL, stock 1 mM in MeCN) and EtOAc (100 µL) were added. The reactions were vortexed, centrifuged (10,000×g, 10 min) and the organic layer was used in GC-MS analysis. The concentrations of components in reactions varied extensively and so for each reaction the Figure or Figure legend describe the exact conditions employed.

Gas Chromatography-Mass Spectroscopy

Samples were injected in split mode (2 µL, split ratio 5:1) at an inlet temperature of 220° C. on a Hewlett Packard 6890 GC-MS equipped with a 5973 mass selective detector (MSD), and an Agilent 7683B series injector and autosampler. Separation was performed on a Zebron ZB5-HT-INFERNO column (5% phenyl methyl siloxane; length: 35 m; diameter: 250 µm) with guard column. Helium was used as mobile phase at a constant flow rate of 1.2 mL/min and average velocity 37 cm/s. After 5 min at 80° C., the column temperature was increased to 110° C. at a rate of 2.5 K/min, then to 280° C. at 120 K/min, and kept at 280° C. for another 4 min. A solvent delay of 5 min was allowed before collecting MS spectra at a fragmentation energy of 70 eV. An internal standard of (+)-camphor was used for retention time calibration. Chemically characterised standards were used to identify compounds by retention time and electron impact spectra.

Crystallisation and Data Collection

NEPS3 was purified as described above. The protein (7 mg/mL) was thawed and incubated with C3-protease (0.36 mg/mL) for 1 h at room temperature. The protein was filtered (Ultrafree-MC VV Centrifugal Filter) and passed through Nickel-NTA agarose, removing the cleaved His-Tag and tagged C3-protease. The eluant (NEPS3 without tag) was concentrated to 7 mg/ml (Amicon 10 kDa MWCO) in sample buffer. Crystals were formed using the hanging drop method (3 µL total, 1:2 protein:buffer, 1 mM NAD$^+$ final concentration), using a precipitant comprised of 29% w/v PEG 4000 with 0.1 M MES pH 6.5. The crystals were cryo-protected with crystallisation buffer containing 20% v/v ethylene glycol, then flash-cooled in liquid nitrogen using LithoLoops (Molecular Dimensions), and stored in Unipuck cassettes (MiTeGen) prior to data collection. Crystals were transferred robotically to the goniostat on beamline 103 at the Diamond Light Source (Oxfordshire, UK), and maintained at −173° C. with a Cryojet cryocooler (Oxford Instruments). X-ray diffraction data were recorded to 1.4 Å resolution using a Pilatus 6M hybrid photon counting detector (Dectris), then integrated and scaled using XDS, via the XIA2 expert system, and then merged in a primitive monoclinic unit cell using AIMLESS; the resultant data collection statistics are summarized in Table 3.

Structure Solution and Refinement

The majority of the downstream analysis was performed through the CCP4i2 graphical user interface (http://www.ccp4.ac.uk/). A molecular replacement template for the NEPS3 subunit was prepared from PDB entry 2BGK, with which it shares 42% sequence identity, using SCULPTOR. The high resolution of the X-ray data was indicative of a low solvent content, and a value of 40% was estimated for four copies of the ~28 kDa subunit in the asymmetric unit (ASU). Moreover, inspection of a self-rotation function revealed several non-crystallographic two-fold axes, in addition to the crystallographic two-fold. The functional unit of the template structure, secoisolariciresinol dehydrogenase, is a homotetramer with 222 symmetry, which prompted us to prepare an equivalent tetramer from the SCULPTOR output. The latter was used as the input for PHASER which produced a very convincing solution (TFZ score=15) in space group P21. This model was rebuilt with BUCCANEER and then improved with iterations of manual editing in COOT and refinement with REFMAC5. Initially, we had modelled elongated peaks of electron density, adjacent to the nicotinamide ring in each of the four independent active sites in the tetramer, as discretely disordered water molecules. However, after refinement, these were associated with significant amounts of positive difference electron density and they had refined temperature factor values significantly lower than those of the surrounding atoms, indicative of more electron dense species. Given that in each case the atom was within 3.6 Å of two backbone amides, it was re-assigned as a discretely disordered chloride ion (NaCl was present at 150 mM in the sample buffer). After refinement, the chloride ion temperature factors were comparable to, or slightly higher than, those of the surrounding atoms. The statistics of the final refined model, including analysis by MolProbity, are shown in Table 3. This model was deposited in the Protein Data Bank with accession code 6F9Q. Figures and structural alignments were made using UCSF-Chimera (http://www.rbvi.ucsf.edu/chimera/). Homology models of NEPS1 and NEPS2 were constructed using the iTasser server. NAD+ was added to the structures (using NEPS3 as a model) and then the complexes were energy minimised using the Yasara energy minimisation server. Docking calculations were performed with AutoDock Vina (exhaustiveness=8).

Phylogenetics and Sequence Analysis

Protein multiple sequence alignment NEPS and MpIPDH was performed with ClustalW2 and depicted with ESPript. For phylogenetic analysis, Lamiaceae and outgroup sequences were obtained from the Mint Genome Project (http://mints.plantbiology.msu.edu/, NCBI BioProject PRJNA359989). Sequences with homology to NEPS were identified by BLAST (https://blast.ncbi.nlm.nih.gov/). *Mentha* x *piperita* isopiperitenol dehydrogenase (MpIPDH, AY641428) was also included in the analysis. Prior to alignment, incomplete sequences and duplicated sequences were removed. The codon alignment was performed with MUSCLE, and then manually reviewed and curated to remove ragged ends. Phylogenetic tree inference was performed with IQ-Tree 1.5.4. First, the substitution model (TIM+I+G4) was determined by ModelFinder. The maximum likelihood tree was then determined heuristically over 146 iterations, and branch support values were calculated using ultrafast bootstrapping (1000 replicates). The tree was visualised in FigTree v1.4.3 (http://tree.bio.ed.ac.uk/software/figtree/).

Tables

TABLE 1

Primers used to clone dehydrogenase candidates from *N. mussinii* cDNA.

| Enzyme name | SwissProt Annotation | Original contig number | Contributing contigs (after sequencing) | Gene specific primer Forward | Gene specific primer Reverse |
|---|---|---|---|---|---|
| NEPS1 | Q5C919 | c20589_g1_i1 | | ATG GCA AGC ACT GCA AAT CC (SEQ ID NO: 63) | CTGA AGG AGC AAA GAA TGG TAA ACA AAG C (SEQ ID NO: 69) |
| NEPS2 | Q5C919 | c20589_g2_i1 | c47141_g1_i1 | ATG GGC AAC AAG AAG ACG C (SEQ ID NO: 64) | TGA TGT TGG TGC AAA GAA TGG T (SEQ ID NO: 70) |
| NEPS3 | Q5C919 | c20589_g3_i1 | c43881_g1_i1 | ATG GCT AAC AAT TCA GTG ATG ATG AAG (SEQ ID NO: 65) | TGC TGA ACC GAG GAG AAA TGG (SEQ ID NO: 71) |
| | Q6V4H0 | c21160_g1_i1 | | ATG GCG AAA TCA CCA GAA ACA G (SEQ ID NO: 66) | GTC GGC TTT CAG TGA ACC G (SEQ ID NO: 72) |
| | Q6V4H0 | c29133_g1_i1 | | ATG GCG AAA TCA GTG AAC GC (SEQ ID NO: 67) | ATC GGT TTC AGT CAG CGT ATT CC (SEQ ID NO: 73) |
| | P25141 | c30293_g1_i1 | | ATG GCC GAC AAC ACC AC (SEQ ID NO: 68) | GAA CTT GAT AAT AAC CTT GAC ACA ATC AGG (SEQ ID NO: 74) |

Primers were synthesised with vector specific overhangs as described in methods. Cloned sequences NEPS2 and NEPS3 did not precisely match full length sequences contigs from the transcriptome, but appeared to contain regions from multiple contigs. The poor assembly of these genes is indicative of close paralogs or alternative splicing.

TABLE 2

Kinetic parameters of NEPS1 dehydrogenase activity.

| Enzyme | Substrate | [Substrate] µM | Co-substrate | [Co-substrate] mM | $K_{cat}$ or V $s^{-1}$ | $K_m$ µM |
|---|---|---|---|---|---|---|
| NEPS1-WT | 4a | 0.25-100 | NAD+ | 1 | 0.148 ± 0.002 | 1.6 ± 0.1 |
| NEPS1-WT | 4b | 1-100 | NAD+ | 1 | 0.32 ± 0.01 | 4.9 ± 0.8 |
| NEPS1-WT | NAD+ | 1-250 | 4a | 0.1 | 0.173 ± 0.003 | 3.5 ± 0.3 |
| NEPS1-WT | NADP+ | 1000 | 4a | 0.1 | *0.020 ± 0.005* | |

TABLE 2-continued

Kinetic parameters of NEPS1 dehydrogenase activity.

| Enzyme | Substrate | [Substrate] μM | Co-substrate | [Co-substrate] mM | $K_{cat}$ or V $s^{-1}$ | $K_m$ μM |
|---|---|---|---|---|---|---|
| NEPS1-WT | 1a | 1000 | NADH | 0.1 | no reaction | |
| NEPS1-T154G | 4a | 50-750 | NAD+ | 1 | 0.0804 ± 0.005 | 251 ± 37 |
| NEPS1-T154G | NAD+ | 7.8-1000 | 4a | 0.5 | 0.0599 ± 0.002 | 26 ± 4 |

Activity measured spectrophotometrically by absorbance at 340 nm. Activities are reported as $k_{cat}$ when substrate concentration was varied, and velocity (V, italics) when a single substrate concentration was used. Kinetic Michaelis-Menten parameters are reported as a best fit estimate ± SE. Velocity (italics) is reported as a mean of triplicate measurements ± standard deviation from the mean.

TABLE 3

X-ray data collection and refinement statistics

Data collection

| | |
|---|---|
| Beamline | I03, Diamond Light Source, UK |
| Wavelength (Å) | 0.9763 |
| Detector | Pilatus 6M |
| Resolution range[a] (Å) | 47.16-1.40 (1.42-1.40) |
| Space Group | $P2_1$ |
| Cell parameters (Å/°) | a = 63.9 b = 107.8, c = 69.4, β = 104.3 |
| Total no. of measured intensities[a] | 1205639 (59269) |
| Unique reflections[a] | 175909 (8610) |
| Multiplicity[a] | 6.9 (6.9) |
| Mean I/σ(I)[a] | 11.2 (1.2) |
| Completeness[a] (%) | 98.6 (97.0) |
| $R_{merge}$[a,b] | 0.090 (1.564) |
| $R_{meas}$[a,c] | 0.097 (1.690) |
| $CC_{1/2}$[a,d] | 0.999 (0.561) |
| Wilson B value (Å²) | 14.5 |

Refinement

| | |
|---|---|
| Resolution range[a] (Å) | 47.16-1.40 (1.42-1.40) |
| Reflections: working/free[e] | 167049 (8822) |
| $R_{work}/R_{free}$[a,f] | 0.150/0.168 (0.276/0.283) |
| Ramachandran: favoured/allowed/disallowed[g] (%) | 97.6/2.4/0.0 |
| R.m.s. bond distance deviation (Å) | 0.011 |
| R.m.s. bond angle deviation (°) | 1.56 |
| No. of protein residues (ranges): chains A, B, C, D | 257 (9-265), 257 (9-265), 260 (7-266), 258 (9-266) |
| No. of water molecules/NAD+ molecules/Cl⁻ ions | 1050/4/4 |
| Mean B factors: protein/water/NAD+/Cl⁻/overall (Å²) | 17.9/30.2/14.4/20.9/18.4 |
| PDB accession code | 6F9Q |

[a]Figures in parentheses indicate values for the outer resolution shell.
[b]$R_{merge} = \Sigma_{hkl} \Sigma_i |I_i(hkl) - \langle I(hkl)\rangle|/ \Sigma_{hkl} \Sigma_i I_i(hkl)$.
[c]$R_{meas} = \Sigma_{hkl} [N/(N+1)]^{1/2} \times \Sigma_i |I_i(hkl) - \langle I(hkl)\rangle|/ \Sigma_{hkl} \Sigma_i I_i(hkl)$, where $I_i(hkl)$ is the ith observation of reflection hkl, <I(hkl)> is the weighted average intensity for all observations i of reflection hkl and N is the number of observations of reflection hkl.
[d]$CC_{1/2}$ is the correlation coefficient between intensities taken from random halves of the dataset.
[e]The data set was split into "working" and "free" sets consisting of 95 and 5% of the data, respectively. The free set was not used for refinement.
[f]The R-factors $R_{work}$ and $R_{free}$ are calculated as follows: $R = \Sigma(|F_{obs} - F_{calc}|/\Sigma|F_{obs}|$, where $F_{obs}$ and $F_{calc}$ are the observed and calculated structure factor amplitudes, respectively.
[g]As calculated using MolProbity[4]

TABLE 4

Primers used in mutation investigation into NEPS1 and NEPS3.

| Enzyme | Mutation | Forward Mutation Primer | Reverse Mutation Primer |
|---|---|---|---|
| NEPS1 | V110A | TGGGCTGGACATGATGTTCTCCAATGCGGGGATCATGAGCAAGTC (SEQ ID NO: 15) | ATTGGAGAACATCATGTCCAGCCCA (SEQ ID NO: 39) |
| NEPS1 | N125A | GGAATTCGATAAAGTGATGCGCGTGGCCGCGCGCGGGATGGCTGC (SEQ ID NO: 16) | CACGCGCATCACTTTATCGAATTCC (SEQ ID NO: 40) |
| NEPS1 | T152N | AGGAACGAGACACTATTATCTGCAATACCACCCCGCTATCGTC (SEQ ID NO: 17) | GCAGATAATAGTGCCTCTCGTTCCT (SEQ ID NO: 41) |
| NEPS1 | T153A | AACGAGAGGCACTATTATCTGCACGGCCACCCCGCTATCGTCGAG (SEQ ID NO: 18) | CGTGCAGATAATAGTGCCTCTCGTTCC (SEQ ID NO: 42) |

TABLE 4-continued

Primers used in mutation investigation into NEPS1 and NEPS3.

| Enzyme | Mutation | Forward Mutation Primer | Reverse Mutation Primer |
|---|---|---|---|
| NEPS1 | T154G | CGAGAGGCACTATTATCTGCACGACCGGCCC GCTATCGTCGAGG (SEQ ID NO: 19) | GGTCGTGCAGATAATAGTGC CTCTCG (SEQ ID NO: 43) |
| NEPS1 | P155S | AGGCACTATTATCTGCACGACCACCTCGCTAT CGTCGAGGGGCGGGCA (SEQ ID NO: 20) | GGTGGTCGTGCAGATAATAG TGCCT (SEQ ID NO: 44) |
| NEPS1 | L156S | CACTATTATCTGCACGACCACCCCGTCATCGTC GAGGGGCGGGCA (SEQ ID NO: 21) | CGGGGTGGTCGTGCAGATAA TAGTG (SEQ ID NO: 45) |
| NEPS1 | Y167F | GAGGGGCGGGCAAAGCATGACGGACTTTGC GATGTCGAAGCACG (SEQ ID NO: 22) | GTCCGTCATGCTTTGCCCGCC CCTC (SEQ ID NO: 46) |
| NEPS1 | K171M | AAGCATGACGGACTATGCGATGTCGATGCAC GCAGTGATGGG (SEQ ID NO: 23) | CGACATCGCATAGTCCGTCAT GCT (SEQ ID NO: 47) |
| NEPS1 | S198M | GATTAGGGTTAACTGCGTGACGCCGATGGTG GTGCTCACGCCGCT (SEQ ID NO: 24) | CGGCGTCACGCAGTTAACCC TAATCC (SEQ ID NO: 48) |
| NEPS1 | V199A | TAGGGTTAACTGCGTGACGCCGTCGGCGGTG CTCACGCCGCTCG (SEQ ID NO: 25) | CGACGGCGTCACGCAGTTAA CCCT (SEQ ID NO: 49) |
| NEPS1 | T202A | CTGCGTGACGCCGTCGGTGGTGCTCGCGCCG CTCGCCCAACGGATG SEQ ID NO: 26) | GAGCACCACCGACGGCGTCA CGCAG (SEQ ID NO: 50) |
| NEPS1 | TT152NA | AGGAACGAGAGGCACTATTATCTGCAATGCC ACCCCGCTATCGTC (SEQ ID NO: 27) | GCAGATAATAGTGCCTCTCGT TCCT (SEQ ID NO: 51) |
| NEPS1 | TTT15 2 NAG | AGGAACGAGAGGCACTATTATCTGCAACGCC GGCCCGCTATCGTC (SEQ ID NO: 28) | GCAGATAATAGTGCCTCTCGT TCCT (SEQ ID NO: 52) |
| NEPS1 | TTTP15 2 NAGS | AGGAACGAGAGGCACTATTATCTGCAACGCC GGTAGCCTATCGTCGAGG (SEQ ID NO: 29) | GCAGATAATAGTGCCTCTCGT TCCT (SEQ ID NO: 53) |
| NEPS1 | TTTPL152 NAGSS | AGGAACGAGAGGCACTATTATCTGCAACGCC GGTAGCTCATCGTCGAGG (SEQ ID NO: 30) | GCAGATAATAGTGCCTCTCGT TCCT (SEQ ID NO: 54) |
| NEPS3 | N150T | GGGAAGGGGAGGGTCCATCATATGCACCGCC GGCTCGTCGGCGGT (SEQ ID NO: 31) | GCATATGATGGACCCTCCCCT TCC (SEQ ID NO: 55) |
| NEPS3 | A151T | AAGGGGAGGGTCCATCATATGCAACACCGGC TCGTCGGCGGTGAG (SEQ ID NO: 32) | GTTGCATATGATGGACCCTCC CCTT (SEQ ID NO: 56) |
| NEPS3 | G152T | GGGAGGGTCCATCATATGCAACGCCACCTCG TCGGCGGTGAGG (SEQ ID NO: 33) | GGCGTTGCATATGATGGACC CTCC (SEQ ID NO: 57) |
| NEPS3 | S153P | AGGGTCCATCATATGCAACGCCGGCCCGTCG GCGGTGAGGGGCGCGCA (SEQ ID NO: 34) | GCCGGCGTTGCATATGATGG ACCCT (SEQ ID NO: 58) |
| NEPS3 | S154L | GTCCATCATATGCAACGCCGGCTCGCTGGCG GTGAGGGGCGCGCA (SEQ ID NO: 35) | CGAGCCGGCGTTGCATATGA TGGAC (SEQ ID NO: 59) |
| NEPS3 | Y165F | GAGGGGCGCGCATGGCGTGACGGACTTCGTG ATGTCGAAGCATGC (SEQ ID NO: 36) | GTCCGTCACGCCATGCGCGC CCCTC (SEQ ID NO: 60) |
| NEPS3 | K169M | TGGCGTGACGGACTACGTGATGTCGAUGCAT GCGGTGATAGGGCTGGTG (SEQ ID NO: 37) | CGACATCACGTAGTCCGTCAC GCCA (SEQ ID NO: 61) |
| NEPS3 | M196S | TATTAGGGTTAACAGCGTGTCGCCGAGTGCC GTGGCGACGCCGCT (SEQ ID NO: 38) | CGGCGACACGCTGTTAACCC TAATACTG (SEQ ID NO: 62) |

The invention claimed is:

1. A method for producing a monoterpenoid compound, comprising:
   (1) providing a genetically modified cell comprising one or more nucleic acids heterologous to the cell,
      wherein the one or more nucleic acids encode one or more of:
         an enzyme that comprises an amino acid sequence having at least 95% sequence identity to SEQ ID NO: 1 [NEPS1];
         an enzyme that comprises an amino acid sequence having at least 95% sequence identity to SEQ ID NO: 2 [NEPS2]; and/or
         an enzyme that comprises an amino acid sequence having at least 95% sequence identity to SEQ ID NO: 3 [NEPS3];
      wherein the one or more of the enzymes are expressed in the genetically modified cell; and
   (2) providing a monoterpenoid precursor to the genetically modified cell,
      wherein the one or more of the enzymes act on the monoterpenoid precursor to produce the monoterpenoid compound.

2. The method of claim 1, wherein the one or more of the enzymes comprises an amino acid sequence comprising SEQ ID NO: 1 and is encoded by a nucleotide sequence comprising SEQ ID NO: 4, and/or the one or more of the enzymes comprises an amino acid sequence comprising SEQ ID NO: 2 and is encoded by a nucleotide sequence comprising SEQ ID NO: 5, and/or the one or more of the enzymes comprises an amino acid sequence comprising SEQ ID NO: 3 and is encoded by a nucleotide sequence comprising SEQ ID NO: 6.

3. The method of claim 1, wherein the monoterpenoid compound comprises an iridoid.

4. The method of claim 1, wherein the monoterpenoid precursor comprises an acyclic monoterpenoid.

5. The method of claim 1, wherein the one or more of the enzymes further comprise an iridoid synthase (ISY), wherein the ISY comprises an amino acid sequence of having at least 95% sequence identity to SEQ ID NO: 7 [AmISY], an amino acid sequence having at least 95% sequence identity to SEQ ID NO: 8 [NmISY2], or an amino acid sequence having at least 95% sequence identity to SEQ ID NO: 9 [CrISY].

6. The method of claim 5, wherein the ISY is encoded by a nucleotide sequence comprising SEQ ID NO: 10, SEQ ID NO: 11, or SEQ ID NO: 12.

7. The method of claim 6, wherein the monoterpenoid precursor comprises 8-oxogeranial.

8. The method of claim 1, wherein the monoterpenoid precursor or compound comprises nepetalactol.

9. The method of claim 8, wherein the nepetalactol comprises cis-trans nepetalactol, and wherein the one or more of the enzymes comprise an enzyme which comprises an amino acid sequence having at least 95% sequence identity to SEQ ID NO: 1 and/or an enzyme which comprises an amino acid sequence having at least 95% sequence identity to SEQ ID NO: 2.

10. The method of claim 8, wherein the nepetalactol comprises cis-cis nepetalactol, wherein the one or more of the enzymes comprise an enzyme which comprises an amino acid sequence having at least 95% sequence identity to SEQ ID NO: 1 and/or an enzyme which comprises an amino acid sequence having at least 95% sequence identity to SEQ ID NO: 3.

11. The method of claim 1, wherein the monoterpenoid compound comprises nepetalactone.

12. The method of claim 11, wherein the nepetalactone comprises cis-trans nepetalactone, and wherein the one or more of the enzymes comprise an enzyme which comprises an amino acid sequence having at least 95% sequence identity to SEQ ID NO: 1 and/or an enzyme which comprises an amino acid sequence having at least 95% sequence identity to SEQ ID NO: 2.

13. The method of claim 11, wherein the nepetalactone comprises cis-cis nepetalactone, wherein the one or more of the enzymes comprise an enzyme which comprises an amino acid sequence having at least 95% sequence identity to SEQ ID NO: 1 and/or an enzyme which comprises an amino acid sequence having at least 95% sequence identity to SEQ ID NO: 3.

14. The method of claim 13, wherein the nepetalactone comprises both cis-trans nepetalactone and cis-cis nepetalactone.

15. The method of claim 1, wherein the monoterpenoid compound comprises a cyclopentapyran.

16. The method of claim 1 wherein the monoterpenoid compound comprises a oxadecalin.

17. The method of claim 1, wherein the genetically modified cell is a plant cell, yeast, or bacteria.

18. The method of claim 1, wherein the genetically modified cell is a plant cell.

19. The method of claim 1, wherein the method is performed in planta (in the plant).

20. A method for producing a biologically active compound in a genetically modified cell, comprising the steps of:
   (1) preforming the steps as defined in claim 1; and
   (2) converting the monoterpenoid compound into a biologically active compound.

21. The method of claim 4, wherein the acyclic monoterpenoid comprises 8-oxocitronellyl enol and/or 8-oxocitronellal and/or derivatives thereof.

22. The method of claim 18, wherein the method is performed in an isolated plant cell.

23. The method of claim 20, wherein the biologically active compound is selected from: an insect repellent; an insect attractant; a feline attractant; and a monoterpene indole alkaloid.

24. The method of claim 23, wherein the monoterpene indole alkaloid is selected from the group consisting of vinblastine, vincristine, camptothecin, quinine and yohimbine.

25. A method for producing a monoterpenoid compound in vitro, comprising:
   (1) providing a monoterpenoid precursor;
   (2) providing one or more isolated enzymes; and
   (3) contacting the provided monoterpenoid precursor with the one or more isolated enzymes under catalytic conditions to produce a monoterpenoid compound;
   wherein the one or more isolated enzymes comprise an enzyme that comprises an amino acid sequence having at least 95% sequence identity to SEQ ID NO: 1 [NEPS1]; and/or an enzyme that comprises an amino acid sequence having at least 95% sequence identity to SEQ ID NO: 2 [NEPS2]; and/or an enzyme that comprises an amino acid sequence having at least 95% sequence identity to SEQ ID NO: 3 [NEPS3].

26. The method of claim 25, wherein the one or more isolated enzymes further comprise an iridoid synthase (ISY), wherein the ISY comprises an amino acid sequence having at least 95% sequence identity to SEQ ID NO: 7 [AmISY], an amino acid sequence having at least 95% sequence identity to SEQ ID NO: 8 [NmISY2], or an amino acid sequence having at least 95% sequence identity to SEQ ID NO: 9 [CrISY].

27. The method of claim 26, wherein the ISY is encoded by a nucleotide sequence comprising SEQ ID NO: 10, SEQ ID NO: 11, or SEQ ID NO: 12.

28. A method for producing a biologically active compound in vitro, comprising the steps of:
   (1) preforming the steps as defined in claims 25; and
   (2) converting the monoterpenoid compound into a biologically active compound.

* * * * *

SEQUENCE LISTING

<160> NUMBER OF SEQ ID NOS: 74

<210> SEQ ID NO 1
<211> LENGTH: 271
<212> TYPE: PRT
<213> ORGANISM: Nepeta mussinii -continued

```
<400> SEQUENCE: 1

Met Ala Ser Thr Ala Asn Pro Met Gln Val Met Lys Lys Leu Glu
1               5                  10                  15

Gly Lys Val Val Ile Val Thr Gly Gly Ala Ser Gly Ile Gly Gln Thr
            20                  25                  30

Ala Ala Arg Val Phe Ala Gln His Gly Ala Arg Ala Val Val Ile Ala
        35                  40                  45

Asp Ile Gln Ser Glu Val Gly Lys Ser Val Ala Lys Ser Ile Gly Asp
    50                  55                  60

Pro Cys Cys Tyr Val Gln Cys Asp Val Ser Asp Glu Glu Val Lys
65                  70                  75                  80

Ser Met Ile Glu Trp Thr Ala Ser Ala Tyr Gly Gly Leu Asp Met Met
                85                  90                  95

Phe Ser Asn Val Gly Ile Met Ser Lys Ser Ala Gln Thr Val Met Asp
            100                 105                 110

Leu Asp Leu Leu Glu Phe Asp Lys Val Met Arg Val Asn Ala Arg Gly
        115                 120                 125

Met Ala Ala Cys Leu Lys His Ala Ala Arg Lys Met Val Glu Leu Gly
    130                 135                 140

Thr Arg Gly Thr Ile Ile Cys Thr Thr Thr Pro Leu Ser Ser Arg Gly
145                 150                 155                 160

Gly Gln Ser Met Thr Asp Tyr Ala Met Ser Lys His Ala Val Met Gly
                165                 170                 175

Leu Val Arg Ser Ala Ser Ile Gln Leu Gly Ala His Gly Ile Arg Val
            180                 185                 190

Asn Cys Val Thr Pro Ser Val Val Leu Thr Pro Leu Ala Gln Arg Met
        195                 200                 205

Gly Leu Ala Thr Pro Asp Asp Phe His Thr His Phe Gly Asn Phe Thr
    210                 215                 220

Ser Leu Lys Gly Val Tyr Leu Thr Pro Glu Gln Val Ala Glu Ala Val
225                 230                 235                 240

Val Tyr Leu Ala Ser Asp Ala Ala Phe Ile Thr Gly His Asp Leu
                245                 250                 255

Val Leu Asp Gly Gly Leu Leu Cys Leu Pro Phe Phe Ala Pro Ser
            260                 265                 270

<210> SEQ ID NO 2
<211> LENGTH: 268
<212> TYPE: PRT
<213> ORGANISM: Nepeta mussinii

<400> SEQUENCE: 2

Met Gly Asn Lys Lys Thr Leu Glu Gly Lys Val Ala Ile Val Thr Gly
1               5                  10                  15

Gly Ala Ser Gly Ile Gly Glu Thr Ala Ala Arg Val Phe Ala Asn Leu
            20                  25                  30

Gly Ala Arg Ala Val Val Ile Ala Asp Ile Gln Ser Glu Leu Gly Arg
        35                  40                  45

Glu Val Ala Glu Ser Ile Gly Ala Lys Arg Cys Ser Tyr Val Gln Cys
    50                  55                  60

Asp Ile Gly Asp Glu Glu Gln Val Lys Ser Met Val Glu Trp Thr Ala
65                  70                  75                  80

Thr Thr Tyr Gly Ala Leu Asp Val Met Phe Cys Asn Ala Gly Ile Met
                85                  90                  95
```

```
Ser Lys Ala Glu Ser Ala Gln Thr Val Leu Glu Leu Asp Met Ser Lys
                100                 105                 110

Phe Asp Glu Val Met Arg Val Asn Thr Arg Gly Thr Ser Ala Cys Val
            115                 120                 125

Lys Gln Ala Ala Arg Lys Met Val Glu Leu Gly Thr Lys Gly Gly Ala
        130                 135                 140

Ile Val Cys Thr Ser Ser Pro Leu Ala Ser Arg Gly Gly Tyr Ile Asp
145                 150                 155                 160

Thr Asp Tyr Val Met Ser Lys His Ala Val Met Gly Leu Val Arg Ser
                165                 170                 175

Ala Ser Met Gln Leu Gly Ala His Gly Ile Arg Val Asn Ser Val Ser
            180                 185                 190

Pro Met Ala Val Leu Thr Pro Leu Thr Arg Arg Met Gly Leu Ala Thr
        195                 200                 205

Pro Ala Asp Val Glu Asn Ala Phe Gly Arg Phe Thr Ser Leu Lys Gly
            210                 215                 220

Val Ala Leu Thr Ala Glu His Val Ala Glu Ala Ala Phe Leu Ala
225                 230                 235                 240

Ser Asp Glu Ala Ala Phe Ile Thr Gly His Asp Leu Met Val Asp Gly
                245                 250                 255

Gly Leu Leu Cys Leu Pro Phe Phe Ala Pro Thr Ser
            260                 265

<210> SEQ ID NO 3
<211> LENGTH: 270
<212> TYPE: PRT
<213> ORGANISM: Nepeta mussinii

<400> SEQUENCE: 3

Met Ala Asn Asn Ser Val Met Met Lys Lys Lys Leu Glu Gly Lys Val
1               5                   10                  15

Ala Ile Val Thr Gly Gly Ala Ser Gly Ile Gly Glu Ala Thr Ala Arg
            20                  25                  30

Leu Phe Val Lys Tyr Gly Ala Arg Ala Val Val Ile Ala Asp Ile Gln
        35                  40                  45

Ser Glu Leu Gly Arg Ser Val Ala Glu Ser Ile Gly Lys Glu Arg Cys
    50                  55                  60

Ser Phe Val Gln Cys Asp Val Ala Asp Glu Glu Gln Val Lys Ser Met
65                  70                  75                  80

Ile Glu Trp Thr Ala Thr Thr Tyr Gly Gly Leu Asp Val Met Phe Ser
                85                  90                  95

Asn Ala Gly Val Leu Asn Ser Ala Ala Gln Thr Val Lys Asp Leu Asp
            100                 105                 110

Leu Pro Leu Phe Asp Lys Val Met Arg Val Asn Thr Arg Gly Ala Ala
        115                 120                 125

Val Cys Val Lys Gln Ala Ala Arg Lys Met Val Glu Leu Gly Arg Gly
    130                 135                 140

Gly Ser Ile Ile Cys Asn Ala Gly Ser Ser Ala Val Arg Gly Ala His
145                 150                 155                 160

Gly Val Thr Asp Tyr Val Met Ser Lys His Ala Val Ile Gly Leu Val
                165                 170                 175

Arg Ser Ala Ser Met Gln Leu Gly Ala His Ser Ile Arg Val Asn Ser
            180                 185                 190
```

```
Val Ser Pro Met Ala Val Ala Thr Pro Leu Thr Arg Asn Gln Gly Ile
    195                 200                 205

Ser Thr Pro Asp Asp Val Gln Lys Phe Leu Met Pro Phe Ile Ser Leu
    210                 215                 220

Lys Gly Val Pro Pro Thr Ala Glu Gln Val Ala Glu Ala Ala Ala Phe
225                 230                 235                 240

Leu Gly Ser Asp Glu Ala Ala Phe Val Thr Gly His Asp Leu Pro Val
                245                 250                 255

Asp Gly Gly Val Leu Cys Met Pro Phe Leu Leu Gly Ser Ala
                260                 265                 270

<210> SEQ ID NO 4
<211> LENGTH: 816
<212> TYPE: DNA
<213> ORGANISM: Nepeta mussinii

<400> SEQUENCE: 4
```

| | | | | | |
|---|---|---|---|---|---|
| atggcaagca | ctgcaaatcc | gatgcaggtg | atgaagaaga | agctggaagg | caaagtggtg | 60 |
| atagtaacag | gcggggcgag | cggcatcggg | cagacggcag | cgcgtgtctt | tgcacaacat | 120 |
| ggcgcgcgtg | cggtggtcat | cgctgacatc | caatctgaag | ttgggaagtc | cgtcgcgaag | 180 |
| tccatcggag | acccgtgctg | ctacgtccag | tgcgacgtct | cggacaggga | agaggtaaag | 240 |
| tcgatgatag | aatggacggc | cagcgcgtac | ggtgggctgg | acatgatgtt | ctccaatgtg | 300 |
| gggatcatga | gcaagtctgc | tcaaaccgta | atggacctcg | acctcttgga | attcgataaa | 360 |
| gtgatgcgcg | tgaacgcgcg | cgggatggct | gcgtgcttga | agcacgcagc | gcgtaagatg | 420 |
| gtggagctag | aacgagagg | cactattatc | tgcacgacca | ccccgctatc | gtcgaggggc | 480 |
| gggcaaagca | tgacggacta | tgcgatgtcg | aagcacgcag | tgatggggct | ggtccggtcg | 540 |
| gccagcatac | agctgggggc | ccacgggatt | agggttaact | gcgtgacgcc | gtcggtggtg | 600 |
| ctcacgccgc | tcgcccaacg | gatggggctt | gccacgcccg | atgatttcca | tactcatttt | 660 |
| ggcaacttca | ccagcctcaa | agggggtctac | ctcacacccg | aacaagttgc | cgaagccgtc | 720 |
| gtctatctcg | cttccgacga | cgccgccttc | atcactggac | atgatttggt | cctcgatggc | 780 |
| ggactgcttt | gtttaccatt | ctttgctcct | tcataa | | | 816 |

```
<210> SEQ ID NO 5
<211> LENGTH: 807
<212> TYPE: DNA
<213> ORGANISM: Nepeta mussinii

<400> SEQUENCE: 5
```

| | | | | | |
|---|---|---|---|---|---|
| atgggcaaca | agaagacgct | agaaggcaaa | gtagccatcg | taaccggcgg | cgccagcggc | 60 |
| atcggcgaga | ccgccgcccg | cgtgttcgcc | aacctcggcg | cgcgtgcggt | ggtgatcgcc | 120 |
| gatattcagt | cggaattggg | gcgggaagtg | gcggaatcca | tcggggcgaa | gcggtgcagc | 180 |
| tacgtgcagt | gcgacatcgg | cgacgaggag | caggttaagt | cgatggtgga | atggacggcc | 240 |
| accacctacg | gcgcgctcga | cgtgatgttc | tgcaacgccg | gcatcatgag | caaagctgag | 300 |
| tccgcgcaga | cggtgctgga | gctcgacatg | tcgaagttcg | acgaggtcat | gcgtgtgaac | 360 |
| acgcgcggga | cgtcggcgtg | cgtgaagcag | gcggcgcgta | agatggtgga | gctgggaacg | 420 |
| aagggaggcg | ccatcgtatg | cacgagcagc | ccgctggcct | cgaggggcgg | atacattgat | 480 |
| acggactacg | tgatgtcgaa | gcacgcggtg | atggggctgg | tgcggtcggc | cagcatgcag | 540 |
| ctcggggccc | acgggattag | ggttaacagc | gtgtcgccga | tggcggtgct | aacgccgctc | 600 |

| | | |
|---|---|---|
| acccgaagga tgggggcttgc gacgcccgct gacgtcgaga atgccttcgg gcggttcact | | 660 |
| agcttgaaag gggtggcgct cacggcggag cacgtcgcgg aggccgccgc ctttctcgct | | 720 |
| tcagatgagg cggctttcat caccggccat gatctcatgg tggatggcgg actgctttgt | | 780 |
| ttaccattct ttgcaccaac atcataa | | 807 |

<210> SEQ ID NO 6
<211> LENGTH: 813
<212> TYPE: DNA
<213> ORGANISM: Nepeta mussinii

<400> SEQUENCE: 6

| | | |
|---|---|---|
| atggctaaca attcagtgat gatgaagaag aagctcgaag gcaaagtagc cattgtaacc | | 60 |
| ggcggcgcca gcggtatagg cgaggccacc gcccgcttgt tcgtgaagta cggggcgcgt | | 120 |
| gcggtggtga tcgcggatat tcagtcggaa ttagggcggt ccgtggcgga atcaatcggg | | 180 |
| aaggagcggt gcagcttcgt gcagtgcgac gtcgccgacg aggagcaggt gaagtccatg | | 240 |
| atagagtgga cggccaccac gtacggcggc ctcgacgtaa tgttcagcaa cgccggcgtc | | 300 |
| ttgaacagcg ccgcgcagac cgtgaaggac ttggacctgc cgctgttcga caaggtgatg | | 360 |
| cgtgtgaaca cgcgcggcgc ggccgtgtgc gtgaagcagg cggcgcgtaa gatggtggag | | 420 |
| ctgggaaggg gagggtccat catatgcaac gccggctcgt cggcggtgag gggcgcgcat | | 480 |
| ggcgtgacgg actacgtgat gtcgaagcat gcggtgatag ggctggtgcg gtcggccagc | | 540 |
| atgcagcttg gggcccacag tattagggtt aacagcgtgt cgccgatggc cgtggcgacg | | 600 |
| ccgctcaccc ggaaccaagg catttcgacg ccggatgatg tacagaaatt tttgatgcct | | 660 |
| ttcatcagcc tgaaaggggt gccgcccacg gcggagcaag tggcggaagc ggcggcgttc | | 720 |
| ctgggttccg atgaggcggc gttcgtgacg gggcatgatc tgccggtgga tggcggcgtg | | 780 |
| ctctgtatgc catttctcct cggttcagca taa | | 813 |

<210> SEQ ID NO 7
<211> LENGTH: 387
<212> TYPE: PRT
<213> ORGANISM: Antirrhinum majus

<400> SEQUENCE: 7

Met Ser Trp Trp Tyr Arg Arg Ser Ile Gly Glu Thr Glu Gln Lys Arg
1               5                   10                  15

Ile Glu Ile Asn Gly Val Ser Pro Thr Tyr Gln Ser Val Ala Leu Ile
            20                  25                  30

Val Gly Val Thr Gly Ile Ala Gly Ser Gly Leu Ala Glu Thr Leu Ser
        35                  40                  45

Phe Ser Asp Thr Pro Gly Gly Pro Trp Lys Val Tyr Gly Val Ala Arg
    50                  55                  60

Arg Pro Cys Pro Lys Trp Leu Ala Lys Leu Asn Val Asn Tyr Val Gln
65                  70                  75                  80

Cys Asp Ile Ala Asn Thr Asp Glu Thr Tyr Ser Lys Val Ala Pro Leu
                85                  90                  95

Thr Asp Ile Thr His Ile Phe Tyr Val Ser Trp Thr Gly Ser Glu Asp
            100                 105                 110

Val Ala Leu Asn Thr Leu Met Phe Lys Asn Ile Leu Asp Ser Val Ile
        115                 120                 125

Pro Asn Ala Pro Asn Leu Lys His Val Ser Leu Gln Thr Gly Ile Lys
    130                 135                 140

Tyr Tyr Trp Gly Asn Met Ala Glu Met Asp Ser Thr Asn Gln Pro His
145                 150                 155                 160

Glu Cys Pro Phe Tyr Glu Asn Met Pro Arg Leu Lys Gln Asp Asn Phe
                165                 170                 175

Tyr Tyr Asn Leu Glu Asp Leu Val Tyr Asp Ser Ala Val Arg Lys Asn
            180                 185                 190

Gly Leu Ser Trp Ser Ile His Arg Pro Ala Leu Ile Phe Gly Phe Ser
        195                 200                 205

Pro Cys Ser Met Met Asn Thr Val Ser Thr Leu Cys Val Tyr Ala Ala
    210                 215                 220

Ile Cys Lys His Glu Asn Lys Pro Leu Val Tyr Thr Gly Thr Glu Thr
225                 230                 235                 240

Ser Trp Thr Cys Leu Trp Asp Ala Val Asp Ser Asp Leu Leu Ala Glu
                245                 250                 255

His Phe Leu Trp Ala Ala Thr Val Pro Asn Ala Lys Asn Gln Ala Phe
            260                 265                 270

Asn Ile Asn Asn Gly Asp Val Phe Lys Trp Lys His Met Trp Lys Val
        275                 280                 285

Leu Ala Lys Glu Phe Asp Ile Glu Ala Ile Gly Tyr Glu Gly Lys Glu
    290                 295                 300

Pro Val Leu Leu Glu Asp Leu Met Lys Asp Lys Asp Ser Val Trp Asp
305                 310                 315                 320

Glu Ile Val Lys Lys His Asp Leu Val Pro Thr Lys Leu Arg Asp Ile
                325                 330                 335

Ala Ala Phe Trp Leu Ala Asp Val Val Phe Arg Asn Lys Glu Thr Leu
            340                 345                 350

Cys Ser Met Asn Lys Asn Lys Glu Phe Gly Phe Met Gly Phe Arg Asp
        355                 360                 365

Thr Thr Lys Ser Phe Val Ser Ser Ile Asn Lys Met Arg Asp Phe Lys
    370                 375                 380

Phe Ile Pro
385

<210> SEQ ID NO 8
<211> LENGTH: 396
<212> TYPE: PRT
<213> ORGANISM: Nepeta mussinii

<400> SEQUENCE: 8

Met Ser Leu Ser Trp Trp Arg Ala Gly Ala Lys Lys Arg Met Asp
1               5                   10                  15

Asp Asp Glu Ser Leu Leu Val Lys Gln Gln Gln Gln Cys Val Ala
                20                  25                  30

Leu Ile Val Gly Val Thr Gly Leu Val Gly Asn Ser Leu Ala Glu Met
            35                  40                  45

Leu Pro Leu Pro Asp Thr Pro Gly Gly Pro Trp Lys Val Tyr Gly Val
    50                  55                  60

Ala Arg Arg Ala Arg Pro Ser Trp Asn Glu Asp Gln Pro Met Thr Tyr
65                  70                  75                  80

Ile Ser Cys Asp Val Ser Asn Thr Gly Glu Val Glu Ala Lys Leu Ser
                85                  90                  95

Pro Leu Ser Asp Val Thr His Ile Phe Tyr Ala Thr Trp Thr Ser Arg
            100                 105                 110

```
Ser Thr Glu Glu Glu Asn Cys Glu Ala Asn Gly Lys Met Leu Lys Asn
            115                 120                 125

Val Leu Asp Ala Met Ile Pro Asn Cys Pro Asn Leu Lys His Ile Cys
        130                 135                 140

Leu Gln Thr Gly Arg Phe His Tyr Val Ala Ser Val Val Asp Trp Lys
145                 150                 155                 160

Ile Asn Gly Ser His Asp Thr Pro Leu Thr Glu Asp Leu Pro Arg Leu
                165                 170                 175

Lys Thr Asn Asn Phe Tyr Tyr Thr Gln Glu Asp Ile Leu Leu Glu Glu
            180                 185                 190

Val Lys Arg Lys Glu Gly Leu Thr Trp Ser Val His Arg Pro Gly Thr
        195                 200                 205

Ile Phe Gly Phe Ser Pro Tyr Ser Met Met Asn Leu Val Gly Thr Leu
210                 215                 220

Cys Val Tyr Ala Ala Ile Cys Lys Gln Glu Gly Ala Val Leu Arg Phe
225                 230                 235                 240

Pro Gly Cys Lys Gly Ala Trp Asp Gly His Ser Asp Cys Ala Asp Ala
                245                 250                 255

Asp Leu Ile Ala Glu Gln Gln Ile Trp Ala Ala Leu Asp Pro His Ala
            260                 265                 270

Lys Asn Gln Ala Phe Asn Val Ser Asn Gly Asp Leu Phe Lys Trp Lys
        275                 280                 285

His Leu Trp Lys Val Leu Ala Asp Gln Phe Gly Val Glu Cys Gly Asp
            290                 295                 300

Tyr Glu Glu Gly Gln Gln Leu Arg Leu Gln Asp Val Met Lys Asp Lys
305                 310                 315                 320

Gly Pro Val Trp Asp Lys Ile Val Ala Glu Asn Gly Leu Ser Asn Thr
                325                 330                 335

Lys Leu Glu Asp Val Gly Lys Trp Trp Phe Ser Asp Thr Ile Leu Trp
            340                 345                 350

Asn Glu Cys Arg Leu Asp Ser Met Asn Lys Ser Lys Glu His Gly Phe
        355                 360                 365

Leu Gly Phe Arg Asn Ser Lys Asn Cys Phe Leu Tyr Trp Ile His Lys
    370                 375                 380

Val Lys Ala Tyr Asn Leu Val Pro Ser Thr Tyr Thr
385                 390                 395

<210> SEQ ID NO 9
<211> LENGTH: 388
<212> TYPE: PRT
<213> ORGANISM: Catharanthus roseus

<400> SEQUENCE: 9

Met Ser Trp Trp Trp Lys Arg Ser Ile Gly Ala Gly Lys Asn Leu Pro
1               5                   10                  15

Asn Gln Asn Lys Glu Asn Gly Val Cys Lys Ser Tyr Lys Ser Val Ala
            20                  25                  30

Leu Val Val Gly Val Thr Gly Ile Val Gly Ser Ser Leu Ala Glu Val
        35                  40                  45

Leu Lys Leu Pro Asp Thr Pro Gly Gly Pro Trp Lys Val Tyr Gly Val
    50                  55                  60

Ala Arg Arg Pro Cys Pro Val Trp Leu Ala Lys Lys Pro Val Glu Tyr
65                  70                  75                  80
```

```
Ile Gln Cys Asp Val Ser Asp Asn Gln Glu Thr Ile Ser Lys Leu Ser
                85                  90                  95
Pro Leu Lys Asp Ile Thr His Ile Phe Tyr Val Ser Trp Ile Gly Ser
            100                 105                 110
Glu Asp Cys Gln Thr Asn Ala Thr Met Phe Lys Asn Ile Leu Asn Ser
        115                 120                 125
Val Ile Pro Asn Ala Ser Asn Leu Gln His Val Cys Leu Gln Thr Gly
    130                 135                 140
Ile Lys His Tyr Phe Gly Ile Phe Glu Glu Gly Ser Lys Val Val Pro
145                 150                 155                 160
His Asp Ser Pro Phe Thr Glu Asp Leu Pro Arg Leu Asn Val Pro Asn
                165                 170                 175
Phe Tyr His Asp Leu Glu Asp Ile Leu Tyr Glu Glu Thr Gly Lys Asn
            180                 185                 190
Asn Leu Thr Trp Ser Val His Arg Pro Ala Leu Val Phe Gly Phe Ser
        195                 200                 205
Pro Cys Ser Met Met Asn Ile Val Ser Thr Leu Cys Val Tyr Ala Thr
    210                 215                 220
Ile Cys Lys His Glu Asn Lys Ala Leu Val Tyr Pro Gly Ser Lys Asn
225                 230                 235                 240
Ser Trp Asn Cys Tyr Ala Asp Ala Val Asp Ala Asp Leu Val Ala Glu
                245                 250                 255
His Glu Ile Trp Ala Ala Val Asp Pro Lys Ala Lys Asn Gln Val Leu
            260                 265                 270
Asn Cys Asn Asn Gly Asp Val Phe Lys Trp Lys His Ile Trp Lys Lys
        275                 280                 285
Leu Ala Glu Glu Phe Gly Ile Glu Met Val Gly Tyr Val Gly Gly Lys
    290                 295                 300
Glu Gln Val Ser Leu Ala Glu Leu Met Lys Asp Lys Asp Gln Val Trp
305                 310                 315                 320
Asp Glu Ile Val Lys Lys Asn Asn Leu Val Pro Thr Lys Leu Lys Glu
                325                 330                 335
Ile Ala Ala Phe Trp Phe Ala Asp Ile Ala Phe Cys Ser Glu Asn Leu
            340                 345                 350
Ile Ser Ser Met Asn Lys Ser Lys Glu Leu Gly Phe Leu Gly Phe Arg
        355                 360                 365
Asn Ser Met Lys Ser Phe Val Ser Cys Ile Asp Lys Met Arg Asp Tyr
    370                 375                 380
Arg Phe Ile Pro
385

<210> SEQ ID NO 10
<211> LENGTH: 1164
<212> TYPE: DNA
<213> ORGANISM: Antirrhinum majus

<400> SEQUENCE: 10
atgagctggt ggtatagaag atccattggt gaaactgagc agaaaagaat cgagatcaat    60
ggtgtctccc caacttacca aagcgttgcc ctaatagtcg gcgtcaccgg cattgccggc   120
agcggcttag ccgaaactct ctcgttctcc gacacgcccg gcggcccgtg aaagtctat    180 ggcgtggccc ggcgcccgtg ccccaaatgg ctagccaaac tcaacgtcaa ctacgtgcaa   240
tgcgacattg caaacactga tgaaacatat tccaaagtgg ccccactcac cgacattacc   300
```

```
cacattttct acgtgtcatg daccggatcc gaggatgttg cactaaacac cctcatgttc    360
aaaaacatcc tcgattcggt tatcccaaat gcaccaaatc tcaaacatgt ttcgcttcaa    420
acggggatta atatattg gggcaacatg gctgagatgg atagtactaa tcaaccccat     480
gaatgtccct tttatgaaaa catgcctaga ttgaaacaag ataattttta ttacaatctt    540
gaggatttag tctacgattc ggctgttaga aagaacggtt tatcgtggtc gattcatcgt    600
ccggcactta ttttcgggtt ttcaccttgt agtatgatga acactgtcag cacgctttgt    660
gtatacgccg ccatttgcaa gcacgagaat aagccgttgg tgtataccgg aactgaaacg    720
tcttggactt gtctctggga cgcggttgac tctgatttgt tggcggaaca tttcttgtgg    780
gcggcgaccg ttcctaatgc gaagaatcag gcgttcaata tcaacaatgg tgatgttttt    840
aagtggaaac atatgtggaa agtcctcgca aaggagttcg acattgaagc gattggatac    900
gaaggaaaag agccagtttt gttggaagat ttgatgaagg acaaggattc agtgtgggat    960
gagattgtga agaaacatga tttggtgccg acgaaactga gagacattgc agcgttttgg   1020
ttggcggatg tggtgtttag aaacaaagag acgttgtgca gtatgaacaa gaacaaggag   1080
tttgggttca tggggtttag ggatactact aagtcttttg tgtcttcaat taacaaaatg   1140
agagatttca agtttattcc ttaa                                          1164

<210> SEQ ID NO 11
<211> LENGTH: 1191
<212> TYPE: DNA
<213> ORGANISM: nepeta mussinii

<400> SEQUENCE: 11
atgagcttga gctggtggag ggctggtgct gcgaagaaaa gaatggatga tgatgagtcg     60
ttacttgtaa agcagcagca gcagcaatgc gtagctctga tcgtgggggt gaccggactg    120
gtgggcaaca gcctagcgga gatgctgccg ctgccggaca ccccggggggg accatggaag   180
gtgtacgggg tggcgcggcg ggcccgtccc tcgtggaacg aggaccaacc catgacgtac    240
atctcatgcg acgtgagcaa caccggggag gtggaggcga agctgtcccc tctgagcgac    300
gtaacgcaca tcttctacgc gacgtggacg agccgatcga cggaggagga gaactgcgag   360
gccaacggga agatgctgaa gaatgtgttg gacgcaatga tcccccaactg ccccaacctg   420
aagcacatct gcctgcagac cggacggttc cactacgtcg cctcagttgt ggactggaag   480
atcaacggca gccacgacac cccgttgacg gaggatttac ctcgactgaa gacgaacaac   540
ttctactaca cgcaagagga cattctgttg gaggaggtta gaggaaggga ggggctgaca   600
tggtccgtgc atcgcccggg gactatattc ggcttctcac cctatagcat gatgaatctg   660
gtggggacgc tgtgcgtgta tgcagctatc tgtaagcagg agggtgcagt tttgaggttt   720
cctggttgta agggtgcgtg ggatgggcac tcggactgcg cggatgccga cttgattgcg   780
gagcagcaaa tatgggctgc cctcgatccg catgccaaga accaagcatt caacgtcagc   840
aatgggacc tttcaaatg gaagcactta tggaaggtat tggccgacca attcggcgtc    900
gagtgcgggg actacgagga agggcagcaa ctgaggctgc aggatgtgat gaaggacaaa    960
ggtccggtgt gggacaaaat cgttgcggag aatgggctgt ccaataccaa attggaggat   1020
gtcgggaaat ggtggtttag tgatactatc ttgtggaatg agtgtaggtt ggatagtatg   1080
aataagagca aggagcatgg cttcttggc tttaggaatt ccaagaattg ctttctttat    1140
tggattcata aggtcaaggc ttacaacctt gttccttcta cctataccta a            1191
```

```
<210> SEQ ID NO 12
<211> LENGTH: 1167
<212> TYPE: DNA
<213> ORGANISM: Catharanthus roseus

<400> SEQUENCE: 12
atgagttggt ggtggaagag gtccattggt gctggaaaga acttaccaaa ccagaacaaa      60
gaaaatggag tttgtaaaag ctacaagagt gtggcactag tagtaggagt caccggcatt     120
gttggcagta gtttagccga agttctaaag ctaccagaca cccctggagg tccctggaag     180
gtatacggcg tggcaaggcg cccatgccct gtatggctag ccaaaaaacc agttgagtac     240
atccaatgtg atgtctcaga taatcaagaa acaatttcta aattatctcc acttaaggac     300
ataactcata tattctatgt ttcttggatt ggatcagaag attgccaaac aaatgctaca     360
atgttcaaaa acatccttaa ttcagtgatt cctaatgctt caaatctcca acatgtgtgt     420
ctccaaacag gaatcaaaca ttatttggt attttgaag aaggttctaa agttgtacca      480
catgattcgc cttttaccga ggatttacct aggctaaatg tcccaaattt ctaccatgat     540
cttgaagata tactgtatga agaaactggc aagaacaatt taacatggtc tgtccataga     600
ccagctctgg ttttcgggtt ttccccatgt agtatgatga acattgtcag tacattatgc     660
gtttacgcca caatttgtaa acatgaaaat aaggccttgg tttatccagg tagtaaaaat     720
tcatggaatt gttatgctga tgctgttgat gcagatttag tagccgagca cgaaatttgg     780
gcagcagttg atcctaaggc taaaaatcaa gtattgaatt gtaacaatgg ggatgttttt     840
aaatggaaac atatttggaa gaaattagca gaggaatttg ggattgaaat ggtgggatat     900
gttgaaggta agaacaagt tagtttggct gagttaatga aggataaaga tcaagtttgg      960
gatgaaattg ttaagaagaa caatttagta cctactaaat tgaaagaaat tgctgccttt    1020
tggtttgctg atattgcttt tgttctgag aatttgatta gtagtatgaa caaaagtaag     1080
gaattagggt tcttgggttt taggaattcg atgaaatcgt ttgtttcttg tattgataag    1140
atgagggatt ataggtttat tccttag                                         1167

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aagttctgtt tcagggcccg                                                   20

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
ctggtctaga aagcttta                                                     18

<210> SEQ ID NO 15
<211> LENGTH: 45
<212> TYPE: DNA
<213> ORGANISM: Artificial Sequence
<220> FEATURE:
<223> OTHER INFORMATION: primer
```

<400> SEQUENCE: 15
tgggctggac atgatgttct ccaatgcggg gatcatgagc aagtc             45

<210> SEQ ID NO 16
<211> LENGTH: 45
<212> TYPE: DNA
<213> ORGANISM: Artificial Sequence
<220> FEATURE:
<223> OTHER INFORMATION: Primer

<400> SEQUENCE: 16
ggaattcgat aaagtgatgc gcgtggccgc gcgcgggatg gctgc             45

<210> SEQ ID NO 17
<211> LENGTH: 45
<212> TYPE: DNA
<213> ORGANISM: Artificial Sequence
<220> FEATURE:
<223> OTHER INFORMATION: Primer

<400> SEQUENCE: 17
aggaacgaga ggcactatta tctgcaatac caccccgcta tcgtc             45

<210> SEQ ID NO 18
<211> LENGTH: 45
<212> TYPE: DNA
<213> ORGANISM: Artificial Sequence
<220> FEATURE:
<223> OTHER INFORMATION: Primer

<400> SEQUENCE: 18
aacgagaggc actattatct gcacggccac cccgctatcg tcgag             45

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
cgagaggcac tattatctgc acgaccggcc cgctatcgtc gagg             44

<210> SEQ ID NO 20
<211> LENGTH: 48
<212> TYPE: DNA
<213> ORGANISM: Artificial Sequence
<220> FEATURE:
<223> OTHER INFORMATION: Primer

<400> SEQUENCE: 20
aggcactatt atctgcacga ccacctcgct atcgtcgagg ggcgggca          48

<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21
cactattatc tgcacgacca ccccgtcatc gtcgaggggc gggca             45

<210> SEQ ID NO 22
<211> LENGTH: 44

<212> TYPE: DNA
<213> ORGANISM: Artificial Sequence
<220> FEATURE:
<223> OTHER INFORMATION: Primer

<400> SEQUENCE: 22 gagggcggg caaagcatga cggactttgc gatgtcgaag cacg                44

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23
aagcatgacg gactatgcga tgtcgatgca cgcagtgatg gg                 42

<210> SEQ ID NO 24
<211> LENGTH: 45
<212> TYPE: DNA
<213> ORGANISM: Artificial Sequence
<220> FEATURE:
<223> OTHER INFORMATION: Primer

<400> SEQUENCE: 24
gattagggtt aactgcgtga cgccgatggt ggtgctcacg ccgct              45

<210> SEQ ID NO 25
<211> LENGTH: 44
<212> TYPE: DNA
<213> ORGANISM: Artificial Sequence
<220> FEATURE:
<223> OTHER INFORMATION: Primer

<400> SEQUENCE: 25
tagggttaac tgcgtgacgc cgtcggcggt gctcacgccg ctcg               44

<210> SEQ ID NO 26
<211> LENGTH: 46
<212> TYPE: DNA
<213> ORGANISM: Artificial Sequence
<220> FEATURE:
<223> OTHER INFORMATION: Primer

<400> SEQUENCE: 26
ctgcgtgacg ccgtcggtgg tgctcgcgcc gctcgcccaa cggatg             46

<210> SEQ ID NO 27
<211> LENGTH: 45
<212> TYPE: DNA
<213> ORGANISM: Artificial Sequence
<220> FEATURE:
<223> OTHER INFORMATION: Primer

<400> SEQUENCE: 27
aggaacgaga ggcactatta tctgcaatgc caccccgcta tcgtc              45

<210> SEQ ID NO 28
<211> LENGTH: 45
<212> TYPE: DNA
<213> ORGANISM: Artificial Sequence
<220> FEATURE:
<223> OTHER INFORMATION: Primer

```
<400> SEQUENCE: 28
aggaacgaga ggcactatta tctgcaacgc cggcccgcta tcgtc                    45

<210> SEQ ID NO 29
<211> LENGTH: 49
<212> TYPE: DNA
<213> ORGANISM: Artificial Sequence
<220> FEATURE:
<223> OTHER INFORMATION: Primer

<400> SEQUENCE: 29
aggaacgaga ggcactatta tctgcaacgc cggtagccta tcgtcgagg                49

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
aggaacgaga ggcactatta tctgcaacgc cggtagctca tcgtcgagg                49

<210> SEQ ID NO 31
<211> LENGTH: 45
<212> TYPE: DNA
<213> ORGANISM: Artificial Sequence
<220> FEATURE:
<223> OTHER INFORMATION: Primer

<400> SEQUENCE: 31
gggaagggga gggtccatca tatgcaccgc cggctcgtcg gcggt                    45

<210> SEQ ID NO 32
<211> LENGTH: 45
<212> TYPE: DNA
<213> ORGANISM: Artificial Sequence
<220> FEATURE:
<223> OTHER INFORMATION: Primer

<400> SEQUENCE: 32
aaggggaggg tccatcatat gcaacaccgg ctcgtcggcg gtgag                    45

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
gggagggtcc atcatatgca acgccacctc gtcggcggtg agg                      43

<210> SEQ ID NO 34
<211> LENGTH: 48
<212> TYPE: DNA
<213> ORGANISM: Artificial Sequence
<220> FEATURE:
<223> OTHER INFORMATION: Primer

<400> SEQUENCE: 34
agggtccatc atatgcaacg ccggcccgtc ggcggtgagg ggcgcgca                 48

<210> SEQ ID NO 35
```

<211> LENGTH: 45
<212> TYPE: DNA
<213> ORGANISM: Artificial Sequence
<220> FEATURE:
<223> OTHER INFORMATION: Primer

<400> SEQUENCE: 35
gtccatcata tgcaacgccg gctcgctggc ggtgaggggc gcgca         45

<210> SEQ ID NO 36
<211> LENGTH: 45
<212> TYPE: DNA
<213> ORGANISM: Artificial Sequence
<220> FEATURE:
<223> OTHER INFORMATION: Primer

<400> SEQUENCE: 36
gaggggcgcg catggcgtga cggacttcgt gatgtcgaag catgc         45

<210> SEQ ID NO 37
<211> LENGTH: 49
<212> TYPE: DNA
<213> ORGANISM: Artificial Sequence
<220> FEATURE:
<223> OTHER INFORMATION: Primer

<400> SEQUENCE: 37
tggcgtgacg gactacgtga tgtcgaugca tgcggtgata gggctggtg         49

<210> SEQ ID NO 38
<211> LENGTH: 45
<212> TYPE: DNA
<213> ORGANISM: Artificial Sequence
<220> FEATURE:
<223> OTHER INFORMATION: Primer

<400> SEQUENCE: 38
tattagggtt aacagcgtgt cgccgagtgc cgtggcgacg ccgct         45

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
attggagaac atcatgtcca gccca         25

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
cacgcgcatc actttatcga attcc         25

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
gcagataata gtgcctctcg ttcct                                                    25

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
cgtgcagata atagtgcctc tcgttcc                                                  27

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
ggtcgtgcag ataatagtgc ctctcg                                                   26

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
ggtggtcgtg cagataatag tgcct                                                    25

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
cggggtggtc gtgcagataa tagtg                                                    25

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
gtccgtcatg ctttgcccgc ccctc                                                    25

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
cgacatcgca tagtccgtca tgct                                                     24

<210> SEQ ID NO 48

-continued

```
<211> LENGTH: 26
<212> TYPE: DNA
<213> ORGANISM: Artificial Sequence
<220> FEATURE:
<223> OTHER INFORMATION: Primer

<400> SEQUENCE: 48
cggcgtcacg cagttaaccc taatcc                                          26

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
cgacggcgtc acgcagttaa ccct                                            24

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
gagcaccacc gacggcgtca cgcag                                           25

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
gcagataata gtgcctctcg ttcct                                           25

<210> SEQ ID NO 52
<211> LENGTH: 25
<212> TYPE: DNA
<213> ORGANISM: Artificial Sequence
<220> FEATURE:
<223> OTHER INFORMATION: Primer

<400> SEQUENCE: 52
gcagataata gtgcctctcg ttcct                                           25

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
gcagataata gtgcctctcg ttcct                                           25

<210> SEQ ID NO 54
<211> LENGTH: 25
<212> TYPE: DNA
<213> ORGANISM: Artificial Sequence
<220> FEATURE:
<223> OTHER INFORMATION: Primer
```

```
<400> SEQUENCE: 54
gcagataata gtgcctctcg ttcct                                    25

<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55
gcatatgatg gaccctcccc ttcc                                     24

<210> SEQ ID NO 56
<211> LENGTH: 25
<212> TYPE: DNA
<213> ORGANISM: Artificial Sequence
<220> FEATURE:
<223> OTHER INFORMATION: Primer

<400> SEQUENCE: 56
gttgcatatg atggaccctc ccctt                                    25

<210> SEQ ID NO 57
<211> LENGTH: 24
<212> TYPE: DNA
<213> ORGANISM: Artificial Sequence
<220> FEATURE:
<223> OTHER INFORMATION: Primer

<400> SEQUENCE: 57
ggcgttgcat atgatggacc ctcc                                     24

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
gccggcgttg catatgatgg accct                                    25

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
cgagccggcg ttgcatatga tggac                                    25

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
gtccgtcacg ccatgcgcgc ccctc                                    25

<210> SEQ ID NO 61
```

```
<211> LENGTH: 25
<212> TYPE: DNA
<213> ORGANISM: Artificial Sequence
<220> FEATURE:
<223> OTHER INFORMATION: Primer

<400> SEQUENCE: 61
cgacatcacg tagtccgtca cgcca                                          25

<210> SEQ ID NO 62
<211> LENGTH: 28
<212> TYPE: DNA
<213> ORGANISM: Artificial Sequence
<220> FEATURE:
<223> OTHER INFORMATION: Primer

<400> SEQUENCE: 62
cggcgacacg ctgttaaccc taatactg                                       28

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
atggcaagca ctgcaaatcc                                                20

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
atgggcaaca agaagacgc                                                 19

<210> SEQ ID NO 65
<211> LENGTH: 27
<212> TYPE: DNA
<213> ORGANISM: Artificial Sequence
<220> FEATURE:
<223> OTHER INFORMATION: Primer

<400> SEQUENCE: 65
atggctaaca attcagtgat gatgaag                                        27

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
atggcgaaat caccagaaac ag                                             22

<210> SEQ ID NO 67
<211> LENGTH: 20
<212> TYPE: DNA
<213> ORGANISM: Artificial Sequence
<220> FEATURE:
<223> OTHER INFORMATION: Primer
```

<400> SEQUENCE: 67
atggcgaaat cagtgaacgc                                          20

<210> SEQ ID NO 68
<211> LENGTH: 17
<212> TYPE: DNA
<213> ORGANISM: Artificial Sequence
<220> FEATURE:
<223> OTHER INFORMATION: Primer

<400> SEQUENCE: 68
atggccgaca acaccac                                             17

<210> SEQ ID NO 69
<211> LENGTH: 29
<212> TYPE: DNA
<213> ORGANISM: Artificial Sequence
<220> FEATURE:
<223> OTHER INFORMATION: Primer

<400> SEQUENCE: 69
ctgaaggagc aaagaatggt aaacaaagc                                29

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
tgatgttggt gcaaagaatg gt                                       22

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
tgctgaaccg aggagaaatg g                                        21

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
gtcggctttc agtgaaccg                                           19

<210> SEQ ID NO 73
<211> LENGTH: 23
<212> TYPE: DNA
<213> ORGANISM: Artificial Sequence
<220> FEATURE:
<223> OTHER INFORMATION: Primer

<400> SEQUENCE: 73
atcggtttca gtcagcgtat tcc                                      23

<210> SEQ ID NO 74

```
<211> LENGTH: 30
<212> TYPE: DNA
<213> ORGANISM: Artificial Sequence
<220> FEATURE:
<223> OTHER INFORMATION: Primer

<400> SEQUENCE: 74
gaacttgata ataaccttga cacaatcagg                                          30
```